(12) United States Patent
Gaul et al.

(10) Patent No.: US 8,022,209 B2
(45) Date of Patent: Sep. 20, 2011

(54) SUBSTITUTED NITROGEN-CONTAINING HETEROARYL DERIVATIVES USEFUL AS MODULATORS OF THE HISTAMINE $H_4$ RECEPTOR

(75) Inventors: Michael D. Gaul, Yardley, PA (US); Bao-Ping Zhao, West Windsor, NJ (US); Xizhen Zhu, Monmouth Junction, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 354 days.

(21) Appl. No.: 12/283,488

(22) Filed: Sep. 11, 2008

(65) Prior Publication Data

US 2009/0069305 A1 Mar. 12, 2009

Related U.S. Application Data

(60) Provisional application No. 60/971,676, filed on Sep. 12, 2007.

(51) Int. Cl.
*C07D 403/00* (2006.01)
(52) U.S. Cl. ...................................... 544/359
(58) Field of Classification Search ............. 514/252.13; 544/359
See application file for complete search history.

(56) References Cited

FOREIGN PATENT DOCUMENTS

| WO | WO 01/47897 A1 | 7/2001 |
| WO | WO 2007/031529 A1 | 3/2007 |

OTHER PUBLICATIONS

Herdewijn et al., 2008, CAS: 148:191956.*
Lehmann-Lintz et al., 2001, CAS: 134:266313.*
Roch et al., 1978, CAS: 89:6322.*
Dunford, P.J. et al. The histamine H4 receptor mediates allergic airway inflammation by regulating the activation of CD4+ T cells. Journal of Immunology, 2006. vol. 176(11), 7062-7070.
Dunford et al.,"Histamine H4 receptor antagonists are superior to traditional antihistamines in the attenuation of experimental pruritus" J. Allergy Clin. Immun., 2007, 119(1),pp. 176-183.
Fleisher et al. "Improved Oral Delivery: Solubility Limitations Overcome by the Use of Prodrugs" Advanced Drug Delivery Review 1996 vol. 19 pp. 115-130.
Fokkens et al "Dynamics of Mast Cells in the Nasal Mucosa of Patients with Allergic Rhinitis and Non-Allergic Controls: A Biopsy Study" Clin Exp Allergy 1992 vol. 22(7) pp. 701-710.
Fung-Leung et al. "Histamine $H_4$ Receptor Antagonists: The New Antihistamines?" Curr Opin Invest Drugs 2004 vol. 5(11) pp. 1174-1183.
Gantner et al. "Histamines $H_4$ and $H_2$ Receptors Control Histamine-Induced Interleukin-16 Release from Human CD8+ T Cells" J Pharmacol Exp 2002 vol. 303(1) pp. 300-307.

Gauvreau et al "Increased Numbers of Both Airway Basophils and Mast Cells in Sputum after Allergen Inhalation Challenge of Atopic Asthmatics" Am J Resp Crit Care Med 2002 vol. 161(5) pp. 1473-1478.
Greenwald et al. "Drug delivery systems. 2. Camptothecin 20-O-poly(ethylene glycol) ester transport forms" Journal of Medicinal Chemistry, 1996, 39(10), pp. 1938-1940.
Gutzmer et al "Histamine $H^4$ Receptor Stimulation Suppresses IL-12p70 Production and Mediates Chemotaxis in Human Monocyte-Derived Dendritic Cells" J Immunol 2005 vol. 174(9) pp. 5224-5232.
Hofstra et al "Histamine $H^4$ Receptor Mediates Chemotaxis and Calcium Mobilization of Mast Cells" J Pharmacol Exp Ther 2003 vol. 305(3) pp. 1212-1221.
Horr et al. STAT1 phosphorylation and cleavage is regulated by the histamine (H4) receptor in human atopic and non-atopic lymphocytes. International Immunopharmacology 2006. vol. 6 (10), 1577-1585.
Ikawa et al "Histamine $H^4$ Receptor Expression in Human Synovial Cells Obtained from Patients Suffering from Rheumatoid Arthristis" Biol Pharm Bull 2005 vol. 28(10) pp. 2016-2018.
Jablonowski, J. et al., The first potent and selective non-imidazole human histamine H4 receptor antagonists. Journal of Medicinal Chemistry, 2003. vol. 46(19), 3957-3960.
Jiang et al. Cloning and pharmacological characterization of the dog histamine H-4 receptor. European Journal of Pharmacology, 2008. vol. 592(1-3), 26-32.
Jokuti et al. Histamine H4 receptor expression is elevated in human nasal polyp tissue, Cell Biology International. 2007 vol. 31(11) 1367-1370.
Kassel et al. "Local Increase in the Number of Mast Cells and Expression of Nerve Growth Factor in the Bronchus of Asthmatic Patients after Repeated Inhalation of Allergen Low-Dose" Clin Exp Allergy 2001 vol. 31(9) pp. 1432-1440.
Kirby et al "Bronchoalveolar Cell Profiles of Asthmatic and NonAsthmatic Subjects" Am Rev Respir 1987 vol. 136(2) pp. 379-383.
Lee-Dutra, A. et al., Identification of 2-arylbenzimidazoles as potent human histamine H-4 receptor ligands, Bioorganic & Medicinal Chemistry Letters 2006. vol. 16(23), 6043-6048.
Leite-de-Moraes, Cutting edge: histamine receptor H4 activation positively regulates in vivo IL-4 and IFN-gamma production by invariant NKT cells. Journal of Immunology, 2009. 182(3):1233-1236.
Libby P. "Inflammation in Atherosclerosis" Nature 2002 vol. 420 pp. 868-874.
Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.
Ling et al. "Histamine $H^4$ Receptor Mediates Eosiniphil Chemolaxis with Cell Shape Change and Adhesion Molecule Upregulation" Br J. Pharmacol 2004 vol. 104(1) pp. 161-171. Liu et al "Cloning of Pharmacological Characterization of a Fourth Histamine Receptor ($H^4$) Expressed in Bone Marro" Mol Pharmacol 2001 vol. 59(3) pp. 420-426.

(Continued)

*Primary Examiner* — Rei-tsang Shiao

(57) ABSTRACT

The present invention relates to substituted nitrogen-containing heteroaryl derivatives, pharmaceutical compositions containing them, and methods of using any of these derivatives and compositions for $H_4$ receptor activity modulation and the treatment of states mediated by histamine $H_4$ receptor activity.

5 Claims, No Drawings

OTHER PUBLICATIONS

Mashikian et al "Identification of IL-16 as the Lymphocyte Chemotactic Activity in the Bronchoalveolar Lavage Fluid of Histamine-Challenged Asthmatic Patients" J Allergy Clin Immunol 1998 vol. 101(6 Part 1) pp. 786-792.

Morse et al "Cloning and Characterization of Novel Human Histamine Receptor" J Pharmacol Exp. Ther 2001 vol. 296(3) pp. 1058-1066.

Nathan C. "Points of Control in Inflammation" Nature 2002 vol. 420(6917) pp. 846-852.

O'Reilly et al "Identification of $H^4$ Receptor in Human Eosinophilis—Role in Eosinophil Chemotaxis" J Recept Signal Transduction 2002 vol. 22(1-4) pp. 431-448.

Robinson et al. "Discovery of the hemifumarate and (alpha-L-alanyloxy)methyl ether as prodrugs of an antirheumatic oxindole: Prodrugs for the enolic OH group", Journal of Medicinal Chemistry, 1996, 39(1), pp. 10-18.

Shan et al. "Prodrug strategies based on intramolecular cyclization reactions", Journal of Pharmaceutical Sciences 1997, 86(7), pp. 765-767.

Slater et al "Increase in epithelial Mast Cell Numbers in the Nasal Mucosa of Patients with Perennial Allergic Rhinitis" J Laryngol Otol 1996 vol. 110 pp. 929-933.

Smits, R.A. et al. Major advances in the development of histamine H4 receptor ligands. Drug Discovery Today, 2009, vol. 14(15-16):745-753.

Steinberg D. " Atherogenesis in Perspective: Hypercholesterolemia and Inflammation as Partners in Crime" Nature Med 2002 vol. 8(11) pp. 1211-1217.

Kiss, R., et al., histamine H4 receptor ligands and their potential therapeutic applications; Expert Opinion Ther. Patents, 2009, 19(2), 119-135.

Krug, et al., Inerleukin 16 and T-cell chemoattractant activity in bronchoalveolar lavage 24h after allergen challenge in asthma; Am J Resp Crit Care Med 2000, 162(1), 105-111.

Takeshita et al "Critical Role of Histamine $H_4$ Receptor in Leukotriene $B_4$ Production and Mast-Cell Dependent Neutrophil Recruitment Induced by Zymosan in Vivo" J Pharmacol Exp Ther 2003 vol. 307(3) pp. 1072-1078.

Thurmond et al "A Potent and Selective Histamine $H_4$ Receptor Antagonist with Anti-Inflammatory Properties" J Pharmacol Exp Ther 2004 vol. 309(1) pp. 404-413.

Thurmond R. L. et al , The role of histamine H1 and H4 receptors in allergic inflammation: the search for new antihistamines. Nat. Rev. Drug Disc. 2008 vol. 7(1), 45-53.

Tracey K. J. "The Inflammatory Reflex" Nature 2002 vol. 420(6917) pp. 853-859.

Varga et al "Inhibitory Effects of Histamine $H^4$ Receptor Antagonists on Experimental Colitis in the Rat" Eur J Pharmacol 2005 vol. 522(1-3) pp. 130-138.

Voehringer et al "Type 2 Immunity Reflects Orchestrated Recruitment of Cells Committed to IL-4 Production" Immunity 2004 vol. 20(3) pp. 267-277.

Weiner et al "Inflammation and Therapeutic Vaccination in CNS Diseases" Nature 2002 vol. 420(6917) pp. 879-884.

Zhang et al., "The histamine $H_4$ receptor in autoimmune disease " 2006 Expert Opinion Invest. Drugs, vol. 15(11), pp. 1443-1452.

Zhang et al., "The histamine $H_4$ receptor: A novel modulator of inflammatory and immune disorders" Pharmacology and Therapeutic, vol. 113, pp. 594-606.

Venable et al. "Preparation and Biological Evaluation of Indole, Benzimidazole, and Thienopyrrole Piperazine Carboxamides: Potent Human Histamine H4 Antagonists". J. Med. Chem., 2005, vol. 48 (26), pp. 8289-8298, abstract only.

International Search Report dated Dec. 24, 2008 for International Appln. No. PCT/US08/10673.

Venable, J.D., et al. "Preparation and Biological Evaluation of Indole, Benzimidazole, and Thienopyrrole Piperazine Carxboxamides: Potent Human Histamine $H_4$ Antagonists". Journal of Medicinal Chemistry. 2005, vol. 48, No. 26 pp. 8289-8298 (Full article).

* cited by examiner

SUBSTITUTED NITROGEN-CONTAINING HETEROARYL DERIVATIVES USEFUL AS MODULATORS OF THE HISTAMINE $H_4$ RECEPTOR

This application claims the benefit of U.S. provisional patent application Ser. No. 60/971,676, filed on Sep. 12, 2007, which is incorporated herein by reference in its entirety.

FIELD OF THE INVENTION

The present invention relates to substituted nitrogen-containing heteroaryl derivatives, pharmaceutical compositions containing them, and methods of using any of these derivatives and compositions for $H_4$ receptor activity modulation and the treatment of disease states, disorders, and conditions mediated by histamine $H_4$ receptor activity.

BACKGROUND OF THE INVENTION

The histamine $H_4$ receptor ($H_4R$) is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in $CD8^+$ T cells has also been reported. Gantner, et al., (2002) showed that both $H_4$ and $H_2$ receptors control histamine-induced IL-16 release from human $CD8^+$ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in $CD4^+$ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritus. The histamine $H_4$ receptor has also been shown to be involved in the pruritic responses in mice to a greater degree than the histamine H1 receptor (Dunford, P. J., et al., J, Allergy Clin Immun. 2007. 119(1), 176-183).

Modulation of H$_4$ receptors controls the release of inflammatory mediators and inhibits leukocyte recruitment, thus providing the ability to prevent and/or treat H$_4$-mediated diseases and conditions, including the deleterious effects of allergic responses such as inflammation. Recently, two selected histamine H$_4$ receptor antagonists have been shown to exhibit anti-inflammatory and anti-nociceptive activity in the rat model of carrageenan-induced acute inflammation (Coruzzi, G., et al., Eur. J. Pharm., 2007, 563, 240-244). Compounds according to the present invention have H$_4$ receptor modulating properties. Compounds according to the present invention have leukocyte recruitment inhibiting properties. Compounds according to the present invention have anti-inflammatory properties.

Examples of textbooks on the subject of inflammation include: 1) Gallin, J. I.; Snyderman, R., *Inflammation: Basic Principles and Clinical Correlates*, 3rd ed.; Lippincoft Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine*, 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Examples of review articles on the role of the histamine H$_4$ receptor include: Zhang, M., et al., Expert Opin. Investig. Drugs., 2006, 15(11), 1443-1452 and Zhang, M., et al., Pharmacology and Therapeutic, 2007 113, 594-606.

There remains however, a need for potent histamine H$_4$ receptor modulators with desirable pharmaceutical properties. The small-molecule histamine H$_4$ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritus, and immunodeficiency disorders. Diseases, disorders and medical conditions that are mediated by histamine H$_4$ receptor activity include those referred to herein.

SUMMARY OF THE INVENTION

The present invention is directed to compounds of Formula (I), pharmaceutically acceptable salts of compounds of Formula (I), pharmaceutically acceptable prodrugs of compounds of Formula (I), and pharmaceutically active metabolites of Formula (I):

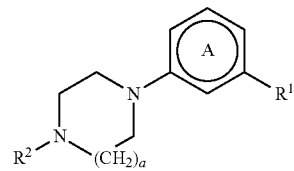

(I)

wherein
the moiety

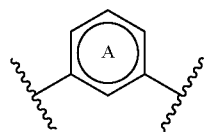

is selected from the group consisting of

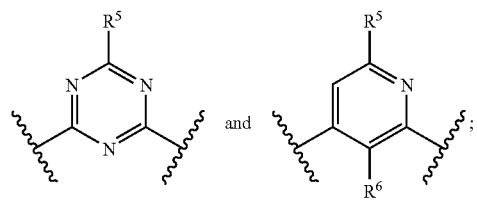

wherein $R^5$ and $R^6$ are each independently selected from the group consisting of H, halo (for example, chloro) and $C_{1-4}$alkyl (for example, methyl);

$R^1$ is selected from the group consisting of aryl and heteroaryl;

wherein the aryl or heteroaryl is optionally substituted with one or more (for example, one to three) substituents independently selected from the group consisting of halo, hydroxy, $C_{1-4}$alkyl, halogenated $C_{1-4}$alkyl, hydroxy substituted $C_{1-4}$alkyl, $C_{2-4}$alkenyl, $C_{1-4}$alkoxy, cyano, nitro, $NR^AR^B$, —$C_{1-4}$alkyl-O—$C_{1-4}$alkyl, —$C_{1-4}$alkyl-$NR^AR^B$, phenyl, substituted phenyl and 5 to 6 membered heteroaryl;

wherein $R^A$ and $R^B$ are each independently selected from the group consisting of H and $C_{1-4}$alkyl;

wherein the substituted phenyl is substituted with one or more (for example, one to two) substituents independently selected from the group consisting of halo, cyano, $C_{1-4}$alkyl, $C_{1-4}$alkoxy, —$NR^CR^D$, —C(O)—$NR^CR^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl);

wherein $R^C$ and $R^D$ are each independently selected from the group consisting of H and $C_{1-4}$alkyl; alternatively, $R^C$ and $R^D$ are taken together with the nitrogen member to which they are bound to from a 5 to 6 membered, saturated, nitrogen-containing ring structure (for example, 4-morpholinyl or 1-pyrrolidinyl);

and wherein $R^E$ is selected from the group consisting of H and $C_{1-4}$alkyl;

a is 1 or 2;

$R^2$ is selected from the group consisting of H and $C_{1-4}$alkyl;

provided that when moiety

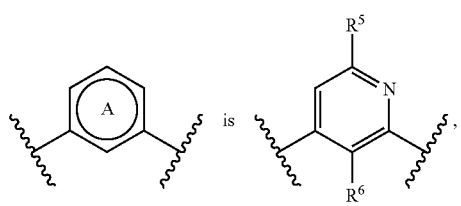

$R^5$ and $R^6$ are each H, a is 1 and $R^2$ is H, then $R^1$ is not phenyl or 2,3-dihydroxy, 6,7-dimethoxy-naphth-1-yl.

The present invention is further directed to a process for the preparation of compounds of formula (I-P), pharmaceutically acceptable salts of compounds of Formula (I-P), pharmaceutically acceptable prodrugs of compounds of Formula (I-P), and pharmaceutically active metabolites of Formula (I-P):

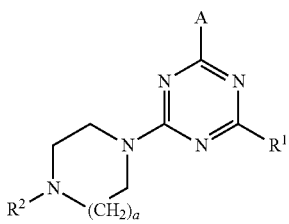

(I-P)

wherein

A is selected from the group consisting of H and $C_{1-4}$alkyl;

$R^1$ is selected from the group consisting of aryl and heteroaryl;

wherein the aryl or heteroaryl is optionally substituted with one or more substituents independently selected from the group consisting of halo, hydroxy, $C_{1-4}$alkyl, halogenated $C_{1-4}$alkyl, hydroxy substituted $C_{1-4}$alkyl, $C_{2-4}$alkenyl, $C_{1-4}$alkoxy, cyano, nitro, $NR^A R^B$, —$C_{1-4}$alkyl-O—$C_{1-4}$alkyl, —$C_{1-4}$alkyl-$NR^A R^B$, phenyl, substituted phenyl and 5 to 6 membered heteroaryl;

wherein $R^A$ and $R^B$ are each independently selected from the group consisting of H and $C_{1-4}$alkyl;

wherein the substituted phenyl is substituted with one or more substituents independently selected from the group consisting of halo, cyano, $C_{1-4}$alkyl, $C_{1-4}$alkoxy, —$NR^C R^D$, —C(O)—$NR^C R^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl);

wherein $R^C$ and $R^D$ are each independently selected from the group consisting of H and $C_{1-4}$alkyl; alternatively, $R^C$ and $R^D$ are taken together with the nitrogen member to which they are bound to from a 5 to 6 membered, saturated, nitrogen-containing ring;

and wherein $R^E$ is selected from the group consisting of H and $C_{1-4}$alkyl;

a is 1 or 2;

$R^2$ is selected from the group consisting of H and $C_{1-4}$alkyl;

comprising

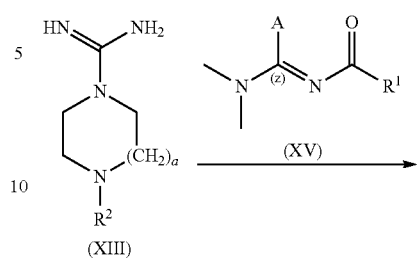

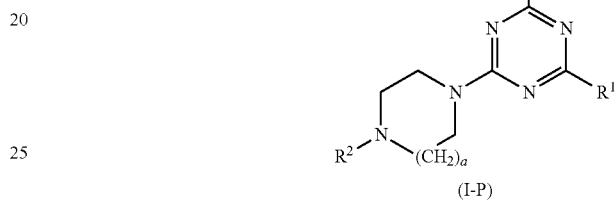

reacting a compound of formula (XII) with a compound of formula (XV), in an organic solvent, to yield the corresponding compound of formula (I-P). Further embodiments comprise this reacting in the presence of an inorganic base.

The present invention is further directed to a product prepared according to any of the processes described herein.

The present invention is further directed to pyridyl and pyrimidyl derivatives as listed in Tables 3 and 4 herein, pharmaceutically acceptable salts of said compounds, pharmaceutically acceptable prodrugs of said compounds, and pharmaceutically active metabolites of said compounds.

In a further aspect, the invention relates to pharmaceutical compositions each comprising at least one of: an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I).

In a further aspect, the invention relates to pharmaceutical compositions each comprising at least one of: an effective amount of at least one chemical entity selected from the compounds listed in Tables 3 and 4 herein, pharmaceutically acceptable salts of the compounds listed in Tables 3 and 4 herein, pharmaceutically acceptable prodrugs of the compounds listed in Tables 3 and 4 herein, and pharmaceutically active metabolites of the compounds listed in Tables 3 and 4 herein.

In another aspect, the present invention is directed to a method for modulating histamine $H_4$ receptor activity, comprising exposing histamine $H_4$ receptor to an effective amount of at least one chemical entity selected from compounds of Formula (I) and pharmaceutically acceptable salts, prodrugs, and active metabolites of compounds of Formula (I).

In another aspect, the present invention is directed to a method for modulating histamine $H_4$ receptor activity, comprising exposing histamine $H_4$ receptor to an effective amount of at least one chemical entity selected from the compounds as listed in Tables 3 and 4 herein and pharmaceutically acceptable salts of the compounds as listed in Tables 3 and 4 herein.

The present invention is further directed to a method of treating a subject suffering from or diagnosed with a disease, disorder, or medical condition mediated by histamine $H_4$ receptor activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

The present invention is further directed to a method of treating a subject suffering from or diagnosed with a disease, disorder, or medical condition mediated by histamine $H_4$ receptor activity, comprising administering to the subject in need of such treatment an effective amount of at least one chemical entity selected from the compounds listed in Tables 3 and 4 herein, pharmaceutically acceptable salts of the compounds listed in Tables 3 and 4 herein, pharmaceutically acceptable prodrugs of the compounds listed in Tables 3 and 4 herein, and pharmaceutically active metabolites of the compounds listed in Tables 3 and 4 herein.

In an embodiment, the present invention is directed to methods of treating a disorder mediated by the histamine $H_4$ receptor (selected from the group consisting of inflammation and/or inflammatory disease, allergic disorders, dermatological disorders, autoimmune diseases, lymphatic disorders, pruritus and immunodeficiency disorders) comprising administering to a subject in need thereof a therapeutically effective amount of any of the compounds or pharmaceutical compositions described above.

In certain embodiments of the present inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

Another example of the invention is the use of at least one of a compound of Formula (I), a pharmaceutically acceptable salt of a compounds of Formula (I), a pharmaceutically acceptable prodrug of a compound of Formula (I), and a pharmaceutically active metabolite of a compound of Formula (I) in the preparation of a medicament for treating a disorder mediated by the histamine $H_4$ receptor.

Another example of the invention is the use of at least one of any of the compounds listed in Tables 3 and 4 herein, a pharmaceutically acceptable salt of any of the compounds listed in Tables 3 and 4 herein, a pharmaceutically acceptable prodrug of any of the compounds listed in Tables 3 and 4 herein, and a pharmaceutically active metabolite of any of the compounds listed in Tables 3 and 4 herein in the preparation of a medicament for treating a disorder mediated by the histamine $H_4$ receptor.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND EMBODIMENTS

The present invention is directed to compounds of Formula (I):

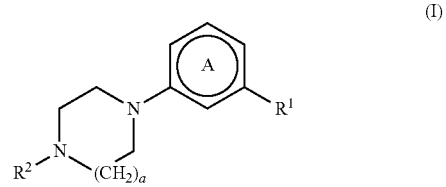

wherein the moiety

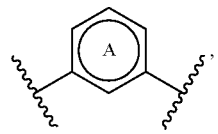

$R^1$, a and $R^2$ are as herein defined, pharmaceutically acceptable salts of compounds of Formula (I), pharmaceutically acceptable prodrugs of compounds of Formula (I), and pharmaceutically active metabolites of Formula (I). The compounds of formula (I) are useful as modulators of the H4 receptor.

The present invention is further directed to pyridyl and pyrimidinyl derivatives as described in Tables 3 and 4 herein, pharmaceutically acceptable salts of said compounds, pharmaceutically acceptable prodrugs of said compounds, and pharmaceutically active metabolites of said compounds. The pyridyl and pyrimidinyl derivatives as described in Table 4 and 5 herein are useful as modulators of the $H_4$ receptor.

For the sake of brevity, the disclosures of the publications, including patents, cited in this specification are herein incorporated by reference.

As used herein, the terms "including", "containing" and "comprising" are used herein in their open, non-limiting sense.

As used herein, "halo" means any one of chloro, bromo, fluoro and iodo.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and groups that in light of the ordinary skill in the art and the teachings provided herein would be considered equivalent to any one of the foregoing examples. Unless otherwise noted, "$C_{1-4}$" when used with alkyl means a carbon chain composition of 1-4 carbon atoms.

As used herein, the term "alkenyl" whether used alone or as part of a substituent group, include straight and branched chains comprising at least one (for example, one) unsaturated double bond. For example, alkyl radicals include vinyl, propenyl or isopropenyl. Unless otherwise noted, "$C_{2-4}$" when used with alkenyl means a carbon chain composition of 1-4 carbon atoms, wherein the carbon chain compositions contains at least one unsaturated, double bond.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy, and groups that in light of the ordinary skill in the art and the teachings provided herein would be considered equivalent to any one of the foregoing examples. Unless otherwise noted, "$C_{1-4}$" when used with alkoxy means an oxygen ether radical of the above described straight or branched chain alkyl groups comprising 1-4 carbon atoms.

As used herein, unless otherwise noted, "aryl" shall refer to unsubstituted carbocyclic aromatic groups such as phenyl, naphthyl, and groups that in light of the ordinary skill in the art and the teachings provided herein would be considered equivalent to any one of the foregoing examples. In an embodiment of the present invention, the aryl group is phenyl.

As used herein, unless otherwise noted, "heteroaryl" shall denote five to six membered monocyclic aromatic ring structure containing at least one heteroatom selected from the group consisting of O, N and S, optionally containing one to three additional heteroatoms independently selected from the group consisting of O, N and S; or a nine to ten membered bicyclic aromatic ring structure containing at least one heteroatom selected from the group consisting of O, N and S, optionally containing one to four additional heteroatoms independently selected from the group consisting of O, N and S; or a thirteen to fourteen membered tricyclic, dibenzo-fused aromatic ring structure containing at least one heteroatom selected from the group consisting of O, N and S, optionally containing one to three additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, dibenzofuryl, dibenzothienyl, acridinyl, and groups that in light of the ordinary skill in the art and the teachings provided herein would be considered equivalent to any one of the foregoing examples.

In an embodiment of the present invention, the heteroaryl groups is selected from the group consisting of furyl, thienyl, pyridyl, benzothienyl, benzofuryl and dibenzofuryl. In another embodiment of the present invention, the heteroaryl group is any ring structure as herein defined containing one to two heteroatoms independently selected from the group consisting of N, O and S. In another embodiment of the present invention, the heteroaryl group is any ring structure as herein defined containing one heteroatom selected from the group consisting of N, O and S.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. When a particular group is "substituted" (e.g., alkyl, phenyl, aryl, heteroaryl, etc.), that group may have one or more substituents, for example, from one to five substituents, or from one to three substituents, or from one to two substituents, independently selected from the list of substituents.

With reference to substituents, the term "independently" means that when more than one of such substituents is possible, such substituents may be the same or different from each other.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

As used herein, unless otherwise noted, the term "aprotic solvent" shall mean any solvent with a pKa less than about 20. Suitable examples include, but are not limited to DMF, 1,4-dioxane, THF, acetonitrile, pyridine, dichloroethane, dichloromethane, MTBE, toluene or acetone.

As used herein, unless otherwise noted, the term "leaving group" shall mean a charged or uncharged atom or group that departs during a substitution or displacement reaction. Examples include, but are not limited to, Br, Cl, I, mesylate and tosylate.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labelled compounds are useful in metabolic studies (for example, with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{exampe}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-4}$, A, X, $R^{A-D}$ and a, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-4}$, A, X, $R^{A-D}$ and a, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies $n \leq N \leq m$, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Abbreviations used in the specification, particularly the Schemes and Examples, are as follows
BOC or Boc=t-Butoxycarbonyl (i.e., —C(O)—OC(CH$_3$)$_3$)
CBz=Benzyloxycarbonyl (i.e., —C(O)—O-benzyl)
DCE=Dichloroethane
DCM Dichloromethane
DDQ=2,3-Dichloro-5,6-dicyanobenzoquinone
dppf=1,1'Bis(diphenylphosphino)ferrocene
DIPEA or DIEA Diisopropylethylamine
DME=N,N-Dimethylethylenediamine DMF=N,N-Dimethylformamide
EDC=1,2-Dicloroethane
Et$_2$O=Diethyl ether
EtOAc=Ethyl acetate
EtOH=Ethanol
HPLC=High Pressure Liquid Chromatography
KOtBu=Potassium t-butoxide
LDA=Lithium Diisopropylamide
MeOH=Methanol
NaB(OAc)$_3$H=Sodium triacetoxyborohydride
NaOtBu=Sodium t-Butoxide
n-BuLi=n-Butyl lithium
PCC=Pyridinium dichromate
Pd/C=Palladium on Carbon Catalyst
Pd$_2$(OAc)$_2$=Palladium(II)acetate
Pd$_2$(dba)$_3$=Tris(dibenzylidene acetone)dipalladium(0)
Pd(PPh$_3$)$_4$=Tetrakistriphenylphosphine palladium (0)
Pd(PPh$_3$)$_2$Cl$_2$ Bis(triphenylphosphine)palladium (II) chloride
Pd(P$^t$-Bu$_3$)$_2$ or Pd[P(t-Bu)$_3$]$_2$=Bis(tri-t-butylphosphine)palladium(0)
Ph$_3$P or PPh$_3$=Triphenylphosphine
RT or rt=Room temperature
TBAF=Tetra-n-butylammonium fluoride
TEA=Triethylamine
TFA=Trifluoroacetic Acid
THF=Tetrahydrofuran
TLC=Thin Layer Chromatography
Tris HCl or Tris-Cl=Tris[hydroxymethyl]aminomethyl hydrochloride In an embodiment, the present invention is directed to a compound selected from the group consisting of compounds of formula (I-A), pharmaceutically acceptable salts of compounds of Formula (I-A), pharmaceutically acceptable prodrugs of compounds of Formula (I-A), and pharmaceutically active metabolites of Formula (I-A):

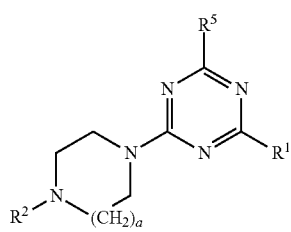

(I-A)

wherein
$R^5$ is selected from the group consisting of H, halo and $C_{1-4}$alkyl;
$R^1$ is selected from the group consisting of aryl and heteroaryl;
wherein the aryl or heteroaryl is optionally substituted with one or more substituents independently selected from the group consisting of halo, hydroxy, $C_{1-4}$alkyl, halogenated $C_{1-4}$alkyl, hydroxy substituted $C_{1-4}$alkyl, $C_{2-4}$alkenyl, $C_{1-4}$alkoxy, cyano, nitro, $NR^AR^B$, —$C_{1-4}$alkyl-O—$C_{1-4}$alkyl, —$NR^AR^B$, phenyl, substituted phenyl and 5 to 6 membered heteroaryl;
wherein $R^A$ and $R^B$ are each independently selected from the group consisting of H and $C_{1-4}$alkyl;
wherein the substituted phenyl is substituted with one or more substituents independently selected from the group consisting of halo, cyano, $C_{1-4}$alkyl, $C_{1-4}$alkoxy, —$NR^CR^D$, —C(O)—$NR^CR^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl);
wherein $R^C$ and $R^D$ are each independently selected from the group consisting of H and $C_{1-4}$alkyl; alternatively, $R^C$ and $R^D$ are taken together with the nitrogen atom to which they are bound to from a 5 to 6 membered, saturated, nitrogen-containing ring structure;
and wherein $R^E$ is selected from the group consisting of H and $C_{1-4}$alkyl;
a is 1 or 2;
$R^2$ is selected from the group consisting of H and $C_{1-4}$alkyl.

In an embodiment, the present invention is directed to a compound selected from the group consisting of compounds of formula (I-B), pharmaceutically acceptable salts of compounds of Formula (I-B), pharmaceutically acceptable prodrugs of compounds of Formula (I-B), and pharmaceutically active metabolites of Formula (I-B):

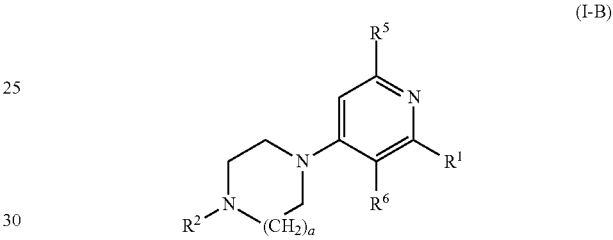

(I-B)

wherein
$R^5$ and $R^6$ are each independently selected from the group consisting of H, halo and $C_{1-4}$alkyl;
$R^1$ is selected from the group consisting of aryl and heteroaryl;
wherein the aryl or heteroaryl is optionally substituted with one or more substituents independently selected from the group consisting of halo, hydroxy, $C_{1-4}$alkyl, halogenated $C_{1-4}$alkyl, hydroxy substituted $C_{1-4}$alkyl, $C_{2-4}$alkenyl, $C_{1-4}$alkoxy, cyano, nitro, $NR^AR^B$, —$C_{1-4}$alkyl-O—$C_{1-4}$alkyl, —$C_{1-4}$alkyl-$NR^AR^B$, phenyl, substituted phenyl and 5 to 6 membered heteroaryl;
wherein $R^A$ and $R^B$ are each independently selected from the group consisting of H and $C_{1-4}$alkyl;
wherein the substituted phenyl is substituted with one or more substituents independently selected from the group consisting of halo, cyano, $C_{1-4}$alkyl, $C_{1-4}$alkoxy, —$NR^CR^D$, —C(O)—$NR^CR^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl);
wherein $R^C$ and $R^D$ are each independently selected from the group consisting of H and $C_{1-4}$alkyl; alternatively, $R^C$ and $R^D$ are taken together with the nitrogen atom to which they are bound to from a 5 to 6 membered, saturated, nitrogen-containing ring structure;
and wherein $R^E$ is selected from the group consisting of H and $C_{1-4}$alkyl;
a is 1 or 2;
$R^2$ is selected from the group consisting of H and $C_{1-4}$alkyl;
provided that when $R^5$ and $R^6$ are each H, a is 1, and $R^2$ is H, then $R^1$ is not phenyl or 2,3-dihydroxy, 6,7-dimethoxy-naphth-1-yl.

In an embodiment of the present invention, moiety

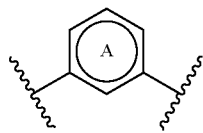

is

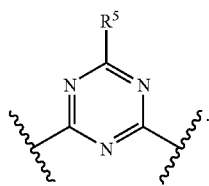

In another embodiment of the present invention, moiety

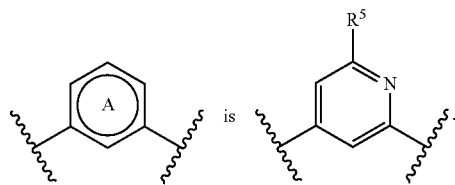

In an embodiment of the present invention, $R^5$ is selected from the group consisting H, halo and $C_{1-2}$alkyl. In another embodiment of the present invention, $R^5$ is selected from the group consisting of H, chloro and methyl. In another embodiment of the present invention, $R^5$ is selected from the group consisting of H, methyl and ethyl. In another embodiment of the present invention, $R^5$ is selected from the group consisting of H and methyl. In another embodiment of the present invention, $R^5$ is H.

In an embodiment of the present invention, $R^6$ is selected from the group consisting H, halo and $C_{1-2}$alkyl. In another embodiment of the present invention, $R^6$ is selected from the group consisting of H, chloro and methyl. In another embodiment of the present invention, $R^6$ is selected from the group consisting of H, methyl and ethyl. In another embodiment of the present invention, $R^6$ is selected from the group consisting of H and methyl. In another embodiment of the present invention, $R^6$ is H.

In an embodiment of the present invention, $R^1$ is selected from the group consisting of aryl and heteroaryl; wherein the heteroaryl contains one heteroatom independently selected from the group consisting of N, O and S; wherein the aryl or heteroaryl is optionally substituted with one to three substituents independently selected from the group consisting of halo, hydroxy, $C_{1-4}$alkyl, fluorinated $C_{1-4}$alkyl, hydroxy substituted $C_{1-4}$alkyl, $C_{2-4}$alkenyl, $C_{1-4}$alkoxy, cyano, nitro, $NR^AR^B$, —$C_{1-4}$alkyl-O—$C_{1-4}$alkyl, —$C_{1-4}$alkyl-$NR^AR^B$, phenyl, substituted phenyl and 5 to 6 membered heteroaryl; wherein $R^A$ and $R^B$ are each independently selected from the group consisting of H and $C_{1-2}$alkyl; wherein the substituted phenyl is substituted with one or more substituents independently selected from the group consisting of halo, cyano, $C_{1-4}$alkyl, $C_{1-4}$alkoxy, —$NR^CR^D$, —C(O)—$NR^CR^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl); wherein $R^C$ and $R^D$ are each independently selected from the group consisting of H and $C_{1-2}$alkyl; and wherein $R^E$ is selected from the group consisting of H and $C_{1-2}$alkyl.

In another embodiment of the present invention, $R^1$ is selected from the group consisting of phenyl, naphthyl, furyl, thienyl, pyridyl, indolyl, benzofuryl, benzothienyl and dibenzofuryl; wherein the phenyl, naphthyl, furyl, thienyl, pyridyl, indolyl, benzofuryl, benzothienyl or dibenzofuryl is optionally substituted with one to three substituents independently selected from the group consisting of halo, hydroxy, $C_{1-4}$alkyl, hydroxy substituted $C_{1-2}$alkyl, trifluoromethyl, $C_{2-4}$alkenyl, $C_{1-2}$alkoxy, nitro, cyano, —$NR^AR^B$, —$C_{1-2}$alkyl-O—$C_{1-2}$alkyl, phenyl, substituted phenyl and 5 to 6 membered heteroaryl; wherein $R^A$ and $R^B$ are each independently selected form the group consisting of H and methyl; wherein the substituted phenyl is substituted with one to two substituents independently selected from the group consisting of halo, $C_{1-2}$alkyl, $C_{1-2}$alkoxy, cyano, —$NR^CR^D$, —C(O)—$NR^CR^D$, —C(O)OH, —C(O)O—$C_{1-2}$alkyl, (—C(O)-4-morpholinyl), (—C(O)-1-pyrrolidinyl) and (—$NR^E$—C(O)—$C_{1-4}$alkyl); wherein $R^C$ and $R^D$ are each independently selected from the group consisting of H and $C_{1-2}$alkyl; and wherein $R^E$ is selected from the group consisting of H and $C_{1-2}$alkyl.

In an embodiment of the present invention, $R^A$ is selected from the group consisting of H and methyl. In an embodiment of the present invention, $R^B$ is selected from the group consisting of H and methyl. In another embodiment of the present invention $R^A$ and $R^B$ are the same and are selected from the group consisting of H and methyl.

In an embodiment of the present invention, $R^C$ is selected from the group consisting of H and methyl. In an embodiment of the present invention, $R^B$ is selected from the group consisting of H and methyl. In another embodiment of the present invention $R^C$ and $R^D$ are the same and are selected from the group consisting of H and methyl.

In an embodiment of the present invention, $R^E$ is selected from the group consisting of H and methyl.

In another embodiment of the present invention, $R^1$ is selected from the group consisting of phenyl, 3-chloro-4-fluoro-phenyl, 3-fluoro-4-methyl-phenyl, 2-methylphenyl, 3-methylphenyl, 4-methylphenyl, 2-hydroxyphenyl, 3-hydroxyphenyl, 2,4-difluorophenyl, 3,5-difluorophenyl, 3,4-difluorophenyl, 3,4-dichlorophenyl, 2,3-dichlorophenyl, 3-chloro-4-methyl-phenyl, 3-trifluoromethylphenyl, 3,5-dimethylphenyl, 3-dimethylamino-phenyl, 3-(methoxymethyl)-phenyl, 3-fluorophenyl, 4-fluorophenyl, 3-chlorophenyl, 4-chlorophenyl, 4-bromophenyl, 3,4,5-trifluorophenyl, 4-aminophenyl, 3-(3-furyl)-phenyl, 3-bromo-4-amino-phenyl, 3-cyanophenyl, 4-nitrophenyl, 3-methyl-4-fluoro-phenyl, 2-chloro-4-fluoro-phenyl, 1-methyl-3-fluoro-phenyl, 1-naphthyl, 2-naphthyl, 3-biphenyl, 4-biphenyl, 3-(4'-fluoro-biphenyl), 3-(4'-methoxy-biphenyl) 3-(4'-chloro-biphenyl), 3-(4'-cyano-biphenyl), 3-(4'-(aminocarbonyl)-biphenyl), 3-(4'-(ethoxycarbonyl)-biphenyl), 3-(4'-dimethylamino-biphenyl), 3-(4'-carboxy-biphenyl), 3-(4'-(1-pyrrolidinyl-carbonyl)-biphenyl), 3-(4'-(4-morpholinyl-carbonyl)-biphenyl), 3-(4'-methyl-biphenyl), 3-(3'-chloro-4'-fluoro-biphenyl), 2-(2',3'-dichloro-biphenyl), 3-(6-amino-biphenyl), 3-(4'-(methylcarbonylamino)-biphenyl), 3-(6-methyl-biphenyl), 2-furyl, 2-(5-methyl-furyl), 3-(2-trifluoromethyl-5-methyl-furyl), 3-furyl, 2-thienyl, 3-thienyl, 3-(4-methyl-thienyl), 3-(2-chloro-5-(4-fluorophenyl)-thienyl), 3-(2-chloro-thienyl), 3-(2-methyl-thienyl), 2-(4-chloro-thienyl), 2-(3-chloro-thienyl), 2-(5-chloro-thienyl), 2-(4-bromo-thienyl), 2-(3-bromo-thienyl), 2-(5-bromo-thienyl), 3-(2-hydroxymethylthienyl), 2-(3-methyl-thienyl), 2-(4-methyl-thienyl), 3-(4-methoxy-thienyl), 2-(5-phenyl-thienyl), 2-(2,5-dichlorothienyl), 3-(2,5-dichlorothienyl), 3-(2-chloro-5-bromo-thienyl), 3-(2-aminomethyl-thienyl), 2-(5-cyano-thienyl), 3-(2-cyano-thienyl), 3-(5-hydroxymethyl-thienyl), 3-(5-cyano-thienyl), 3-(5-vinyl-thienyl), 3-(5-ethyl-thienyl), 3-(5-isopropyl-thienyl), 3-(2-methyl-5-chloro-thienyl), 3-(2-vinyl-thienyl), 2-(3-methyl-5-chloro-thienyl), 2-(5-(2-thienyl)-thienyl), 2-(4,5-dichloro-thienyl), 2-(5-(2-pyridyl)-thienyl), 4-dibenzofuryl, 2-pyridyl, 3-pyridyl, 4-pyridyl, 3-(6-chloro-pyridyl), 3-(2-chloro-pyridyl), 5-(1-methyl-indolyl), 2-benzofuryl, 2-benzothienyl and 3-benzothienyl.

In another embodiment of the present invention, $R^1$ is selected from the group consisting of phenyl, 3-chloro-4-fluoro-phenyl, 3-fluoro-4-methyl-phenyl, 2-methylphenyl, 4-methylphenyl, 2-hydroxyphenyl, 2,4-difluorophenyl, 3,5-difluorophenyl, 3,4-difluorophenyl, 3,4-dichlorophenyl, 2,3-dichlorophenyl, 3-trifluoromethylphenyl, 3-dimethylamino-phenyl, 3-fluorophenyl, 4-fluorophenyl, 3-chlorophenyl, 4-chlorophenyl, 4-bromophenyl, 3,4,5-trifluorophenyl, 4-aminophenyl, 3-(3-furyl)-phenyl, 4-nitrophenyl, 3-methyl-4-fluoro-phenyl, 2-chloro-4-fluoro-phenyl, 1-methyl-3-fluoro-phenyl, 3-biphenyl, 3-(4'-fluoro-biphenyl), 3-(4'-methoxy-biphenyl), 3-(4'-chloro-biphenyl), 3-(4'-cyano-biphenyl), 3-(4'-(aminocarbonyl)-biphenyl), 3-(4'-(ethoxycarbonyl)-biphenyl), 3-(4'-dimethylamino-biphenyl), 3-(4'-(1-pyrrolidinyl-carbonyl)-biphenyl), 3-(3'-chloro-4'-fluoro-biphenyl), 2-furyl, 3-furyl, 2-thienyl, 3-thienyl, 3-(4-methyl-thienyl), 3-(2-chloro-5-(4-fluorophenyl)-thienyl), 3-(2-chloro-thienyl), 3-(2-methyl-thienyl), 2-(4-chloro-thienyl), 2-(3-chloro-thienyl), 2-(5-chloro-thienyl), 2-(3-bromo-thienyl), 2-(4-bromo-thienyl), 2-(5-bromo-thienyl), 2-(3-methyl-thienyl), 2-(2,5-dichlorothienyl), 3-(2,5-dichlorothienyl), 3-(2-chloro-5-bromo-thienyl), 3-(2-cyano-thienyl), 3-(5-vinyl-thienyl), 3-(5-ethyl-thienyl), 3-(5-isopropyl-thienyl), 3-(2-methyl-5-chloro-thienyl), 3-(2-vinyl-thienyl), 2-(3-methyl-5-chloro-thienyl), 3-pyridyl, 3-(6-chloro-pyridyl), 3-(2-chloro-pyridyl), 2-benzofuryl and 3-benzothienyl.

In another embodiment of the present invention, $R^1$ is selected from the group consisting of 3-chloro-4-fluoro-phenyl, 3-fluoro-4-methyl-phenyl, 4-methylphenyl, 2,4-difluorophenyl, 3,5-difluorophenyl, 3,4-difluorophenyl, 3,4-dichlorophenyl, 3-trifluoromethylphenyl, 3-fluorophenyl, 4-fluorophenyl, 4-chlorophenyl, 4-bromophenyl, 3,4,5-trifluorophenyl, 2-chloro-4-fluoro-phenyl, 1-methyl-3-fluoro-phenyl, 3-biphenyl, 3-(4'-fluoro-biphenyl), 3-(4'-methoxy-biphenyl), 3-(4'-chloro-biphenyl), 3-(4'-cyano-biphenyl), 3-(4'-(aminocarbonyl)-biphenyl), 2-furyl, 3-furyl, 2-thienyl, 3-thienyl, 3-(4-methyl-thienyl), 3-(2-chloro-thienyl), 3-(2-methyl-thienyl), 2-(3-chloro-thienyl), 2-(5-chloro-thienyl), 2-(3-bromo-thienyl), 2-(4-bromo-thienyl), 2-(5-bromo-thienyl), 2-(3-methyl-thienyl), 3-(5-isopropyl-thienyl) and 3-(2-chloro-pyridyl).

In another embodiment of the present invention, $R^1$ is selected from the group consisting of 3-fluoro-4-methyl-phenyl, 3,5-difluorophenyl, 3,4-difluorophenyl, 3,4-dichlorophenyl, 4-fluorophenyl, 4-chlorophenyl, 4-bromophenyl, 3,4,5-trifluorophenyl, 1-methyl-3-fluoro-phenyl, 3-(4'-fluoro-biphenyl), 3-(4'-cyano-biphenyl), 3-(4'-(aminocarbonyl)-biphenyl), 3-furyl, 3-thienyl, 3-(2-chloro-thienyl), 2-(3-chloro-thienyl), 2-(5-chloro-thienyl), 2-(3-bromo-thienyl), 2-(4-bromo-thienyl) and 2-(5-bromo-thienyl).

In another embodiment of the present invention, $R^1$ is selected from the group consisting of 4-chlorophenyl, 3,4,5-trifluorophenyl, 3-(4'-fluoro-biphenyl), 3-(4'-cyano-biphenyl), 2-(3-chloro-thienyl) and 2-(3-bromo-thienyl).

In another embodiment of the present invention, $R^1$ is selected form the group consisting of phenyl, 3-fluoro-4-methyl-phenyl, 4-methylphenyl, 3,4-difluorophenyl, 3-fluorophenyl, 3-trifluoromethylphenyl, 4-bromophenyl, 3,4,5-trifluorophenyl, 4-fluorophenyl, 4-chlorophenyl, 3,4-dichlorophenyl, 3-cyanophenyl, 3-methyl-4-fluoro-phenyl, 4-nitrophenyl, 2,4-difluorophenyl, 3,5-difluorophenyl, 2-chloro-4-fluoro-phenyl, 1-methyl-3-fluoro-phenyl, 1-naphthyl, 2-naphthyl, 3-biphenyl, 4-biphenyl, 3-furyl, 3-(2-trifluoromethyl-5-methyl-furyl), 3-thienyl, 2-thienyl, 2-(4-bromo-thienyl), 2-(3-bromo-thienyl), 2-(3-chloro-thienyl), 2-(5-bromo-thienyl), 2-(5-chloro-thienyl), 3-(4-methoxy-thienyl), 2-(5-(2-pyridyl)-thienyl), 2-(3-methyl-thienyl), 2-(2,5-dichlorothienyl), 2-(4-chloro-thienyl), 2-pyridyl, 3-pyridyl, 4-pyridyl, 3-(6-chloro-pyridyl), 3-(2-chloro-pyridyl), 2-benzothienyl and 3-benzothienyl.

In another embodiment of the present invention, $R^1$ is selected from the group consisting of 3-fluoro-4-methyl-phenyl, 3,5-difluorophenyl, 3,4-difluorophenyl, 3,4-dichlorophenyl, 4-fluorophenyl, 4-chlorophenyl, 4-bromophenyl, 3,4,5-trifluorophenyl, 1-methyl-3-fluoro-phenyl, 3-thienyl, 2-(3-chloro-thienyl), 2-(3-bromo-thienyl), 2-(4-bromo-thienyl) and 2-(5-bromo-thienyl).

In another embodiment of the present invention, $R^1$ is selected from the group consisting of phenyl, 3-chloro-4-fluoro-phenyl, 3-fluoro-4-methyl-phenyl, 2-methylphenyl, 3-methylphenyl, 4-methylphenyl, 2-hydroxyphenyl, 3-hydroxyphenyl, 3,4-difluorophenyl, 2,3-dichlorophenyl, 3,4-dichlorophenyl, 3-chloro-4-methyl-phenyl, 3-trifluoromethylphenyl, 3,5-dimethylphenyl, 3-dimethylamino-phenyl, 3-(methoxymethyl)-phenyl, 3-chlorophenyl, 4-aminophenyl, 3-(3-furyl)-phenyl, 3-bromo-4-amino-phenyl, 1-naphthyl, 2-naphthyl, 3-biphenyl, 4-biphenyl, 3-(4'-fluoro-biphenyl), 3-(4'-methoxy-biphenyl) 3-(4'-chloro-biphenyl), 3-(4'-cyano-biphenyl), 3-(4'-(aminocarbonyl)-biphenyl), 3-(4'-(ethoxycarbonyl)-biphenyl), 3-(4'-dimethylamino-biphenyl), 3-(4'-carboxy-biphenyl), 3-(4'-(1-pyrrolidinyl-carbonyl)-biphenyl), 3-(4'-(4-morpholinyl-carbonyl)-biphenyl), 3-(4'-methyl-biphenyl), 3-(3'-chloro-4'-fluoro-biphenyl), 2-(2',3'-dichloro-biphenyl), 3-(6-amino-biphenyl), 3-(4'-(methylcarbonylamino)-biphenyl), 3-(6-methyl-biphenyl), 2-furyl, 2-(5-methyl-furyl), 3-furyl, 2-thienyl, 3-thienyl, 3-(4-methyl-thienyl), 3-(2-chloro-5-(4-fluorophenyl)-thienyl), 3-(2-chloro-thienyl), 3-(2-methyl-thienyl), 2-(4-chloro-thienyl), 2-(5-chloro-thienyl), 2-(5-bromo-thienyl), 3-(2-hydroxymethyl-thienyl), 2-(4-methyl-thienyl), 2-(5-phenyl-thienyl), 3-(2,5-dichlorothienyl), 3-(2-chloro-5-bromo-thienyl), 3-(2-aminomethyl-thienyl), 2-(5-cyano-thienyl), 3-(2-cyano-thienyl), 3-(5-hydroxymethyl-thienyl), 3-(5-cyano-thienyl), 3-(5-vinyl-thienyl), 3-(5-ethyl-thienyl), 3-(5-isopropyl-thienyl), 3-(2-methyl-5-chloro-thienyl), 3-(2-vinyl-thienyl), 2-(3-methyl-5-chloro-thienyl), 2-(5-(2-thienyl)-thienyl), 2-(4,5-dichloro-thienyl), 2-(3-chloro-thienyl), 4-dibenzofuryl, 3-pyridyl, 5-(1-methyl-indolyl), 2-benzofuryl and 3-benzothienyl.

In another embodiment of the present invention, $R^1$ is selected from the group consisting of 3-(4'-fluoro-biphenyl), 3-(4'-cyano-biphenyl), 3-(4'-(aminocarbonyl)-biphenyl), 3-furyl, 3-(2-chloro-thienyl) and 2-(5-chloro-thienyl).

In an embodiment of the present invention, a is 1. In another embodiment of the present invention, a is 2.

In an embodiment of the present invention, $R^2$ is selected from the group consisting of H and $C_{1-2}$ alkyl. In another embodiment of the present invention, $R^2$ is selected from the group consisting of H and methyl. In another embodiment of the present invention, $R^2$ is methyl.

In an embodiment, the present invention is directed to one or more compounds of formula (I) selected from the group consisting of:

2-(4-Methyl-piperazin-1-yl)-4-thiophen-3-yl-[1,3,5]triazine;
2-(4-Methyl-piperazin-1-yl)-4-thiophen-2-yl-[1,3,5]triazine;
2-(3-Fluoro-4-methyl-phenyl)-4-(4-methyl-piperazin-1-yl)-[1,3,5]triazine;
2-(4-Methyl-piperazin-1-yl)-4-p-tolyl-[1,3,5]triazine;
2-(3,4-Difluoro-phenyl)-4-(4-methyl-piperazin-1-yl)-[1,3,5]triazine;
2-Furan-3-yl-4-(4-methyl-piperazin-1-yl)-[1,3,5]triazine;
2-(3-Fluoro-phenyl)-4-(4-methyl-piperazin-1-yl)-[1,3,5]triazine;
2-(4-Methyl-piperazin-1-yl)-4-(3-trifluoromethyl-phenyl)-[1,3,5]triazine;
(2-(4-Bromo-thiophen-2-yl)-4-(4-methyl-piperazin-1-yl)-[1,3,5]triazine;
2-(4-Bromo-phenyl)-4-(4-methyl-piperazin-1-yl)-[1,3,5]triazine;
2-(4-Methyl-piperazin-1-yl)-4-(3,4,5-trifluoro-phenyl)-[1,3,5]triazine;
2-(4-Fluoro-phenyl)-4-(4-methyl-piperazin-1-yl)-[1,3,5]triazine;
2-(4-Chloro-phenyl)-4-(4-methyl-piperazin-1-yl)-[1,3,5]triazine;
2-(3,4-Dichloro-phenyl)-4-(4-methyl-piperazin-1-yl)-[1,3,5]triazine;
2-(3-Bromo-thiophen-2-yl)-4-(4-methyl-piperazin-1-yl)-[1,3,5]triazine;
2-(6-Chloro-pyridin-3-yl)-4-(4-methyl-piperazin-1-yl)-[1,3,5]triazine;
2-(3-Chloro-thiophen-2-yl)-4-(4-methyl-piperazin-1-yl)-[1,3,5]triazine;
2-(5-Bromo-thiophen-2-yl)-4-(4-methyl-piperazin-1-yl)-[1,3,5]triazine;
2-(4-Methyl-piperazin-1-yl)-4-pyridin-3-yl-[1,3,5]triazine;
2-(4-Methyl-piperazin-1-yl)-4-pyridin-4-yl-[1,3,5]triazine;
2-Benzo[b]thiophen-2-yl-4-(4-methyl-piperazin-1-yl)-[1,3,5]triazine;
2-(4-Methyl-piperazin-1-yl)-4-(5-methyl-2-trifluoromethyl-furan-3-yl)-[1,3,5]triazine;
2-(3-Bromo-thiophen-2-yl)-4-methyl-6-(4-methyl-piperazin-1-yl)-[1,3,5]triazine;
1-[4-(3-Bromo-thiophen-2-yl)-[1,3,5]triazin-2-yl]-4-methyl-[1,4]diazepane;
2-(5-Chloro-thiophen-2-yl)-4-(4-methyl-piperazin-1-yl)-[1,3,5]triazine;
1-Methyl-4-(2-thiophen-3-yl-pyridin-4-yl)-piperazine;
1-(2-Furan-2-yl-pyridin-4-yl)-4-methyl-piperazine;
1-(2-Furan-3-yl-pyridin-4-yl)-4-methyl-piperazine;
1-Methyl-4-[2-(4-methyl-thiophen-3-yl)-pyridin-4-yl]-piperazine;
1-[2-(3-Chloro-4-fluoro-phenyl)-pyridin-4-yl]-4-methyl-piperazine;
1-[2-(3-Fluoro-4-methyl-phenyl)-pyridin-4-yl]-4-methyl-piperazine;
1-Methyl-4-(2-p-tolyl-pyridin-4-yl)-piperazine;
3-[4-(4-Methyl-piperazin-1-yl)-pyridin-2-yl]-phenol;
1-[2-(3,4-Difluoro-phenyl)-pyridin-4-yl]-4-methyl-piperazine;
1-[2-(2,3-Dichloro-phenyl)-pyridin-4-yl]-4-methyl-piperazine;
1-[2-(2,3-Dichloro-phenyl)-pyridin-4-yl]-4-methyl-piperazine;
1-[2-(3-Chloro-4-methyl-phenyl)-pyridin-4-yl]-4-methyl-piperazine;
1-(2-Biphenyl-3-yl-pyridin-4-yl)-4-methyl-piperazine;
1-Methyl-4-(2-thiophen-3-yl-pyridin-4-yl)-[1,4]diazepane;
Methyl-(1-methyl-pyrrolidin-3-yl)-(2-thiophen-3-yl-pyridin-4-yl)-amine;
N,N,N'-Trimethyl-N'-(2-thiophen-3-yl-pyridin-4-yl)-ethane-1,2-diamine;
Dimethyl-[1-(2-thiophen-3-yl-pyridin-4-yl)-pyrrolidin-3-yl]-amine;
1-Methyl-4-(4-thiophen-2-yl-pyridin-2-yl)-piperazine;
1-{2-[2-Chloro-5-(4-fluoro-phenyl)-thiophen-3-yl]-pyridin-4-yl}-4-methyl-piperazine;
1-(2-Dibenzofuran-4-yl-pyridin-4-yl)-4-methyl-piperazine;
1-Methyl-5-[4-(4-methyl-piperazin-1-yl)-pyridin-2-yl]-1H-indole;
1-[2-(2-Chloro-thiophen-3-yl)-pyridin-4-yl]-4-methyl-piperazine;
1-Methyl-4-[2-(2-methyl-thiophen-3-yl)-pyridin-4-yl]-piperazine;
1-[2-(4-Chloro-thiophen-2-yl)-pyridin-4-yl]-4-methyl-piperazine;
1-Methyl-4-(2-thiophen-2-yl-pyridin-4-yl)-piperazine;
1-[2-(5-Chloro-thiophen-2-yl)-pyridin-4-yl]-4-methyl-piperazine;
1-[2-(5-Bromo-thiophen-2-yl)-pyridin-4-yl]-4-methyl-piperazine;
1-[2-(4'-Fluoro-biphenyl-3-yl)-pyridin-4-yl]-4-methyl-piperazine;
1-[2-(4'-Methoxy-biphenyl-3-yl)-pyridin-4-yl]-4-methyl-piperazine;
1-[2-(4'-Chloro-biphenyl-3-yl)-pyridin-4-yl]-4-methyl-piperazine;
3'-[4-(4-Methyl-piperazin-1-yl)-pyridin-2-yl]-biphenyl-4-carbonitrile;
3'-[4-(4-Methyl-piperazin-1-yl)-pyridin-2-yl]-biphenyl-4-carboxylic acid amide;
3'-[4-(4-Methyl-piperazin-1-yl)-pyridin-2-yl]-biphenyl-4-carboxylic acid ethyl ester;
Dimethyl-{3'-[4-(4-methyl-piperazin-1-yl)-pyridin-2-yl]-biphenyl-4-yl}-amine;
4-(4-Methyl-piperazin-1-yl)-2-thiophen-2-yl-pyrimidine;
{3-[4-(4-Methyl-piperazin-1-yl)-pyridin-2-yl]-thiophen-2-yl}-methanol;
3'-[4-(4-Methyl-piperazin-1-yl)-pyridin-2-yl]-biphenyl-4-carboxylic acid;
{3'-[4-(4-Methyl-piperazin-1-yl)-pyridin-2-yl]-biphenyl-4-yl}-morpholin-4-yl-methanone;
{3'-[4-(4-Methyl-piperazin-1-yl)-pyridin-2-yl]-biphenyl-4-yl}-pyrrolidin-1-yl-methanone;
Methyl-[1-(2-thiophen-3-yl-pyridin-4-yl)-pyrrolidin-3-yl]-amine;
4-(4-Methyl-piperazin-1-yl)-6-thiophen-2-yl-pyrimidine;
4-piperazin-1-yl-6-thiophen-2-yl-pyrimidine;
1-Methyl-4-(6-thiophen-2-yl-pyrimidin-4-yl)-[1,4]diazepane;
2-piperazin-1-yl-4-thiophen-2-yl-pyrimidine;
4-(4-Methyl-piperazin-1-yl)-2-phenyl-pyrimidine;
2-(3-Chloro-4-fluoro-phenyl)-4-(4-methyl-piperazin-1-yl)-pyrimidine;
2-(3-Fluoro-phenyl)-4-(4-methyl-piperazin-1-yl)-pyrimidine;
1-(4-Thiophen-2-yl-pyrimidin-2-yl)-[1,4]diazepane;
1-Methyl-4-(6-thiophen-2-yl-pyridin-2-yl)-piperazine;
1-Methyl-4-(5-thiophen-2-yl-pyridin-3-yl)-piperazine;
4-Methyl-2-(4-methyl-piperazin-1-yl)-6-thiophen-2-yl-pyrimidine;

1-Methyl-4-[2-(3-trifluoromethyl-phenyl)-pyridin-4-yl]-piperazine;
1-Methyl-4-(2-o-tolyl-pyridin-4-yl)-piperazine;
4-(4-Methyl-piperazin-1-yl)-[2,3']bipyridinyl;
1-[2-(3,5-Dimethyl-phenyl)-pyridin-4-yl]-4-methyl-piperazine;
Dimethyl-{3-[4-(4-methyl-piperazin-1-yl)-pyridin-2-yl]-phenyl}-amine;
1-[2-(3-Methoxymethyl-phenyl)-pyridin-4-yl]-4-methyl-piperazine;
2-[4-(4-Methyl-piperazin-1-yl)-pyridin-2-yl]-phenol;
1-Methyl-4-[2-(4-methyl-thiophen-2-yl)-pyridin-4-yl]-piperazine;
1-(2-Benzofuran-2-yl-pyridin-4-yl)-4-methyl-piperazine;
1-(2-Benzo[b]thiophen-3-yl-pyridin-4-yl)-4-methyl-piperazine;
1-[2-(3-Chloro-phenyl)-pyridin-4-yl]-4-methyl-piperazine;
1-Methyl-4-(2-naphthalen-1-yl-pyridin-4-yl)-piperazine;
1-Methyl-4-(2-naphthalen-2-yl-pyridin-4-yl)-piperazine;
1-Methyl-4-(2-m-tolyl-pyridin-4-yl)-piperazine;
1-(2-Biphenyl-4-yl-pyridin-4-yl)-4-methyl-piperazine;
4-[4-(4-Methyl-piperazin-1-yl)-pyridin-2-yl]-phenylamine;
1-Methyl-4-(2-methyl-6-thiophen-2-yl-pyridin-4-yl)-piperazine;
1-[4-(3-Fluoro-4-methyl-phenyl)-pyridin-2-yl]-4-methyl-piperazine;
1-(4-Biphenyl-3-yl-pyridin-2-yl)-4-methyl-piperazine;
2-(3-Fluoro-4-methyl-phenyl)-4-(4-methyl-piperazin-1-yl)-pyrimidine;
2-Biphenyl-3-yl-4-(4-methyl-piperazin-1-yl)-pyrimidine;
4-(4-Methyl-piperazin-1-yl)-2-thiophen-3-yl-pyrimidine;
1-Methyl-4-(4-thiophen-3-yl-pyridin-2-yl)-piperazine;
1-Methyl-4-[2-(5-phenyl-thiophen-2-yl)-pyridin-4-yl]-piperazine;
1-Methyl-4-[2-(4'-methyl-biphenyl-3-yl)-pyridin-4-yl]-piperazine;
1-[2-(3'-Chloro-4'-fluoro-biphenyl-3-yl)-pyridin-4-yl]-4-methyl-piperazine;
1-[2-(2',3'-Dichloro-biphenyl-3-yl)-pyridin-4-yl]-4-methyl-piperazine;
2-Biphenyl-3-yl-4-(4-methyl-piperazin-1-yl)-[1,3,5]triazine;
1-[2-(2,5-Dichloro-thiophen-3-yl)-pyridin-4-yl]-4-methyl-piperazine;
1-[2-(5-Bromo-2-chloro-thiophen-3-yl)-pyridin-4-yl]-4-methyl-piperazine;
3-[4-(4-Methyl-piperazin-1-yl)-[1,3,5]triazin-2-yl]-benzonitrile;
2-(4-Methyl-piperazin-1-yl)-4-naphthalen-1-yl-[1,3,5]triazine;
C-{3-[4-(4-Methyl-piperazin-1-yl)-pyridin-2-yl]-thiophen-2-yl}-methylamine;
1-[2-(3-Furan-3-yl-phenyl)-pyridin-4-yl]-4-methyl-piperazine;
2-(4-Fluoro-3-methyl-phenyl)-4-(4-methyl-piperazin-1-yl)-[1,3,5]triazine;
2-Biphenyl-4-yl-4-(4-methyl-piperazin-1-yl)-[1,3,5]triazine;
2-(4-Methyl-piperazin-1-yl)-4-naphthalen-2-yl-[1,3,5]triazine;
2-(4-Methyl-piperazin-1-yl)-4-phenyl-[1,3,5]triazine;
2-(2-Chloro-pyridin-3-yl)-4-(4-methyl-piperazin-1-yl)-[1,3,5]triazine;
2-Bromo-4-[4-(4-methyl-piperazin-1-yl)-pyridin-2-yl]-phenylamine;
2-(4-Methyl-piperazin-1-yl)-4-(4-nitro-phenyl)-[1,3,5]triazine;
2-(2,4-Difluoro-phenyl)-4-(4-methyl-piperazin-1-yl)-[1,3,5]triazine;
2-(5-Fluoro-2-methyl-phenyl)-4-(4-methyl-piperazin-1-yl)-[1,3,5]triazine;
5-[4-(4-Methyl-piperazin-1-yl)-pyridin-2-yl]-biphenyl-2-ylamine;
N-{3'-[4-(4-Methyl-piperazin-1-yl)-pyridin-2-yl]-biphenyl-4-yl}-acetamide;
5-[4-(4-Methyl-piperazin-1-yl)-pyridin-2-yl]-thiophene-2-carbonitrile;
1-Methyl-4-[2-(6-methyl-biphenyl-3-yl)-pyridin-4-yl]-piperazine;
1-Methyl-4-(2-phenyl-pyridin-4-yl)-piperazine;
3-[4-(4-Methyl-piperazin-1-yl)-pyridin-2-yl]-thiophene-2-carbonitrile;
2-(4-Methoxy-thiophen-3-yl)-4-(4-methyl-piperazin-1-yl)-[1,3,5]triazine;
2-(4-Methyl-piperazin-1-yl)-4-(5-pyridin-2-yl-thiophen-2-yl)-[1,3,5]triazine;
{4-[4-(4-Methyl-piperazin-1-yl)-pyridin-2-yl]-thiophen-2-yl}-methanol;
4-[4-(4-Methyl-piperazin-1-yl)-pyridin-2-yl]-thiophene-2-carbonitrile;
1-Methyl-4-[2-(5-vinyl-thiophen-3-yl)-pyridin-4-yl]-piperazine;
1-[2-(5-Ethyl-thiophen-3-yl)-pyridin-4-yl]-4-methyl-piperazine;
1-[2-(5-Isopropenyl-thiophen-3-yl)-pyridin-4-yl]-4-methyl-piperazine;
2-(3,5-Difluoro-phenyl)-4-(4-methyl-piperazin-1-yl)-[1,3,5]triazine;
2-(2-Chloro-4-fluoro-phenyl)-4-(4-methyl-piperazin-1-yl)-[1,3,5]triazine;
2-(4-Methyl-piperazin-1-yl)-4-pyridin-2-yl-[1,3,5]triazine;
2-(4-Methyl-piperazin-1-yl)-4-(3-methyl-thiophen-2-yl)-[1,3,5]triazine;
1-[2-(5-Chloro-2-methyl-thiophen-3-yl)-pyridin-4-yl]-4-methyl-piperazine;
1-Methyl-4-[2-(5-methyl-furan-2-yl)-pyridin-4-yl]-piperazine;
2-(2,5-Dichloro-thiophen-3-yl)-4-(4-methyl-piperazin-1-yl)-[1,3,5]triazine;
2-Benzo[b]thiophen-3-yl-4-(4-methyl-piperazin-1-yl)-[1,3,5]triazine;
1-Methyl-4-[2-(2-vinyl-thiophen-3-yl)-pyridin-4-yl]-piperazine;
1-Methyl-4-(3-methyl-2-thiophen-3-yl-pyridin-4-yl)-piperazine;
2-Methyl-4-(4-methyl-piperazin-1-yl)-6-(3,4,5-trifluoro-phenyl)-[1,3,5]triazine;
1-[2-(5-Chloro-3-methyl-thiophen-2-yl)-pyridin-4-yl]-4-methyl-piperazine;
1-(2-[2,2']Bithiophenyl-5-yl-pyridin-4-yl)-4-methyl-piperazine;
1-[2-(4,5-Dichloro-thiophen-2-yl)-pyridin-4-yl]-4-methyl-piperazine;
2-(4-Chloro-thiophen-2-yl)-4-(4-methyl-piperazin-1-yl)-[1,3,5]triazine;
1-[2-(3-Chloro-thiophen-2-yl)-pyridin-4-yl]-4-methyl-piperazine;
4-(4-Chloro-thiophen-2-yl)-2-(4-methyl-piperazin-1-yl)-pyrimidine;
2-Chloro-4-(3-chloro-thiophen-2-yl)-6-(4-methyl-piperazin-1-yl)-pyrimidine;
2-Chloro-4-(4-methyl-piperazin-1-yl)-6-thiophen-2-yl-pyrimidine;

and pharmaceutically acceptable salts, prodrugs and active metabolites thereof.

In another embodiment, the present invention is directed to one or more compounds selected from the group consisting of
2-(4-Methyl-piperazin-1-yl)-4-thiophen-3-yl-[1,3,5]triazine;
2-(4-Methyl-piperazin-1-yl)-4-thiophen-2-yl-[1,3,5]triazine;
2-(3-Fluoro-4-methyl-phenyl)-4-(4-methyl-piperazin-1-yl)-[1,3,5]triazine;
2-(4-Methyl-piperazin-1-yl)-4-p-tolyl-[1,3,5]triazine;
2-(3,4-Difluoro-phenyl)-4-(4-methyl-piperazin-1-yl)-[1,3,5]triazine;
2-Furan-3-yl-4-(4-methyl-piperazin-1-yl)-[1,3,5]triazine;
2-(3-Fluoro-phenyl)-4-(4-methyl-piperazin-1-yl)-[1,3,5]triazine;
2-(4-Methyl-piperazin-1-yl)-4-(3-trifluoromethyl-phenyl)-[1,3,5]triazine;
(2-(4-Bromo-thiophen-2-yl)-4-(4-methyl-piperazin-1-yl)-[1,3,5]triazine;
2-(4-Bromo-phenyl)-4-(4-methyl-piperazin-1-yl)-[1,3,5]triazine;
2-(4-Methyl-piperazin-1-yl)-4-(3,4,5-trifluoro-phenyl)-[1,3,5]triazine;
2-(4-Fluoro-phenyl)-4-(4-methyl-piperazin-1-yl)-[1,3,5]triazine;
2-(4-Chloro-phenyl)-4-(4-methyl-piperazin-1-yl)-[1,3,5]triazine;
2-(3,4-Dichloro-phenyl)-4-(4-methyl-piperazin-1-yl)-[1,3,5]triazine;
2-(3-Bromo-thiophen-2-yl)-4-(4-methyl-piperazin-1-yl)-[1,3,5]triazine;
2-(6-Chloro-pyridin-3-yl)-4-(4-methyl-piperazin-1-yl)-[1,3,5]triazine;
2-(3-Chloro-thiophen-2-yl)-4-(4-methyl-piperazin-1-yl)-[1,3,5]triazine;
2-(5-Bromo-thiophen-2-yl)-4-(4-methyl-piperazin-1-yl)-[1,3,5]triazine;
2-(4-Methyl-piperazin-1-yl)-4-pyridin-3-yl-[1,3,5]triazine;
2-(4-Methyl-piperazin-1-yl)-4-pyridin-4-yl-[1,3,5]triazine;
2-Benzo[b]thiophen-2-yl-4-(4-methyl-piperazin-1-yl)-[1,3,5]triazine;
2-(4-Methyl-piperazin-1-yl)-4-(5-methyl-2-trifluoromethyl-furan-3-yl)-[1,3,5]triazine;
2-(3-Bromo-thiophen-2-yl)-4-methyl-6-(4-methyl-piperazin-1-yl)-[1,3,5]triazine;
1-[4-(3-Bromo-thiophen-2-yl)-[1,3,5]triazin-2-yl]-4-methyl-[1,4]diazepane;
2-(5-Chloro-thiophen-2-yl)-4-(4-methyl-piperazin-1-yl)-[1,3,5]triazine;
1-Methyl-4-(2-thiophen-3-yl-pyridin-4-yl)-piperazine;
1-(2-Furan-2-yl-pyridin-4-yl)-4-methyl-piperazine;
1-(2-Furan-3-yl-pyridin-4-yl)-4-methyl-piperazine;
1-Methyl-4-[2-(4-methyl-thiophen-3-yl)-pyridin-4-yl]-piperazine;
1-[2-(3-Chloro-4-fluoro-phenyl)-pyridin-4-yl]-4-methyl-piperazine;
1-[2-(3-Fluoro-4-methyl-phenyl)-pyridin-4-yl]-4-methyl-piperazine;
1-Methyl-4-(2-p-tolyl-pyridin-4-yl)-piperazine;
3-[4-(4-Methyl-piperazin-1-yl)-pyridin-2-yl]-phenol;
1-[2-(3,4-Difluoro-phenyl)-pyridin-4-yl]-4-methyl-piperazine;
1-[2-(2,3-Dichloro-phenyl)-pyridin-4-yl]-4-methyl-piperazine;
1-[2-(2,3-Dichloro-phenyl)-pyridin-4-yl]-4-methyl-piperazine;
1-[2-(3-Chloro-4-methyl-phenyl)-pyridin-4-yl]-4-methyl-piperazine;
1-(2-Biphenyl-3-yl-pyridin-4-yl)-4-methyl-piperazine;
1-Methyl-4-(2-thiophen-3-yl-pyridin-4-yl)-[1,4]diazepane;
1-{2-[2-Chloro-5-(4-fluoro-phenyl)-thiophen-3-yl]-pyridin-4-yl}-4-methyl-piperazine;
1-(2-Dibenzofuran-4-yl-pyridin-4-yl)-4-methyl-piperazine;
1-Methyl-5-[4-(4-methyl-piperazin-1-yl)-pyridin-2-yl]-1H-indole;
1-[2-(2-Chloro-thiophen-3-yl)-pyridin-4-yl]-4-methyl-piperazine;
1-Methyl-4-[2-(2-methyl-thiophen-3-yl)-pyridin-4-yl]-piperazine;
1-[2-(4-Chloro-thiophen-2-yl)-pyridin-4-yl]-4-methyl-piperazine;
1-Methyl-4-(2-thiophen-2-yl-pyridin-4-yl)-piperazine;
1-[2-(5-Chloro-thiophen-2-yl)-pyridin-4-yl]-4-methyl-piperazine;
1-[2-(5-Bromo-thiophen-2-yl)-pyridin-4-yl]-4-methyl-piperazine;
1-[2-(4'-Fluoro-biphenyl-3-yl)-pyridin-4-yl]-4-methyl-piperazine;
1-[2-(4'-Methoxy-biphenyl-3-yl)-pyridin-4-yl]-4-methyl-piperazine;
1-[2-(4'-Chloro-biphenyl-3-yl)-pyridin-4-yl]-4-methyl-piperazine;
3'-[4-(4-Methyl-piperazin-1-yl)-pyridin-2-yl]-biphenyl-4-carbonitrile;
3'-[4-(4-Methyl-piperazin-1-yl)-pyridin-2-yl]-biphenyl-4-carboxylic acid amide;
3'-[4-(4-Methyl-piperazin-1-yl)-pyridin-2-yl]-biphenyl-4-carboxylic acid ethyl ester;
Dimethyl-{3'-[4-(4-methyl-piperazin-1-yl)-pyridin-2-yl]-biphenyl-4-yl}-amine;
{3-[4-(4-Methyl-piperazin-1-yl)-pyridin-2-yl]-thiophen-2-yl}-methanol;
3'-[4-(4-Methyl-piperazin-1-yl)-pyridin-2-yl]-biphenyl-4-carboxylic acid;
{3'-[4-(4-Methyl-piperazin-1-yl)-pyridin-2-yl]-biphenyl-4-yl}-morpholin-4-yl-methanone;
{3'-[4-(4-Methyl-piperazin-1-yl)-pyridin-2-yl]-biphenyl-4-yl}-pyrrolidin-1-yl-methanone;
1-Methyl-4-[2-(3-trifluoromethyl-phenyl)-pyridin-4-yl]-piperazine;
1-Methyl-4-(2-o-tolyl-pyridin-4-yl)-piperazine;
4-(4-Methyl-piperazin-1-yl)-[2,3']bipyridinyl;
1-[2-(3,5-Dimethyl-phenyl)-pyridin-4-yl]-4-methyl-piperazine;
Dimethyl-{3-[4-(4-methyl-piperazin-1-yl)-pyridin-2-yl]-phenyl}-amine;
1-[2-(3-Methoxymethyl-phenyl)-pyridin-4-yl]-4-methyl-piperazine;
2-[4-(4-Methyl-piperazin-1-yl)-pyridin-2-yl]-phenol;
1-Methyl-4-[2-(4-methyl-thiophen-2-yl)-pyridin-4-yl]-piperazine;
1-(2-Benzofuran-2-yl-pyridin-4-yl)-4-methyl-piperazine;
1-(2-Benzo[b]thiophen-3-yl-pyridin-4-yl)-4-methyl-piperazine;
1-[2-(3-Chloro-phenyl)-pyridin-4-yl]-4-methyl-piperazine;
1-Methyl-4-(2-naphthalen-1-yl-pyridin-4-yl)-piperazine;
1-Methyl-4-(2-naphthalen-2-yl-pyridin-4-yl)-piperazine;
1-Methyl-4-(2-m-tolyl-pyridin-4-yl)-piperazine;
1-(2-Biphenyl-4-yl-pyridin-4-yl)-4-methyl-piperazine;
4-[4-(4-Methyl-piperazin-1-yl)-pyridin-2-yl]-phenylamine;
1-Methyl-4-(2-methyl-6-thiophen-2-yl-pyridin-4-yl)-piperazine;

1-Methyl-4-[2-(5-phenyl-thiophen-2-yl)-pyridin-4-yl]-piperazine;
1-Methyl-4-[2-(4'-methyl-biphenyl-3-yl)-pyridin-4-yl]-piperazine;
1-[2-(3'-Chloro-4'-fluoro-biphenyl-3-yl)-pyridin-4-yl]-4-methyl-piperazine;
1-[2-(2',3'-Dichloro-biphenyl-3-yl)-pyridin-4-yl]-4-methyl-piperazine;
2-Biphenyl-3-yl-4-(4-methyl-piperazin-1-yl)-[1,3,5]triazine;
1-[2-(2,5-Dichloro-thiophen-3-yl)-pyridin-4-yl]-4-methyl-piperazine;
1-[2-(5-Bromo-2-chloro-thiophen-3-yl)-pyridin-4-yl]-4-methyl-piperazine;
3-[4-(4-Methyl-piperazin-1-yl)-[1,3,5]triazin-2-yl]-benzonitrile;
2-(4-Methyl-piperazin-1-yl)-4-naphthalen-1-yl-[1,3,5]triazine;
C-{3-[4-(4-Methyl-piperazin-1-yl)-pyridin-2-yl]-thiophen-2-yl}-methylamine;
1-[2-(3-Furan-3-yl-phenyl)-pyridin-4-yl]-4-methyl-piperazine;
2-(4-Fluoro-3-methyl-phenyl)-4-(4-methyl-piperazin-1-yl)-[1,3,5]triazine;
2-Biphenyl-4-yl-4-(4-methyl-piperazin-1-yl)-[1,3,5]triazine;
2-(4-Methyl-piperazin-1-yl)-4-naphthalen-2-yl-[1,3,5]triazine;
2-(4-Methyl-piperazin-1-yl)-4-phenyl-[1,3,5]triazine;
2-(2-Chloro-pyridin-3-yl)-4-(4-methyl-piperazin-1-yl)-[1,3,5]triazine;
2-Bromo-4-[4-(4-methyl-piperazin-1-yl)-pyridin-2-yl]-phenylamine;
2-(4-Methyl-piperazin-1-yl)-4-(4-nitro-phenyl)-[1,3,5]triazine;
2-(2,4-Difluoro-phenyl)-4-(4-methyl-piperazin-1-yl)-[1,3,5]triazine;
2-(5-Fluoro-2-methyl-phenyl)-4-(4-methyl-piperazin-1-yl)-[1,3,5]triazine;
5-[4-(4-Methyl-piperazin-1-yl)-pyridin-2-yl]-biphenyl-2-ylamine;
N-{3'-[4-(4-Methyl-piperazin-1-yl)-pyridin-2-yl]-biphenyl-4-yl}-acetamide;
5-[4-(4-Methyl-piperazin-1-yl)-pyridin-2-yl]-thiophene-2-carbonitrile;
1-Methyl-4-[2-(6-methyl-biphenyl-3-yl)-pyridin-4-yl]-piperazine;
1-Methyl-4-(2-phenyl-pyridin-4-yl)-piperazine;
3-[4-(4-Methyl-piperazin-1-yl)-pyridin-2-yl]-thiophene-2-carbonitrile;
2-(4-Methoxy-thiophen-3-yl)-4-(4-methyl-piperazin-1-yl)-[1,3,5]triazine;
2-(4-Methyl-piperazin-1-yl)-4-(5-pyridin-2-yl-thiophen-2-yl)-[1,3,5]triazine;
{4-[4-(4-Methyl-piperazin-1-yl)-pyridin-2-yl]-thiophen-2-yl}-methanol;
4-[4-(4-Methyl-piperazin-1-yl)-pyridin-2-yl]-thiophene-2-carbonitrile;
1-Methyl-4-[2-(5-vinyl-thiophen-3-yl)-pyridin-4-yl]-piperazine;
1-[2-(5-Ethyl-thiophen-3-yl)-pyridin-4-yl]-4-methyl-piperazine;
1-[2-(5-Isopropenyl-thiophen-3-yl)-pyridin-4-yl]-4-methyl-piperazine;
2-(3,5-Difluoro-phenyl)-4-(4-methyl-piperazin-1-yl)-[1,3,5]triazine;
2-(2-Chloro-4-fluoro-phenyl)-4-(4-methyl-piperazin-1-yl)-[1,3,5]triazine;
2-(4-Methyl-piperazin-1-yl)-4-pyridin-2-yl-[1,3,5]triazine;
2-(4-Methyl-piperazin-1-yl)-4-(3-methyl-thiophen-2-yl)-[1,3,5]triazine;
1-[2-(5-Chloro-2-methyl-thiophen-3-yl)-pyridin-4-yl]-4-methyl-piperazine;
1-Methyl-4-[2-(5-methyl-furan-2-yl)-pyridin-4-yl]-piperazine;
2-(2,5-Dichloro-thiophen-3-yl)-4-(4-methyl-piperazin-1-yl)-[1,3,5]triazine;
2-Benzo[b]thiophen-3-yl-4-(4-methyl-piperazin-1-yl)-[1,3,5]triazine;
1-Methyl-4-[2-(2-vinyl-thiophen-3-yl)-pyridin-4-yl]-piperazine;
1-Methyl-4-(3-methyl-2-thiophen-3-yl-pyridin-4-yl)-piperazine;
2-Methyl-4-(4-methyl-piperazin-1-yl)-6-(3,4,5-trifluoro-phenyl)-[1,3,5]triazine;
1-[2-(5-Chloro-3-methyl-thiophen-2-yl)-pyridin-4-yl]-4-methyl-piperazine;
1-(2-[2,2']Bithiophenyl-5-yl-pyridin-4-yl)-4-methyl-piperazine;
1-[2-(4,5-Dichloro-thiophen-2-yl)-pyridin-4-yl]-4-methyl-piperazine;
2-(4-Chloro-thiophen-2-yl)-4-(4-methyl-piperazin-1-yl)-[1,3,5]triazine;
1-[2-(3-Chloro-thiophen-2-yl)-pyridin-4-yl]-4-methyl-piperazine;

and pharmaceutically acceptable salts, prodrugs and active metabolites thereof.

In another embodiment, the present invention is directed to one or more compounds selected from the group consisting of:
2-(4-Methyl-piperazin-1-yl)-4-thiophen-3-yl-[1,3,5]triazine;
2-(4-Methyl-piperazin-1-yl)-4-thiophen-2-yl-[1,3,5]triazine;
2-(3-Fluoro-4-methyl-phenyl)-4-(4-methyl-piperazin-1-yl)-[1,3,5]triazine;
2-(4-Methyl-piperazin-1-yl)-4-p-tolyl-[1,3,5]triazine;
2-(3,4-Difluoro-phenyl)-4-(4-methyl-piperazin-1-yl)-[1,3,5]triazine;
2-Furan-3-yl-4-(4-methyl-piperazin-1-yl)-[1,3,5]triazine;
2-(3-Fluoro-phenyl)-4-(4-methyl-piperazin-1-yl)-[1,3,5]triazine;
2-(4-Methyl-piperazin-1-yl)-4-(3-trifluoromethyl-phenyl)-[1,3,5]triazine;
(2-(4-Bromo-thiophen-2-yl)-4-(4-methyl-piperazin-1-yl)-[1,3,5]triazine;
2-(4-Bromo-phenyl)-4-(4-methyl-piperazin-1-yl)-[1,3,5]triazine;
2-(4-Methyl-piperazin-1-yl)-4-(3,4,5-trifluoro-phenyl)-[1,3,5]triazine;
2-(4-Fluoro-phenyl)-4-(4-methyl-piperazin-1-yl)-[1,3,5]triazine;
2-(4-Chloro-phenyl)-4-(4-methyl-piperazin-1-yl)-[1,3,5]triazine;
2-(3,4-Dichloro-phenyl)-4-(4-methyl-piperazin-1-yl)-[1,3,5]triazine;
2-(3-Bromo-thiophen-2-yl)-4-(4-methyl-piperazin-1-yl)-[1,3,5]triazine;
2-(6-Chloro-pyridin-3-yl)-4-(4-methyl-piperazin-1-yl)-[1,3,5]triazine;
2-(3-Chloro-thiophen-2-yl)-4-(4-methyl-piperazin-1-yl)-[1,3,5]triazine;

2-(5-Bromo-thiophen-2-yl)-4-(4-methyl-piperazin-1-yl)-[1,3,5]triazine;
2-(4-Methyl-piperazin-1-yl)-4-pyridin-3-yl-[1,3,5]triazine;
2-(4-Methyl-piperazin-1-yl)-4-pyridin-4-yl-[1,3,5]triazine;
2-Benzo[b]thiophen-2-yl-4-(4-methyl-piperazin-1-yl)-[1,3,5]triazine;
2-(4-Methyl-piperazin-1-yl)-4-(5-methyl-2-trifluoromethyl-furan-3-yl)-[1,3,5]triazine;
2-(3-Bromo-thiophen-2-yl)-4-methyl-6-(4-methyl-piperazin-1-yl)-[1,3,5]triazine;
1-[4-(3-Bromo-thiophen-2-yl)-[1,3,5]triazin-2-yl]-4-methyl-[1,4]diazepane;
2-(5-Chloro-thiophen-2-yl)-4-(4-methyl-piperazin-1-yl)-[1,3,5]triazine;
2-Biphenyl-3-yl-4-(4-methyl-piperazin-1-yl)-[1,3,5]triazine;
3-[4-(4-Methyl-piperazin-1-yl)-[1,3,5]triazin-2-yl]-benzonitrile;
2-(4-Methyl-piperazin-1-yl)-4-naphthalen-1-yl-[1,3,5]triazine;
2-(4-Fluoro-3-methyl-phenyl)-4-(4-methyl-piperazin-1-yl)-[1,3,5]triazine;
2-Biphenyl-4-yl-4-(4-methyl-piperazin-1-yl)-[1,3,5]triazine;
2-(4-Methyl-piperazin-1-yl)-4-naphthalen-2-yl-[1,3,5]triazine;
2-(4-Methyl-piperazin-1-yl)-4-phenyl-[1,3,5]triazine;
2-(2-Chloro-pyridin-3-yl)-4-(4-methyl-piperazin-1-yl)-[1,3,5]triazine;
2-(4-Methyl-piperazin-1-yl)-4-(4-nitro-phenyl)-[1,3,5]triazine;
2-(2,4-Difluoro-phenyl)-4-(4-methyl-piperazin-1-yl)-[1,3,5]triazine;
2-(5-Fluoro-2-methyl-phenyl)-4-(4-methyl-piperazin-1-yl)-[1,3,5]triazine;
2-(4-Methoxy-thiophen-3-yl)-4-(4-methyl-piperazin-1-yl)-[1,3,5]triazine;
2-(4-Methyl-piperazin-1-yl)-4-(5-pyridin-2-yl-thiophen-2-yl)-[1,3,5]triazine;
2-(3,5-Difluoro-phenyl)-4-(4-methyl-piperazin-1-yl)-[1,3,5]triazine;
2-(2-Chloro-4-fluoro-phenyl)-4-(4-methyl-piperazin-1-yl)-[1,3,5]triazine;
2-(4-Methyl-piperazin-1-yl)-4-pyridin-2-yl-[1,3,5]triazine;
2-(4-Methyl-piperazin-1-yl)-4-(3-methyl-thiophen-2-yl)-[1,3,5]triazine;
2-(2,5-Dichloro-thiophen-3-yl)-4-(4-methyl-piperazin-1-yl)-[1,3,5]triazine;
2-Benzo[b]thiophen-3-yl-4-(4-methyl-piperazin-1-yl)-[1,3,5]triazine;
2-Methyl-4-(4-methyl-piperazin-1-yl)-6-(3,4,5-trifluoro-phenyl)-[1,3,5]triazine;
2-(4-Chloro-thiophen-2-yl)-4-(4-methyl-piperazin-1-yl)-[1,3,5]triazine;
and pharmaceutically acceptable salts, prodrugs and active metabolites thereof.

In another embodiment, the present invention is directed to one or more compounds selected from the group consisting of:
1-Methyl-4-(2-thiophen-3-yl-pyridin-4-yl)-piperazine;
1-(2-Furan-2-yl-pyridin-4-yl)-4-methyl-piperazine;
1-(2-Furan-3-yl-pyridin-4-yl)-4-methyl-piperazine;
1-Methyl-4-[2-(4-methyl-thiophen-3-yl)-pyridin-4-yl]-piperazine;
1-[2-(3-Chloro-4-fluoro-phenyl)-pyridin-4-yl]-4-methyl-piperazine;
1-[2-(3-Fluoro-4-methyl-phenyl)-pyridin-4-yl]-4-methyl-piperazine;
1-Methyl-4-(2-p-tolyl-pyridin-4-yl)-piperazine;
3-[4-(4-Methyl-piperazin-1-yl)-pyridin-2-yl]-phenol;
1-[2-(3,4-Difluoro-phenyl)-pyridin-4-yl]-4-methyl-piperazine;
1-[2-(2,3-Dichloro-phenyl)-pyridin-4-yl]-4-methyl-piperazine;
1-[2-(2,3-Dichloro-phenyl)-pyridin-4-yl]-4-methyl-piperazine;
1-[2-(3-Chloro-4-methyl-phenyl)-pyridin-4-yl]-4-methyl-piperazine;
1-(2-Biphenyl-3-yl-pyridin-4-yl)-4-methyl-piperazine;
1-Methyl-4-(2-thiophen-3-yl-pyridin-4-yl)-[1,4]diazepane;
1-{2-[2-Chloro-5-(4-fluoro-phenyl)-thiophen-3-yl]-pyridin-4-yl}-4-methyl-piperazine;
1-(2-Dibenzofuran-4-yl-pyridin-4-yl)-4-methyl-piperazine;
1-Methyl-5-[4-(4-methyl-piperazin-1-yl)-pyridin-2-yl]-1H-indole;
1-[2-(2-Chloro-thiophen-3-yl)-pyridin-4-yl]-4-methyl-piperazine;
1-Methyl-4-[2-(2-methyl-thiophen-3-yl)-pyridin-4-yl]-piperazine;
1-[2-(4-Chloro-thiophen-2-yl)-pyridin-4-yl]-4-methyl-piperazine;
1-Methyl-4-(2-thiophen-2-yl-pyridin-4-yl)-piperazine;
1-[2-(5-Chloro-thiophen-2-yl)-pyridin-4-yl]-4-methyl-piperazine;
1-[2-(5-Bromo-thiophen-2-yl)-pyridin-4-yl]-4-methyl-piperazine;
1-[2-(4'-Fluoro-biphenyl-3-yl)-pyridin-4-yl]-4-methyl-piperazine;
1-[2-(4'-Methoxy-biphenyl-3-yl)-pyridin-4-yl]-4-methyl-piperazine;
1-[2-(4'-Chloro-biphenyl-3-yl)-pyridin-4-yl]-4-methyl-piperazine;
3'-[4-(4-Methyl-piperazin-1-yl)-pyridin-2-yl]-biphenyl-4-carbonitrile;
3'-[4-(4-Methyl-piperazin-1-yl)-pyridin-2-yl]-biphenyl-4-carboxylic acid amide;
3'-[4-(4-Methyl-piperazin-1-yl)-pyridin-2-yl]-biphenyl-4-carboxylic acid ethyl ester;
Dimethyl-{3'-[4-(4-methyl-piperazin-1-yl)-pyridin-2-yl]-biphenyl-4-yl}-amine;
{3-[4-(4-Methyl-piperazin-1-yl)-pyridin-2-yl]-thiophen-2-yl}-methanol;
3'-[4-(4-Methyl-piperazin-1-yl)-pyridin-2-yl]-biphenyl-4-carboxylic acid;
{3'-[4-(4-Methyl-piperazin-1-yl)-pyridin-2-yl]-biphenyl-4-yl}-morpholin-4-yl-methanone;
{3'-[4-(4-Methyl-piperazin-1-yl)-pyridin-2-yl]-biphenyl-4-yl}-pyrrolidin-1-yl-methanone;
1-Methyl-4-[2-(3-trifluoromethyl-phenyl)-pyridin-4-yl]-piperazine;
1-Methyl-4-(2-o-tolyl-pyridin-4-yl)-piperazine;
4-(4-Methyl-piperazin-1-yl)-[2,3']bipyridinyl;
1-[2-(3,5-Dimethyl-phenyl)-pyridin-4-yl]-4-methyl-piperazine;
Dimethyl-{3-[4-(4-methyl-piperazin-1-yl)-pyridin-2-yl]-phenyl}-amine;
1-[2-(3-Methoxymethyl-phenyl)-pyridin-4-yl]-4-methyl-piperazine;
2-[4-(4-Methyl-piperazin-1-yl)-pyridin-2-yl]-phenol;
1-Methyl-4-[2-(4-methyl-thiophen-2-yl)-pyridin-4-yl]-piperazine;
1-(2-Benzofuran-2-yl-pyridin-4-yl)-4-methyl-piperazine;

1-(2-Benzo[b]thiophen-3-yl-pyridin-4-yl)-4-methyl-piperazine;
1-[2-(3-Chloro-phenyl)-pyridin-4-yl]-4-methyl-piperazine;
1-Methyl-4-(2-naphthalen-1-yl-pyridin-4-yl)-piperazine;
1-Methyl-4-(2-naphthalen-2-yl-pyridin-4-yl)-piperazine;
1-Methyl-4-(2-m-tolyl-pyridin-4-yl)-piperazine;
1-(2-Biphenyl-4-yl-pyridin-4-yl)-4-methyl-piperazine;
4-[4-(4-Methyl-piperazin-1-yl)-pyridin-2-yl]-phenylamine;
1-Methyl-4-(2-methyl-6-thiophen-2-yl-pyridin-4-yl)-piperazine;
1-Methyl-4-[2-(5-phenyl-thiophen-2-yl)-pyridin-4-yl]-piperazine;
1-Methyl-4-[2-(4'-methyl-biphenyl-3-yl)-pyridin-4-yl]-piperazine;
1-[2-(3'-Chloro-4'-fluoro-biphenyl-3-yl)-pyridin-4-yl]-4-methyl-piperazine;
1-[2-(2',3'-Dichloro-biphenyl-3-yl)-pyridin-4-yl]-4-methyl-piperazine;
1-[2-(2,5-Dichloro-thiophen-3-yl)-pyridin-4-yl]-4-methyl-piperazine;
1-[2-(5-Bromo-2-chloro-thiophen-3-yl)-pyridin-4-yl]-4-methyl-piperazine;
C-{3-[4-(4-Methyl-piperazin-1-yl)-pyridin-2-yl]-thiophen-2-yl}-methylamine;
1-[2-(3-Furan-3-yl-phenyl)-pyridin-4-yl]-4-methyl-piperazine;
2-Bromo-4-[4-(4-methyl-piperazin-1-yl)-pyridin-2-yl]-phenylamine;
5-[4-(4-Methyl-piperazin-1-yl)-pyridin-2-yl]-biphenyl-2-ylamine;
N-{3'-[4-(4-Methyl-piperazin-1-yl)-pyridin-2-yl]-biphenyl-4-yl}-acetamide;
5-[4-(4-Methyl-piperazin-1-yl)-pyridin-2-yl]-thiophene-2-carbonitrile;
1-Methyl-4-[2-(6-methyl-biphenyl-3-yl)-pyridin-4-yl]-piperazine;
1-Methyl-4-(2-phenyl-pyridin-4-yl)-piperazine;
3-[4-(4-Methyl-piperazin-1-yl)-pyridin-2-yl]-thiophene-2-carbonitrile;
{4-[4-(4-Methyl-piperazin-1-yl)-pyridin-2-yl]-thiophen-2-yl}-methanol;
4-[4-(4-Methyl-piperazin-1-yl)-pyridin-2-yl]-thiophene-2-carbonitrile;
1-Methyl-4-[2-(5-vinyl-thiophen-3-yl)-pyridin-4-yl]-piperazine;
1-[2-(5-Ethyl-thiophen-3-yl)-pyridin-4-yl]-4-methyl-piperazine;
1-[2-(5-isopropenyl-thiophen-3-yl)-pyridin-4-yl]-4-methyl-piperazine;
1-[2-(5-Chloro-2-methyl-thiophen-3-yl)-pyridin-4-yl]-4-methyl-piperazine;
1-Methyl-4-[2-(5-methyl-furan-2-yl)-pyridin-4-yl]-piperazine;
1-Methyl-4-[2-(2-vinyl-thiophen-3-yl)-pyridin-4-yl]-piperazine;
1-Methyl-4-(3-methyl-2-thiophen-3-yl-pyridin-4-yl)-piperazine;
1-[2-(5-Chloro-3-methyl-thiophen-2-yl)-pyridin-4-yl]-4-methyl-piperazine;
1-(2-[2,2']Bithiophenyl-5-yl-pyridin-4-yl)-4-methyl-piperazine;
1-[2-(4,5-Dichloro-thiophen-2-yl)-pyridin-4-yl]-4-methyl-piperazine;
1-[2-(3-Chloro-thiophen-2-yl)-pyridin-4-yl]-4-methyl-piperazine;
and pharmaceutically acceptable salts, prodrugs and active metabolites thereof.

In another embodiment, the present invention is directed to one or more compounds selected from the group consisting of:
1-Methyl-4-(4-thiophen-2-yl-pyridin-2-yl)-piperazine;
4-(4-Methyl-piperazin-1-yl)-2-thiophen-2-yl-pyrimidine;
4-(4-Methyl-piperazin-1-yl)-6-thiophen-2-yl-pyrimidine;
4-piperazin-1-yl-6-thiophen-2-yl-pyrimidine;
1-Methyl-4-(6-thiophen-2-yl-pyrimidin-4-yl)-[1,4]diazepane;
2-piperazin-1-yl-4-thiophen-2-yl-pyrimidine;
4-(4-Methyl-piperazin-1-yl)-2-phenyl-pyrimidine;
2-(3-Chloro-4-fluoro-phenyl)-4-(4-methyl-piperazin-1-yl)-pyrimidine;
2-(3-Fluoro-phenyl)-4-(4-methyl-piperazin-1-yl)-pyrimidine;
1-(4-Thiophen-2-yl-pyrimidin-2-yl)-[1,4]diazepane;
1-Methyl-4-(6-thiophen-2-yl-pyridin-2-yl)-piperazine;
1-Methyl-4-(5-thiophen-2-yl-pyridin-3-yl)-piperazine;
4-Methyl-2-(4-methyl-piperazin-1-yl)-6-thiophen-2-yl-pyrimidine;
1-[4-(3-Fluoro-4-methyl-phenyl)-pyridin-2-yl]-4-methyl-piperazine;
1-(4-Biphenyl-3-yl-pyridin-2-yl)-4-methyl-piperazine;
2-(3-Fluoro-4-methyl-phenyl)-4-(4-methyl-piperazin-1-yl)-pyrimidine;
2-Biphenyl-3-yl-4-(4-methyl-piperazin-1-yl)-pyrimidine;
4-(4-Methyl-piperazin-1-yl)-2-thiophen-3-yl-pyrimidine;
1-Methyl-4-(4-thiophen-3-yl-pyridin-2-yl)-piperazine;
4-(4-Chloro-thiophen-2-yl)-2-(4-methyl-piperazin-1-yl)-pyrimidine;
2-Chloro-4-(3-chloro-thiophen-2-yl)-6-(4-methyl-piperazin-1-yl)-pyrimidine;
2-Chloro-4-(4-methyl-piperazin-1-yl)-6-thiophen-2-yl-pyrimidine;
Methyl-(1-methyl-pyrrolidin-3-yl)-(2-thiophen-3-yl-pyridin-4-yl)-amine;
N,N,N'-Trimethyl-N'-(2-thiophen-3-yl-pyridin-4-yl)-ethane-1,2-diamine;
Dimethyl-[1-(2-thiophen-3-yl-pyridin-4-yl)-pyrrolidin-3-yl]-amine;
Methyl-[1-(2-thiophen-3-yl-pyridin-4-yl)-pyrrolidin-3-yl]-amine;
and pharmaceutically acceptable salts, prodrugs and active metabolites thereof.

In another embodiment, the present invention is directed to one or more compounds selected from the group consisting of:
1-Methyl-4-(4-thiophen-2-yl-pyridin-2-yl)-piperazine;
4-(4-Methyl-piperazin-1-yl)-2-thiophen-2-yl-pyrimidine;
4-(4-Methyl-piperazin-1-yl)-6-thiophen-2-yl-pyrimidine;
4-piperazin-1-yl-6-thiophen-2-yl-pyrimidine;
1-Methyl-4-(6-thiophen-2-yl-pyrimidin-4-yl)-[1,4]diazepane;
2-piperazin-1-yl-4-thiophen-2-yl-pyrimidine;
4-(4-Methyl-piperazin-1-yl)-2-phenyl-pyrimidine;
2-(3-Chloro-4-fluoro-phenyl)-4-(4-methyl-piperazin-1-yl)-pyrimidine;
2-(3-Fluoro-phenyl)-4-(4-methyl-piperazin-1-yl)-pyrimidine;
1-(4-Thiophen-2-yl-pyrimidin-2-yl)-[1,4]diazepane;
1-Methyl-4-(6-thiophen-2-yl-pyridin-2-yl)-piperazine;
1-Methyl-4-(5-thiophen-2-yl-pyridin-3-yl)-piperazine;
4-Methyl-2-(4-methyl-piperazin-1-yl)-6-thiophen-2-yl-pyrimidine;
1-[4-(3-Fluoro-4-methyl-phenyl)-pyridin-2-yl]-4-methyl-piperazine;
1-(4-Biphenyl-3-yl-pyridin-2-yl)-4-methyl-piperazine;

2-(3-Fluoro-4-methyl-phenyl)-4-(4-methyl-piperazin-1-yl)-pyrimidine;
2-Biphenyl-3-yl-4-(4-methyl-piperazin-1-yl)-pyrimidine;
4-(4-Methyl-piperazin-1-yl)-2-thiophen-3-yl-pyrimidine;
1-Methyl-4-(4-thiophen-3-yl-pyridin-2-yl)-piperazine;
4-(4-Chloro-thiophen-2-yl)-2-(4-methyl-piperazin-1-yl)-pyrimidine;
2-Chloro-4-(3-chloro-thiophen-2-yl)-6-(4-methyl-piperazin-1-yl)-pyrimidine;
2-Chloro-4-(4-methyl-piperazin-1-yl)-6-thiophen-2-yl-pyrimidine;
and pharmaceutically acceptable salts, prodrugs and active metabolites thereof.

In another embodiment, the present invention is directed to one or more compounds selected from the group consisting of:
Methyl-(1-methyl-pyrrolidin-3-yl)-(2-thiophen-3-yl-pyridin-4-yl)-amine;
N,N,N'-Trimethyl-N'-(2-thiophen-3-yl-pyridin-4-yl)-ethane-1,2-diamine;
Dimethyl-[1-(2-thiophen-3-yl-pyridin-4-yl)-pyrrolidin-3-yl]-amine;
Methyl-[1-(2-thiophen-3-yl-pyridin-4-yl)-pyrrolidin-3-yl]-amine;
and pharmaceutically acceptable salts, prodrugs and active metabolites thereof.

In another embodiment, the present invention is directed to one or more compounds selected from the group consisting of:
4-(4-Methyl-piperazin-1-yl)-2-thiophen-2-yl-pyrimidine;
4-(4-Methyl-piperazin-1-yl)-6-thiophen-2-yl-pyrimidine;
2-(3-Chloro-4-fluoro-phenyl)-4-(4-methyl-piperazin-1-yl)-pyrimidine;
2-Chloro-4-(3-chloro-thiophen-2-yl)-6-(4-methyl-piperazin-1-yl)-pyrimidine;
2-Chloro-4-(4-methyl-piperazin-1-yl)-6-thiophen-2-yl-pyrimidine;
Methyl-[1-(2-thiophen-3-yl-pyridin-4-yl)-pyrrolidin-3-yl]-amine;
and pharmaceutically acceptable salts, prodrugs and active metabolites thereof.

Additional embodiments of the present invention, include those wherein the substituents selected for one or more of the variables defined herein (i.e., $R^1$, $R^2$, a,

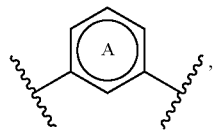

etc.) are independently selected to be any individual substituent or any subset of substituents selected from the complete list as defined herein.

Embodiments of compounds of formula (I) of the present invention include those listed in Tables 1-2 below. Illustrative embodiments of the present invention are exemplified by any single compound or subset of compounds selected from the compounds listed in Tables 1-2 below.

TABLE 1

Representative Compounds of Formula (I)

| ID No. | $R^1$ | (linker) | a | $R^2$ |
|---|---|---|---|---|
| 1 | 3-thienyl | triazine | 1 | methyl |
| 2 | 2-thienyl | triazine | 1 | methyl |
| 3 | 3-fluoro-4-methyl-phenyl | triazine | 1 | methyl |
| 4 | 4-methylphenyl | triazine | 1 | methyl |
| 5 | 3,4-difluorophenyl | triazine | 1 | methyl |
| 6 | 3-furyl | pyrimidine | 1 | methyl |
| 7 | 3-fluorophenyl | pyrimidine | 1 | methyl |
| 8 | 3-trifluoromethyl-phenyl | pyrazine | 1 | methyl |

TABLE 1-continued

Representative Compounds of Formula (I)

| ID No. | R¹ | A | a | R² |
|---|---|---|---|---|
| 9 | 2-(4-bromo-thineyl) | triazine | 1 | methyl |
| 10 | 4-bromophenyl | triazine | 1 | methyl |
| 11 | 3,4,5-trifluorophenyl | triazine | 1 | methyl |
| 12 | 4-fluorophenyl | triazine | 1 | methyl |
| 13 | 4-chlorophenyl | triazine | 1 | methyl |
| 14 | 3,4-dichlorophenyl | triazine | 1 | methyl |
| 15 | 2-(3-bromo-thienyl) | pyrimidine | 1 | methyl |
| 16 | 3-(6-chloro-pyridyl) | triazine | 1 | methyl |
| 17 | 2-(3-chloro-thienyl) | triazine | 1 | methyl |
| 18 | 2-(5-bromo-thienyl) | triazine | 1 | methyl |
| 19 | 3-pyridyl | triazine | 1 | methyl |
| 20 | 4-pyridyl | triazine | 1 | methyl |
| 21 | 2-benzothienyl | triazine | 1 | methyl |
| 22 | 3-(2-trifluoromethyl-5-methyl-furyl) | triazine | 1 | methyl |
| 23 | 2-(3-bromo-thienyl) | dimethyl-triazine | 1 | methyl |
| 24 | 2-(3-bromo-thienyl) | triazine | 2 | methyl |

TABLE 1-continued

Representative Compounds of Formula (I)

| ID No. | R¹ | A | a | R² |
|---|---|---|---|---|
| 25 | 2-(5-chloro-thienyl) | triazine | 1 | methyl |
| 108 | 3-biphenyl | triazine | 1 | methyl |
| 111 | 3-cyanophenyl | triazine | 1 | methyl |
| 112 | 1-naphthyl | triazine | 1 | methyl |
| 115 | 3-methyl-4-fluoro phenyl | triazine | 1 | methyl |
| 116 | 4-biphenyl | triazine | 1 | methyl |
| 117 | 2-naphthyl | pyrimidine | 1 | methyl |
| 118 | phenyl | triazine | 1 | methyl |
| 119 | 3-(2-chloro-pyridyl) | triazine | 1 | methyl |
| 121 | 4-nitrophenyl | triazine | 1 | methyl |
| 122 | 2,4-difluorophenyl | triazine | 1 | methyl |
| 123 | 1-methyl-3-fluoro phenyl | triazine | 1 | methyl |
| 130 | 3-(4-methoxy-thienyl) | triazine | 1 | methyl |
| 131 | 2-(5-(2-pyridyl)-thienyl) | pyrimidine | 1 | methyl |
| 137 | 3,5-difluorophenyl | pyrimidine | 1 | methyl |
| 138 | 2-chloro-4-fluoro-phenyl | triazine | 1 | methyl |

TABLE 1-continued

Representative Compounds of Formula (I)

| ID No. | R¹ | (A ring with wavy bonds) | a | R² |
|---|---|---|---|---|
| 139 | 2-pyridyl | 1,3,5-triazine-2,4-diyl | 1 | methyl |
| 140 | 2-(3-methyl-thienyl) | 1,3,5-triazine-2,4-diyl | 1 | methyl |
| 143 | 2-(2,5-dichlorothienyl) | 1,3,5-triazine-2,4-diyl | 1 | methyl |
| 144 | 3-benzothienyl | 1,3,5-triazine-2,4-diyl | 1 | methyl |
| 147 | 3,4,5-trifluorophenyl | 6-methyl-1,3,5-triazine-2,4-diyl | 1 | methyl |
| 151 | 2-(4-chloro-thienyl) | 1,3,5-triazine-2,4-diyl | 1 | methyl |

TABLE 2

Representative Compounds of Formula (I)

| ID No. | R¹ | (A ring) | a | R² |
|---|---|---|---|---|
| 26 | 3-thienyl | 2,4-pyridyl | 1 | methyl |
| 27 | 2-furyl | 2,4-pyridyl | 1 | methyl |
| 28 | 3-furyl | 2,4-pyridyl | 1 | methyl |
| 29 | 3-(4-methyl-thienyl) | 2,4-pyridyl | 1 | methyl |
| 30 | 3-chloro-4-fluoro-phenyl | 2,4-pyridyl | 1 | methyl |
| 31 | 3-fluoro-4-methyl-phenyl | 2,4-pyridyl | 1 | methyl |
| 32 | 4-methylphenyl | 2,4-pyridyl | 1 | methyl |
| 33 | 3-hydroxyphenyl | 2,4-pyridyl | 1 | methyl |

TABLE 2-continued

Representative Compounds of Formula (I)

| ID No. | R¹ | A | a | R² |
|---|---|---|---|---|
| 34 | 3,4-difluorophenyl | 2,4-pyridyl | 1 | methyl |
| 35 | 2,3-dichlorophenyl | 2,4-pyridyl | 1 | methyl |
| 36 | 3,4-dichlorophenyl | 2,4-pyridyl | 1 | methyl |
| 37 | 3-chloro-4-methyl-phenyl | 2,4-pyridyl | 1 | methyl |
| 38 | 3-biphenyl | 2,4-pyridyl | 1 | methyl |
| 39 | 3-thienyl | 2,4-pyridyl | 2 | methyl |
| 45 | 3-(2-chloro-5-(4-fluorophenyl)-thienyl) | 2,4-pyridyl | 1 | methyl |
| 46 | 4-dibenzofuryl | 2,4-pyridyl | 1 | methyl |
| 47 | 5-(1-methyl-indolyl) | 2,4-pyridyl | 1 | methyl |
| 48 | 3-(2-chloro-thienyl) | 2,4-pyridyl | 1 | methyl |
| 49 | 3-(2-methyl-thienyl) | 2,4-pyridyl | 1 | methyl |
| 50 | 2-(4-chloro-thienyl) | 2,4-pyridyl | 1 | methyl |
| 51 | 2-thienyl | 2,4-pyridyl | 1 | methyl |
| 52 | 2-(5-chloro-thienyl) | 2,4-pyridyl | 1 | methyl |
| 53 | 2-(5-bromo-thienyl) | 2,4-pyridyl | 1 | methyl |
| 54 | 3-(4'-fluoro-biphenyl) | 2,4-pyridyl | 1 | methyl |

TABLE 2-continued

Representative Compounds of Formula (I)

| ID No. | R¹ | A | a | R² |
|---|---|---|---|---|
| 55 | 3-(4'-methoxy-biphenyl) | pyridyl | 1 | methyl |
| 56 | 3-(4'-chloro-biphenyl) | pyridyl | 1 | methyl |
| 57 | 3-(4'-cyano-biphenyl) | pyridyl | 1 | methyl |
| 58 | 3-(4'-(amino-carbonyl)-biphenyl | pyridyl | 1 | methyl |
| 59 | 3-(4'-(ethoxy-carbonyl)-biphenyl | pyridyl | 1 | methyl |
| 60 | 3-(4'-dimethylamino-biphenyl | pyridyl | 1 | methyl |
| 62 | 3-(2-hydroxymethyl-thienyl) | pyridyl | 1 | methyl |
| 63 | 3-(4'-carboxy-biphenyl) | pyridyl | 1 | methyl |
| 64 | 3-(4'-(4-morpholinyl-carbonyl)-biphenyl) | pyridyl | 1 | methyl |
| 65 | 3-(4'-(1-pyrrolidinyl-carbonyl)-biphenyl) | pyridyl | 1 | methyl |
| 80 | 3-trifluoromethyl-phenyl | pyridyl | 1 | methyl |
| 81 | 2-methylphenyl | pyridyl | 1 | methyl |
| 82 | 3-pyridyl | pyridyl | 1 | methyl |
| 83 | 3,5-dimethylphenyl | pyridyl | 1 | methyl |
| 84 | 3-dimethylamino-phenyl | pyridyl | 1 | methyl |
| 85 | 3-methoxy-methyl-phenyl | pyridyl | 1 | methyl |

TABLE 2-continued

Representative Compounds of Formula (I)

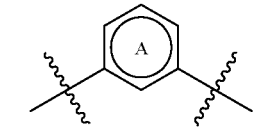

| ID No. | R¹ | a | R² |
|---|---|---|---|
| 86 | 2-hydroxyphenyl | 1 | methyl |
| 87 | 2-(4-methyl-thienyl) | 1 | methyl |
| 88 | 2-benzofuryl | 1 | methyl |
| 89 | 3-benzothienyl | 1 | methyl |
| 90 | 3-chlorophenyl | 1 | methyl |
| 91 | 1-naphthyl | 1 | methyl |
| 92 | 2-naphthyl | 1 | methyl |
| 93 | 3-methylphenyl | 1 | methyl |
| 94 | 4-biphenyl | 1 | methyl |
| 95 | 4-aminophenyl | 1 | methyl |
| 96 | 2-thienyl | 1 | methyl |
| 104 | 2-(5-phenyl-thienyl) | 1 | methyl |
| 105 | 3-(4'-methyl-biphenyl) | 1 | methyl |
| 106 | 3-(3'-chloro-4'-fluoro-biphenyl) | 1 | methyl |
| 107 | 3-(2',3'-dichloro-biphenyl) | 1 | methyl |
| 109 | 3-(2,5-dichlorothienyl) | 1 | methyl |

TABLE 2-continued

Representative Compounds of Formula (I)

| ID No. | R¹ | A | a | R² |
|---|---|---|---|---|
| 110 | 3-(2-chloro-5-bromo-thienyl) | pyridine (4,2) | 1 | methyl |
| 113 | 3-(2-aminomethyl-thienyl) | pyridine (4,2) | 1 | methyl |
| 114 | 3-(3-furyl)-phenyl | pyridine (4,2) | 1 | methyl |
| 120 | 3-bromo-4-amino-phenyl | pyridine (4,2) | 1 | methyl |
| 124 | 3-(6-amino-biphenyl) | pyridine (4,2) | 1 | methyl |
| 125 | 3-(4'-(methyl-carbonyl-amino)-biphenyl | pyridine (4,2) | 1 | methyl |
| 126 | 2-(5-cyano-thienyl) | pyridine (4,2) | 1 | methyl |
| 127 | 3-(6-methyl-biphenyl) | pyridine (4,2) | 1 | methyl |
| 128 | phenyl | pyridine (4,2) | 1 | methyl |
| 129 | 3-(2-cyano-thienyl) | pyridine (4,2) | 1 | methyl |
| 132 | 3-(5-hydroxymethyl-thienyl) | pyridine (4,2) | 1 | methyl |
| 133 | 3-(5-cyano-thienyl) | pyridine (4,2) | 1 | methyl |
| 134 | 3-(5-vinyl-thienyl) | pyridine (4,2) | 1 | methyl |
| 135 | 3-(5-ethyl-thienyl) | pyridine (4,2) | 1 | methyl |
| 136 | 3-(5-isopropenyl-thienyl) | pyridine (4,2) | 1 | methyl |
| 141 | 3-(2-methyl-5-chloro-thienyl) | pyridine (4,2) | 1 | methyl |

TABLE 2-continued

Representative Compounds of Formula (I)

[Structure: piperazine with R² on one N, (CH₂)ₐ chain, other N attached to ring A bearing R¹]

[Ring A template shown]

| ID No. | R¹ | A | a | R² |
|---|---|---|---|---|
| 142 | 2-(5-methyl-furyl) | pyridine (4,2-linked) | 1 | methyl |
| 145 | 3-(2-vinyl-thienyl) | pyridine (4,2-linked) | 1 | methyl |
| 146 | 3-thienyl | 3-methyl-pyridine | 1 | methyl |
| 148 | 2-(3-methyl-5-chloro-thienyl) | pyridine (4,2-linked) | 1 | methyl |
| 149 | 2-(5-(2-thienyl)-thienyl) | pyridine (4,2-linked) | 1 | methyl |
| 150 | 2-(4,5-dichloro-thienyl) | pyridine (4,2-linked) | 1 | methyl |
| 152 | 2-(3-chloro-thienyl) | pyridine (4,2-linked) | 1 | methyl |

Additional compounds of the present invention include those listed in Tables 3-4 below. Illustrative embodiments of the present invention are exemplified by any single compound or subset of compounds selected from the compounds listed in Tables 3 and 4 below.

TABLE 3

Representative Compounds of the Present Invention

[Structure: piperazine with R²⁰ on one N, (CH₂)_b chain, other N attached to ring B bearing R¹⁰]

[Ring B template shown]

| ID No. | R¹⁰ | B | b | R²⁰ |
|---|---|---|---|---|
| 67 | 2-thienyl | pyrimidine (4,6-linked) | 1 | methyl |
| 68 | 2-thienyl | pyrimidine (4,6-linked) | 1 | H |
| 69 | 2-thienyl | pyrimidine (4,6-linked) | 2 | methyl |
| 154 | 2-(3-chloro-thienyl) | 2-chloro-pyrimidine (4,6-linked) | 1 | methyl |
| 155 | 2-thienyl | 2-chloro-pyrimidine (4,6-linked) | 1 | methyl |
| 71 | 2-thienyl | pyrimidine (2,4-linked) | 1 | H |
| 75 | 2-thienyl | pyrimidine (2,4-linked) | 2 | H |

TABLE 3-continued

Representative Compounds of the Present Invention

| ID No. | R¹⁰ | b | R²⁰ |
|---|---|---|---|
| 79 | 2-thienyl | 1 | methyl |
| 153 | 2-(4-chloro-thienyl) | 1 | methyl |
| 61 | 2-thienyl | 1 | methyl |
| 72 | phenyl | 1 | methyl |
| 73 | 3-chloro-4-fluoro-phenyl | 1 | methyl |
| 74 | 3-fluorophenyl | 1 | methyl |
| 100 | 3-fluoro-4-methyl-phenyl | 1 | methyl |
| 101 | 3-biphenyl | 1 | methyl |
| 102 | 3-thienyl | 1 | methyl |
| 78 | 2-thienyl | 1 | methyl |
| 77 | 2-thienyl | 1 | methyl |
| 44 | 2-thienyl | 1 | methyl |
| 98 | 3-fluoro-4-methyl phenyl | 1 | methyl |
| 99 | 3-biphenyl | 1 | methyl |
| 103 | 3-thienyl | 1 | methyl |

TABLE 4

Representative Compounds of the Present Invention

| ID No. | Structure |
|---|---|
| 40 | 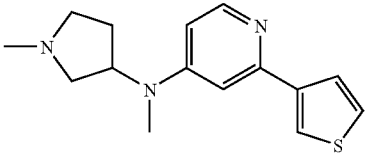 |
| 41 | 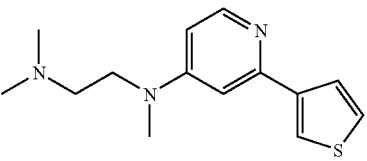 |
| 42 | 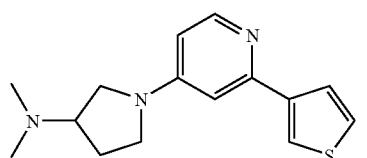 |
| 66 | 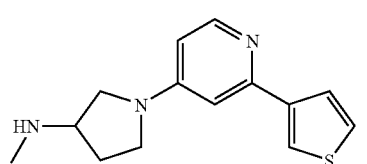 |

The present invention includes also pharmaceutically acceptable salts of the compounds as described herein (e.g., compounds of formula (I), compounds as listed in Table 3, compounds as listed in Table 4), for example, of those described above and of the specific compounds exemplified herein, and methods using such salts.

A "pharmaceutically acceptable salt" is intended to mean a salt of a free acid or base of any of the compounds described herein that is non-toxic, biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. The compounds of the present invention may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If a compound of the present invention contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid or phosphoric acid, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If a compound of the present invention is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds described herein, and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of the present invention). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of the present invention as described herein. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of the compounds of the present invention, as described herein, as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of the present invention, and uses of such metabolites in the methods of the invention. A "pharmaceutically active metabolite" means a pharmacologically active product of metabolism in the body of a compound of the present invention or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of the present invention and their pharmaceutically acceptable salts, pharmaceutically acceptable prodrugs, and pharmaceutically active metabolites (collectively, "active agents") of the present invention are useful as histamine $H_4$ receptor modulators in the methods of the invention. Such methods for modulating histamine $H_4$ receptor activity comprise exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit histamine $H_4$ receptor activity.

In some embodiments, the histamine $H_4$ receptor is in a subject with a disease, disorder, or medical condition mediated through modulation of the histamine $H_4$ receptor, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through histamine $H_4$ receptor activity, such as inflammation. Active agents according to the invention may therefore be used as an anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to any one of a plurality of conditions such as allergy, asthma, chronic obstructed pulmonary disease (COPD), atherosclerosis, rheumatoid arthritis, multiple sclerosis, inflammatory bowel diseases (including colitis, Crohn's disease, and ulcerative colitis), psoriasis, pruritus, itchy skin, atopic dermatitis, urticaria (hives), ocular inflammation (e.g., post-surgical ocular inflammation), conjunctivitis, dry eye, nasal polyps, allergic rhinitis, nasal itch, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritus treatable with a histamine $H_4$ receptor-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, asthma, autoimmune diseases, or pruritus.

Thus, the active agents may be used to treat subjects diagnosed with or suffering from a disease, disorder, or condition mediated through histamine $H_4$ receptor activity. The term "treat" or "treating" as used herein is intended to refer to administration of an active agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity.

The term "subject" as used herein, refers to an animal, for example, a mammal or a human, who has been the object of treatment, observation or experiment. In an embodiment, the subject has experienced and/or exhibited at least one symptom of the disease or disorder to be treated.

"Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

Embodiments of chemical entities according to this invention are $H_4$ receptor modulating chemical entities.

In treatment methods according to the invention, an effective amount of at least one active agent according to the invention is administered to a subject suffering from or diagnosed as having such a disease, disorder, or condition.

The term "effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of a disease or disorder. When referring to modulating the target receptor, an "effective amount" means an amount sufficient to at least affect the activity of such receptor. Measuring the activity of the target receptor may be performed by routine analytical methods. Target receptor modulation is useful in a variety of settings, including assays.

In addition, effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, or any range therein for example, about 0.01 to 100 mg/kg/day, or about 0.01 to 2.5 mg/kg daily, or any range therein, in single or divided dosage units (e.g., BID, TID, QID). For a 70-kg human, an illustrative range for a suitable dosage amount is from about 0.05 to about 7 g/day, or about 0.2 to about 2.5 g/day, or any range therein. In an example, the daily dosage is in the range of from about 0.05 to about 0.25 g per kg per day, or any range therein.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of the present invention or included with such an agent in a pharmaceutical composition according to the invention. In an exemplary embodiment, additional active ingredients are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

As used herein, the term "composition" is intended to encompass a product comprising the specified ingredients in the specified amounts, as well as any product which results, directly or indirectly, from combinations of the specified ingredients in the specified amounts.

The active agents of the invention are used, alone or in combination with one or more additional active ingredients, to formulate pharmaceutical compositions of the invention. A pharmaceutical composition of the invention comprises an effective amount of at least one active agent in accordance with the invention. As known in pharmaceutical technology, at least one pharmaceutically acceptable excipient may be comprised in embodiments of pharmaceutical compositions according to this invention.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. In an embodiment, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily, or any range therein.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol or sorbitol. Exemplary liquid oral excipients include ethanol, glycerol or water. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose or aluminum stearate gel); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to the compounds of the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. In an embodiment, wherein the compound is present as an enantiomer, the enantiomer is present at an enantiomeric excess of greater than or equal to about 80%. In another embodiment, the enantiomer is present at an enantiomeric excess of greater than or equal to about 90%. In another embodiment, the enantiomer is present at an enantiomeric excess of greater than or equal to about 95%. In another embodiment, the enantiomer is present at an enantiomeric excess of greater than or equal to about 98%. In another embodiment, the enantiomer is present at an enantiomeric excess of greater than or equal to about 99%. Similarly, wherein the compound is present as a diastereomer, the diastereomer is present at a diastereomeric excess of greater than or equal to about 80%. In an embodiment, the diastereomer is present at a diastereomeric excess of greater than or equal to about 90%. In another embodiment, the diastereomer is present at an diastereomeric excess of greater than or equal to about 95%. In another embodiment, the diastereomer is present at a diastereomeric excess of greater than or equal to about 98%. In another embodiment, the diastereomer is present at a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Compounds of formula (I) wherein moiety

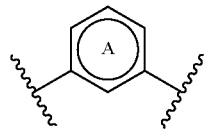

is

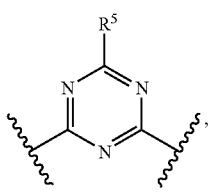

, may be prepared according to the process as outlined in Scheme 1 below.

Scheme 1

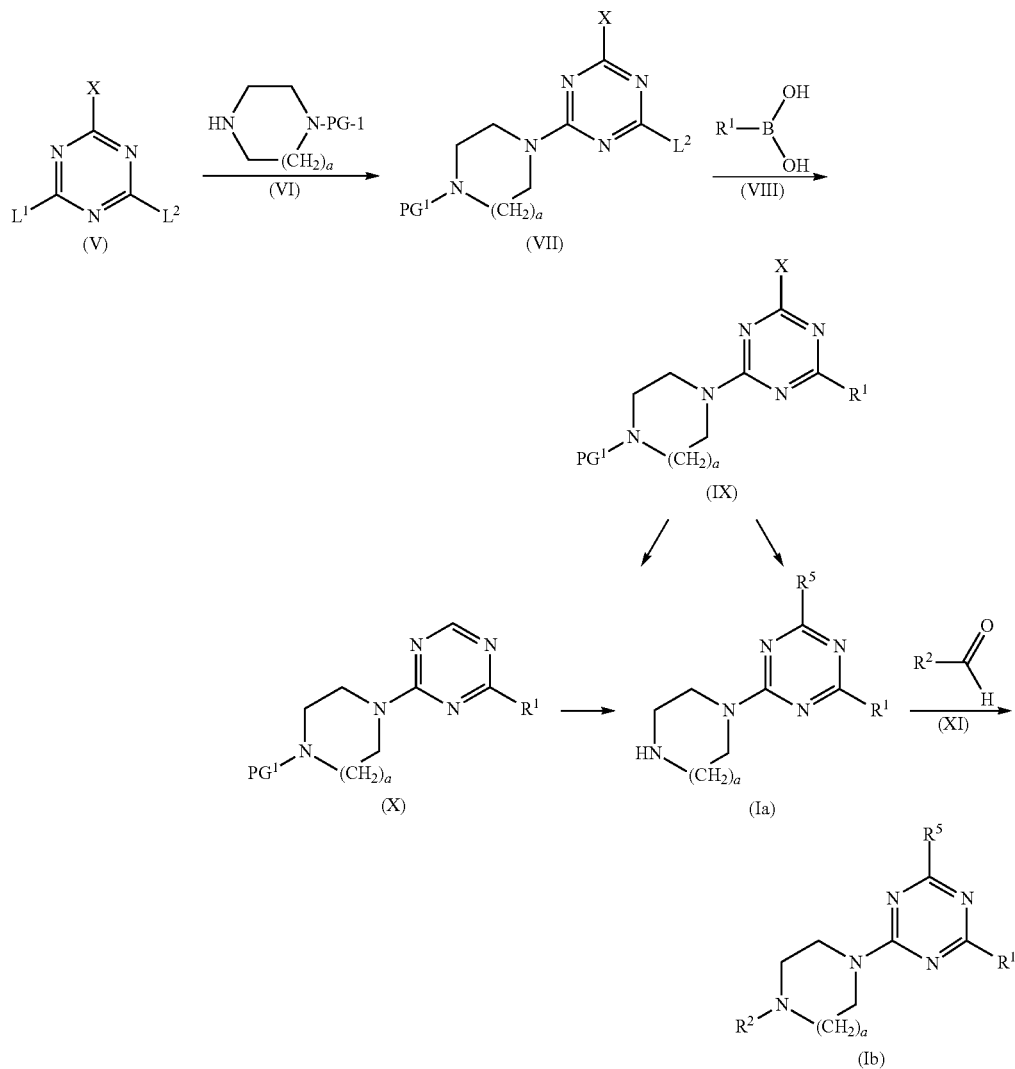

Accordingly, a suitably substituted compound of formula (V), wherein X is selected from the group consisting of halo and $C_{1-4}$alkyl, and wherein $L^1$ and $L^2$ are the same and are suitably selected leaving groups such as Cl, Br or I, a known compound or compound prepared by known methods, is reacted with a suitably selected compound of formula (VI), wherein $PG^1$ is suitably selected nitrogen protecting group such as BOC or CBz, a known compound or compound prepared by known methods, in the presence of an inorganic or tertiary organic base such as $Na_2CO_3$, $NaHCO_3$, TEA, DIPEA or pyridine, in a polar aprotic organic solvent such as acetone, 1,4-dioxane or THF, at a temperature in the range of from about −20° C. to about 0° C., to yield the corresponding compound of formula (VII).

The compound of formula (VII) is reacted with a suitably substituted boronic acid, a compound of formula (VIII), a known compound or compound prepared by known methods, in the presence of a suitably selected palladium catalyst such as $Pd(PPh_3)_4$, tris(dibenzylideneacetone) dipalladium (0) and/or $Pd(P^t\text{-}Bu_3)_2$, and in the presence of a base such as KF, CsF or $K_3PO_4$, in a polar organic solvent such as 1,4-dioxane, THF or DMF, at a temperature in the range of from about 25° C. to about 150° C., to yield the corresponding compound of formula (IX).

Wherein the compound of formula (IX) X is halo, the compound of formula (IX) is reacted with $H_2$ gas in the presence of a catalyst such as 10% Pd/C powder, in an organic solvent such as methanol, ethanol, isopropanol or ethyl acetate, at a temperature in the range of from about 25° C. to about 100° C., to yield the corresponding compound of formula (X).

The compound of formula (X) is then de-protected according to known methods, to yield the corresponding compound of formula (Ia). For example, wherein $PG^1$ is BOC, the compound of formula (X) is de-protected by reacting with an acid such as TFA or HCl, in an organic solvent such as DCM or DCE, to yield the corresponding compound of formula (Ia), wherein $R^5$ is H.

Alternatively, wherein the compound of formula (IX) X is halo or $C_{1-4}$alkyl, the compound of (IX) is de-protected according to known methods, to yield the corresponding compound of formula (Ia), wherein $R^5$ is the corresponding halo or $C_{1-4}$alkyl. For example, wherein $PG^1$ is BOC, the compound of formula (X) is de-protected by reacting with an acid such as TFA or HCl, in an organic solvent such as DCM or DCE.

The compound of formula (Ia) is further, optionally reacted with a suitably substituted aldehyde, a compound of formula (XI), a known compound or compound prepared by known methods, in the presence of a suitably selected reducing agent such as sodium triacetoxyborohydride, sodium cyanoborohydride or sodium borohydride, in an organic solvent such as methanol, ethanol or DCM, at a temperature in the range of from about 0° C. to about 50° C., to yield the corresponding compound of formula (Ib).

Compounds of formula (I) wherein moiety

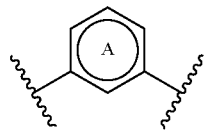

is

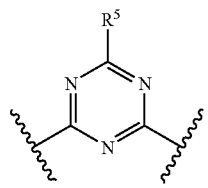

may alternatively be prepared according to the process outlined in Scheme 2, below.

Accordingly, a suitably substituted compound of formula (XII), a known compound or compound prepared by known methods, is reacted with S-methylisothiourea sulfate, a known compound, in water, at a temperature in the range of from about 0° C. to about 50° C. (for example, at room temperature), to yield the corresponding compound of formula (XIII). As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

A suitably substituted compound of formula (XIV), a known compound or compound prepared by known methods, is reacted with a suitably substituted compound of formula (XVI), wherein A is selected from the group consisting of H and $C_{1-4}$alkyl (for example, methyl or ethyl), such as N,N-dimethylformamide dimethyl acetal, a known compound or compound prepared by known methods, at a temperature in the range of from about 50° C. to about 100° C. (for example, at about 80-85° C.), to yield the corresponding compound of formula (XV). One skilled in the art will recognize that in the reaction of the compound of formula (XIV) with the compound of formula (XVI), the compound of formula (XVI) acts as the solvent, and therefore the reaction is run neat.

The compound of formula (XIII) is reacted with the compound of formula (XV) in an anhydrous organic solvent such as 1,4-dioxane, THF, acetonitrile, DME or polar aprotic organic solvent of similar dielectric constant, at a temperature in the range of from about 50° C. to about 150° C. (for example at the selected solvent reflux temperature), to yield the corresponding compound of formula (Ic). Further embodiments of solvents in which reactions according to this invention are performed include chemically compatible mixtures of solvents that are illustratively referred to herein. This reacting of compound of formula (XIII) with compound of formula (XV) is run in the presence of an inorganic base, when compound of formula (XIII) is obtained from compound of formula (XII) and an S-methylisothiourea sulfate, wherein the inorganic base is capable of neutralizing the acidic sulfate generated in the reaction of the compound of formula (XII) with the S-methylisothiourea sulfate. Bases

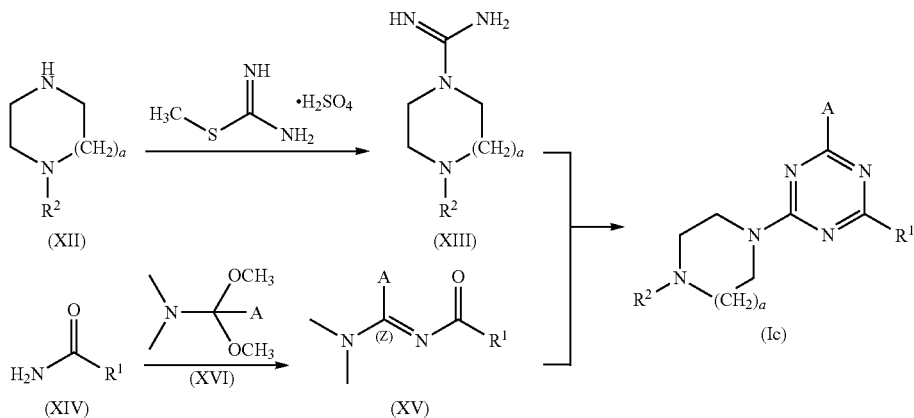

Scheme 2 such as KOt-Bu, NaOt-Bu, NaH, KH, and chemically compatible mixtures of such bases are examples of such inorganic bases, One skilled in the art will recognize that the compounds of formula (Ic) are compounds of formula (Ia) wherein $R^5$ is selected from the group consisting of H and $C_{1-4}$alkyl.

Compounds of formula (I) wherein moiety

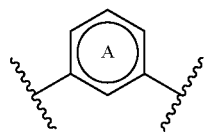

is

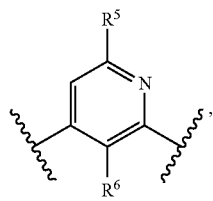

may be prepared according to the process outlined in Scheme 3, below.

known methods, in the presence of a suitably selected palladium catalyst such as $Pd(PPh_3)_4$, $Pd(PPh_3)_2Cl_2$, $Pd(P^tBu_3)_2$ or $Pd(OAc)_2$, in combination with a suitable selected ligand such as dppf and 2(di-t-butylphosphino)biphenyl; in the presence of an inorganic base such as $Na_2CO_3$, $NaHCO_3$, $K_2CO_3$, $Cs_2CO_3$ or KF; in an organic solvent such as DME, toluene, methanol, ethanol or DMF, at a temperature in the range of from about 50° C. to about 150° C., to yield the corresponding compound of formula (XXI).

The compound of formula (XXI) is reacted with a suitably substituted compound of formula (XII), a known compound or compound prepared by known methods, in a polar organic solvent such as ethanol or isopropanol, at a temperature in the range of from about 100° C. to about 200° C., to yield the corresponding compound of formula (Id).

One skilled in the art will recognize that in the reaction of the compound of formula (XXI) with the compound of formula (XII), the reaction mixture may be heated by microwave, according to known methods, as described in more detail in the Examples which follow herein.

Compounds of formula (I) wherein moiety

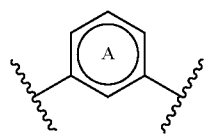

is

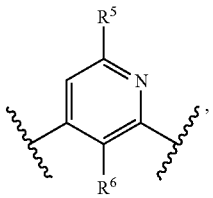

may alternatively be prepared according to the process outlined in Scheme 4, below.

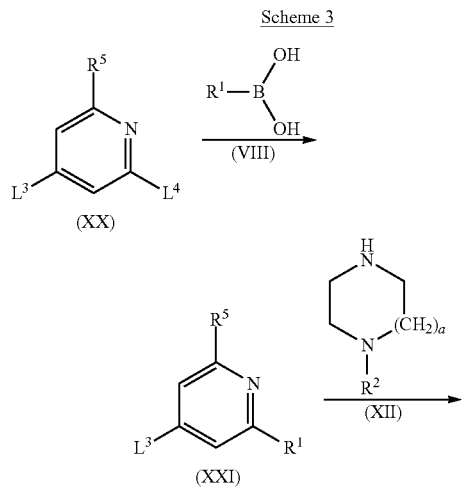

Accordingly, a suitably substituted compound of formula (XX), wherein $L^3$ and $L^4$ are the same and are suitably selected leaving groups such as Cl, Br or I, a known compound or compound prepared by known methods, is reacted with a suitably substituted boronic acid, a compound of formula (VIII), a known compound or compound prepared by

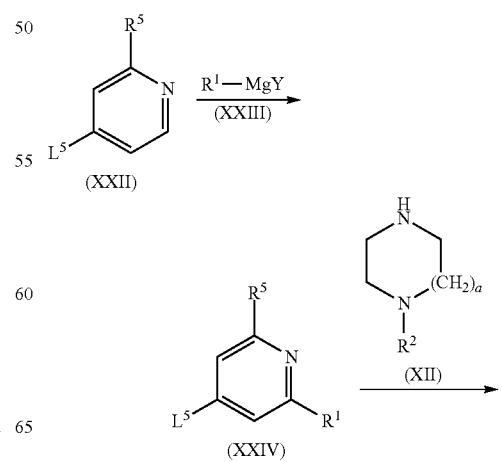

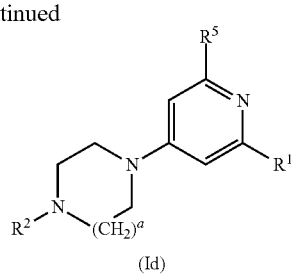

(Id)

Accordingly, a suitably substituted compound of formula (XXII), wherein $L^5$ is a suitably selected leaving groups such as Cl, Br or I, a known compound or compound prepared by known methods, is reacted with a suitably substituted compound of formula (XXIII), wherein Y is a suitably selected halide such as bromide, chloride or iodide, a known compound or compound prepared by known methods, in the presence of a suitably selected chloroformate such as phenyl chloroformate or methyl chloroformate, in an anhydrous organic solvent, such as THF or diethyl ether, at a temperature in the range of from about −78° C. to about 25° C., followed by treatment with a suitably selected oxidizing agent such as o-chloroanil or DDQ, in an organic solvent or mixture of organic solvents such as 1:1 mixture of toluene/acetic acid or a 1:1 mixture of benzene/acetic acid, at a temperature in the range of from about 0° C. to about 25° C., to yield the corresponding compound of formula (XXIV) (See for example, Journal of Organic Chemistry, 1985, 50(22), pp 4410-4411)

The compound of formula (XXIV) is reacted with a suitably substituted compound of formula (XII), a known compound or compound prepared by known methods, in a polar organic solvent such as ethanol or isopropanol, at a temperature in the range of from about 100° C. to about 200° C., to yield the corresponding compound of formula (Id).

One skilled in the art will recognize that in the reaction of the compound of formula (XXI) with the compound of formula (XII), the reaction mixture may be heated by microwave, according to known methods, as described in more detail in the Examples which follow herein.

Compounds of formula (I) wherein $R^1$ is aryl or heteroaryl, and wherein the aryl or heteroaryl is substituted with one or more substituents, may alternatively be prepared from the corresponding compound of formula (I) wherein the $R^1$ is an unsubstituted aryl or heteroaryl, according to known methods. For example, a compound of formula (I) wherein $R^1$ is unsubstituted aryl or heteroaryl may be reacted with a suitably selected brominating agent or chlorinating agent, according to known methods, to yield the corresponding bromo-substituted compound. Examples 47 and 52 which follows herein provide representative examples of such a process.

Alternatively, compounds of formula (I) wherein $R^1$ is aryl or heteroaryl, and wherein the aryl or heteroaryl is substituted with one or more substituents, may alternatively be prepared from the corresponding compound of formula (I) wherein the $R^1$ is a hydroxy substituted aryl or heteroaryl, and wherein the hydroxy group is present at the position of the desired substitution. For example, the compound of formula (I) wherein $R^1$ is a hydroxy substituted aryl or heteroaryl may be reacted with trimethanesulfonic anhydride, according to known methods, and then further reacted with a suitably substituted boronic acid, according to known methods, to yield the corresponding substituted compound. Example 53 which follows herein provides a representative example of this process.

Alternatively still, compounds of formula (I) wherein $R^1$ is aryl or heteroaryl, and wherein the aryl or heteroaryl is substituted with one or more substituents, may alternatively be prepared from the corresponding compound of formula (I) wherein the $R^1$ is a carboxy substituted aryl or heteroaryl, and wherein the carboxy group is present at the position of the desired substitution. For example, the compound of formula (I) wherein $R^1$ is a carboxy substituted aryl or heteroaryl may be reacted with morpholine, according to known methods of amide bond formation, to yield the corresponding —C(O)-(4-morpholinyl) substituted compound. Example 63 which follows herein provides a representative example of this process.

One skilled in the art will recognize that other such transformation may be used in the preparation of the compounds of the present invention, according to known methods. Additional examples of such transformations are as described in Examples 100, 109, 120, 122, 125 and 128-132, which follow hereinafter.

Compounds of Formula (I) may be converted to their corresponding salts using methods described in the art. For example, amines of Formula (I) may be treated with trifluoroacetic acid, HCl, or citric acid in a solvent such as $Et_2O$, $CH_2Cl_2$, THF, and MeOH to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific Examples are set forth to illustrate the invention and to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum or a syrup.

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using EM Science silica gel 60 $F_{254}$ 2.5 cm×7.5 cm 250 μm pre-coated plates. Preparative thin-layer chromatography was performed using Analtech silica gel GF 2000 μm 20×20 cm pre-coated plates.

Normal phase flash column chromatography was typically performed with IST ISOLUTE® silica gel columns using solvents as indicated. Preparative HPLC was performed using a Gilson system (215 liquid handler, uv/vis-155, 333 and 334 pump) and Waters XTerra® Prep MS C$_8$ OBD™ Column (5 μm, 19×50 mm) using a gradient mixture of 0.1% aqueous formic acid and acetonitrile.

Mass spectra were obtained on a Finnigan AQA using electrospray ionization (ESI) in positive mode unless otherwise indicated. The "calculated" (calcd.) mass corresponds to the exact mass.

Nuclear magnetic resonance (NMR) spectra were obtained on either a Varian VXR-300S (300 MHz) or a Mercury Plus 400 (400 MHz) spectrometer. The format of the $^1$H NMR data below is: chemical shift in ppm down field of the tetramethylsilane reference (multiplicity, coupling constant J in Hz, integration).

Chemical names were generated using ChemDraw Version 6.0.2 (CambridgeSoft, Cambridge, Mass.).

EXAMPLE 1

2-(4-Methyl-piperazin-1-yl)-4-thiophen-3-yl-[1,3,5]triazine

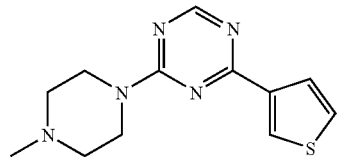

Step A: Preparation of 4-(4,6-Dichloro-[1,3,5]triazin-2-yl)-piperazine-1-carboxylic acid tert-butyl ester Cyanuric chloride (2.22 g, 12.0 mmol) in acetone (50 mL) was added to well-stirred ice water (72 mL). To the resulting fine slurry at 0° C. was slowly added a solution of 1-Boc-piperazine (2.24 g, 12.0 mmol) in acetone (20 mL). A solution of NaHCO$_3$ (1.0 g) in water (20 mL) was slowly added to the mixture, which was subsequently stirred at 0° C. for an additional 2.5 h. The resulting precipitate was collected by filtration, washed with water, and dried to yield a white solid, which was used without further purification.

$^1$H NMR (CDCl$_3$): 3.88-3.84 (m, 4H), 3.53-3.50 (m, 4H), 1.49 (s, 9H).

Step B: Preparation of 4-(4-Chloro-6-thiophen-3-yl-[1,3,5]triazin-2-yl)-piperazine-1-carboxylic acid tert-butyl ester To a solution of 4-(4,6-dichloro-[1,3,5]triazin-2-yl)-piperazine-1-carboxylic acid tert-butyl ester (167.1 mg, 0.5 mmol) in anhydrous 1,4-dioxane (4 mL) in an oven-dried flask was added 3-thiopheneboronic acid (70.4 mg, 0.55 mmol), Pd[P(t-Bu)$_3$]$_2$ (2.5 mg, 0.005 mmol), tris(dibenzylideneacetone)-dipalladium(0) (2.3 mg, 0.0025 mmol), and KF (64 mg, 1.1 mmol). The resulting mixture was vacuum flushed with argon and heated overnight at 90° C. The reaction mixture was cooled and passed through a pad of diatomaceous earth, washing with EtOAc. The filtrate was concentrated and the residue was purified by preparative TLC (EtOAc/hexanes, 1:4) to yield a white solid, which was used without further purification.

$^1$H NMR (CDCl$_3$; 65% purity): 8.44 (dd, J=3.1, 1.1, 1H), 7.92 (dd, J=5.1, 1.1, 1H), 7.36 (dd, J=5.1, 3.1, 1H), 4.02-3.98 (m, 4H), 3.57-3.54 (m, 4H), 1.51 (s, 9H).

Step C: Preparation of 4-(4-Thiophen-3-yl-[1,3,5]triazin-2-yl)-piperazine-1-carboxylic acid tert-butyl ester To a solution of 4-(4-chloro-6-thiophen-3-yl-[1,3,5]triazin-2-yl)-piperazine-1-carboxylic acid tert-butyl ester (169 mg, 0.29 mmol) in 2-propanol/EtOAc (10:1, 11 mL) at room temperature was added DIEA (0.5 mL). The resulting solution was vacuum-flushed with N$_2$ and then treated with 10% Pd/C (50 mg). The resulting suspension was exposed to H$_2$ via balloon and heated to 65° C. After 3 h, 10% Pd/C (50 mg) was added, and the reaction mixture was heated at 65° C. overnight under H$_2$. The resulting mixture was filtered to remove catalyst; the filtrate was concentrated and the residue was purified by preparative TLC (EtOAc/hexanes, 1:2) to yield a white solid.

LC/MS: mass calcd. for C$_{16}$H$_{21}$N$_5$O$_2$S, 347.1; m/z found, 348.2 [M+H]$^+$ $^1$H NMR (CDCl$_3$): 8.59 (s, 1H), 8.38 (d, J=2.8, 1H), 7.82 (dd, J=5.1, 1.0, 1H), 7.35 (dd, J=5.1, 3.1, 1H), 3.91 (br s, 4H), 3.52 (br s, 4H), 1.49 (s, 9H).

Step D: Preparation of 2-piperazin-1-yl-4-thiophen-3-yl-[1,3,5]triazine

To a 0° C. solution of 4-(4-thiophen-3-yl-[1,3,5]triazin-2-yl)-piperazine-1-carboxylic acid tert-butyl ester (60 mg, 0.17 mmol) in CH$_2$Cl$_2$ (2 mL) was added TFA (1 mL) dropwise. The resulting solution was allowed to warm to room temperature and stirred overnight. The resulting mixture was concentrated, then re-dissolved in CH$_2$Cl$_2$ and concentrated. The residue was dissolved in a mixture of CH$_2$Cl$_2$/MeOH (4:1, 5 mL), neutralized with Na$_2$CO$_3$, and stirred at room temperature for 30 min. The resulting solid was filtered, washed with CH$_2$Cl$_2$, and the filtrate was concentrated to yield a yellow gummy solid, which was used without purification.

LC/MS: mass calcd. for C$_{11}$H$_{13}$N$_5$S, 247.1; m/z found, 248.2 [M+H]$^+$

Step E. Preparation of Title Compound

To a solution of 2-piperazin-1-yl-4-thiophen-3-yl-[1,3,5]triazine (0.17 mmol) in CH$_2$Cl$_2$/MeOH (3:1, 4 mL) was added formaldehyde (37 wt. % in water, 22 mg, 0.26 mmol). After stirring for 1 h at room temperature, NaB(OAc)$_3$H (72.8 mg, 0.34 mmol) was added. The reaction mixture was stirred overnight at room temperature, then quenched with 1 N NaOH (3 mL), and extracted with EtOAc (50 mL). The organic layer was washed with water (2×15 mL), brine (15 mL), dried, and concentrated to yield a light yellow oil.

LC/MS: mass calcd. for C$_{12}$H$_{15}$N$_5$S, 261.1; m/z found, 262.1 [M+H]$^+$ $^1$H NMR (CDCl$_3$): 8.56 (s, 1H), 8.33 (dd, J=3.1, 1.1, 1H), 7.81 (dd, J=5.1, 1.1, 1H), 7.33 (dd, J=5.1, 3.1, 1H), 3.98-3.92 (br m, 4H), 2.49-2.46 (m, 4H), 2.34 (s, 3H).

Additional representative compounds of the present invention, as listed in Example 2-8 below, were prepared according to the methods described in Example 1, above substituting a suitably substituted boronic acid for the 3-thiopheneboronic acid reagent. Additional substitutions and/or changes in reaction conditions, when present, were as described for each Example as noted.

EXAMPLE 2

2-(4-Methyl-piperazin-1-yl)-4-thiophen-2-yl-[1,3,5]triazine

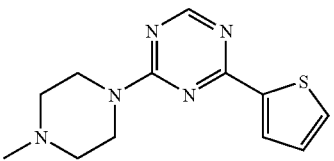

LC/MS: mass calcd. for $C_{12}H_{15}N_5S$, 261.1; m/z found, 262.1 $[M+H]^+$ $^1$H NMR (CDCl$_3$): 8.54 (s, 1H), 8.04 (d, J=3.7, 1H), 7.52 (d, J=5.0, 1H), 7.14 (t, J=4.3, 1H), 4.00-3.93 (m, 4H), 2.50 (br s, 4H), 2.36 (s, 3H).

EXAMPLE 3

2-(3-Fluoro-4-methyl-phenyl)-4-(4-methyl-piperazin-1-yl)-[1,3,5]triazine

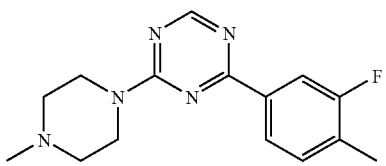

The title compound was prepared according to the methods as described in Example 1 with the following substitutions: Pd(PPh$_3$)$_4$ was used as the Pd source and K$_3$PO$_4$ was used in place of KF.

LC/MS: mass calcd. for $C_{15}H_{18}FN_5$, 287.2; m/z found, 288.2 $[M+H]^+$.

$^1$H NMR (CDCl$_3$): 8.61 (s, 1H), 8.07 (dd, J=15.4, 1.6, 1H), 8.04 (dd, J=18.4, 1.6, 1H) 7.26 (t, J=15.3, 1H), 4.04 (br s, 2H), 3.95 (br s, 2H), 2.51 (br s, 4H), 2.37 (s, 3H), 2.34 (d, J=1.9, 3H).

EXAMPLE 4

2-(4-Methyl-piperazin-1-yl)-4-D-tolyl-[1,3,5]triazine

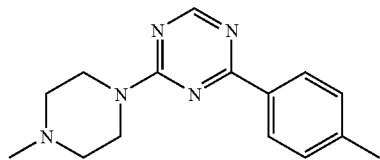

LC/MS: mass calcd. for $C_{15}H_{19}N_5$, 269.2; m/z found, 270.2 $[M+H]^+$ $^1$H NMR (CDCl$_3$): 8.62 (s, 1H), 8.30 (d, J=8.3, 2H), 7.27 (d, J=8.0, 2H), 4.04 (br s, 2H), 3.95 (br s, 2H), 2.50 (br s, 4H), 2.42 (s, 3H), 2.36 (s, 3H).

EXAMPLE 5

2-(3,4-Difluoro-phenyl)-4-(4-methyl-piperazin-1-yl)-[1,3,5]triazine

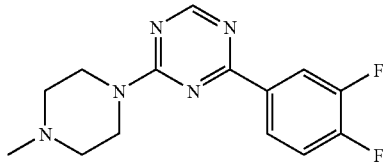

LC/MS: mass calcd. for $C_{14}H_{15}F_2N_5$, 291.1; m/z found, 292.2 [M H]$^+$ $^1$H NMR (CDCl$_3$): 8.60 (s, 1H), 8.27-8.16 (m, 2H), 7.27-7.19 (m, 1H), 4.02 (br s, 2H), 3.94 (br s, 2H), 2.49 (br s, 4H), 2.36 (s, 3H).

EXAMPLE 6

2-Furan-3-yl-4-(4-methyl-piperazin-1-yl)-[1,3,5]triazine

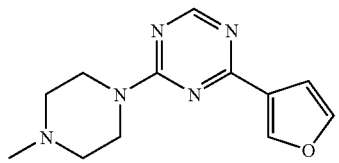

LC/MS: mass calcd. for $C_{12}H_{15}N_5O$, 245.1; m/z found, 246.2 $[M+H]^+$ $^1$H NMR (CDCl$_3$): 8.52 (s, 1H), 8.25 (s, 1H), 7.47 (t, J=1.7, 1H), 6.98 (d, J=1.8, 1H), 3.95 (br s, 4H), 2.50-2.46 (m, 4H), 2.35 (s, 3H).

EXAMPLE 7

2-(3-Fluoro-phenyl)-4-(4-methyl-piperazin-1-yl)-[1,3,5]triazine

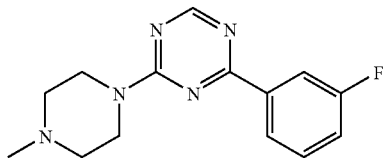

LC/MS: mass calcd. for $C_{14}H_{16}FN_5$, 273.1; m/z found, 274.3 [M+H]$^+$ $^1$H NMR (CDCl$_3$): 8.64 (s, 1H), 8.21 (d, J=7.8, 1H), 8.12-8.08 (m, 1H), 7.47-7.40 (m, 1H), 7.25-7.18 (m, 1H), 4.04 (br s, 2H), 3.96 (br s, 2H), 2.50 (br s, 4H), 2.36 (s, 3H).

EXAMPLE 8

2-(4-Methyl-piperazin-1-yl)-4-(3-trifluoromethyl-phenyl)-[1,3,5]triazine

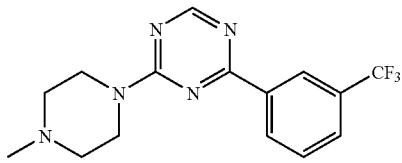

LC/MS: mass calcd. for $C_{15}H_{16}F_3N_5$, 323.1; m/z found, 324.2 [M+H]$^+$ $^1$H NMR (CDCl$_3$): 8.67 (s, 1H), 8.65 (s, 1H), 8.60 (d, J=7.9, 1H), 7.77 (d, J=7.8, 1H), 7.59 (t, J=7.8, 1H), 4.05 (br s, 2H), 3.96 (br s, 2H), 2.51 (br s, 4H), 2.36 (s, 3H).

EXAMPLE 9

2-(4-Bromo-thiophen-2-yl)-4-(4-methyl-piperazin-1-yl)-[1,3,5]triazine

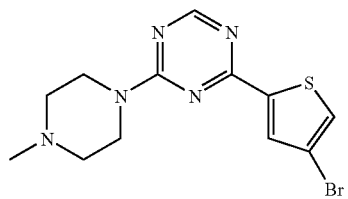

Step A: Preparation of 4-Methyl-piperazine-1-carboxamidine sulfate

To a solution of S-methylisothiourea sulfate (2.78 g, 10.0 mmol) in distilled water (20 mL) was added 1-methylpiperazine (2.22 mL, 20 mmol). After stirring for 48 h at room temperature, the solution was concentrated to approximately 5 mL and treated with EtOH (10 mL). The resulting solid was collected by filtration, washed with EtOH, and dried to yield 4-methyl-piperazine-1-carboxamidine sulfate as a colorless solid. Further concentration of the mother liquor yielded a second crop or the material.

LC/MS: mass calcd. for $C_6H_{14}N_4$, 142.1; m/z found, 184.3 [M+H+CH$_3$CN]$^+$ $^1$H NMR (D$_2$O): 3.32-3.29 (m, 4H), 2.40-2.38 (m, 4H), 2.12 (s, 3H).

Step B: Preparation of 4-Bromo-thiophene-2-carboxylic acid amide

To a suspension of saturated (satd.) aqueous (NH$_4$)$_2$CO$_3$ (5 mL) in 1,4-dioxane (3 mL) was slowly added a solution of 4-bromo-2-thiophenecarbonyl chloride (1.0 g, 4.43 mmol) in 1,4-dioxane (1 mL). The resulting mixture was cooled to 0° C., then was allowed to slowly warm to room temperature and was stirred for 2.5 h. The resulting mixture was poured into water (70 mL), treated with 1 N NaOH (5 mL), and stirred at room temperature for 1 h. The resulting precipitate was collected by filtration and washed with water. The white solid was dissolved in EtOAc (60 mL) and sequentially washed with 1 N NaOH (2×15 mL), water (2×15 mL), and brine (30 mL). The organic layer was dried and concentrated to yield 4-bromo-thiophene-2-carboxylic acid amide as and off-white solid.

$^1$H NMR (CDCl$_3$): 7.43 (d, J=1.3, 1H), 7.41 (d, J=1.3, 1H), 5.75 (br s, 2H).

Step C: Preparation of 4-Bromo-thiophene-2-carboxylic acid dimethylaminomethyleneamide A mixture of 4-bromo-thiophene-2-carboxylic acid amide (206 mg, 1.0 mmol) and N,N-dimethylformamide dimethyl acetal (0.5 mL, 3.8 mmol) was heated at 85° C. for 1.5 h. The resulting mixture was cooled, and then concentrated under high vacuum to yield 4-bromo-thiophene-2-carboxylic acid dimethylaminomethyleneamide as a light tan solid, which was directly used in the next step without purification.

$^1$H NMR (CDCl$_3$): 8.59 (s, 1H), 7.76 (d, J=1.5, 1H) 7.37 (d, J=1.5, 1H), 3.19 (s, 6H).

Step D: Preparation of the Title Compound

To a solution of 4-bromo-thiophene-2-carboxylic acid dimethylamino-methyleneamide (261 mg, 1.0 mmol) in anhydrous 1,4-dioxane (8 mL) was added 4-methyl-piperazine-1-carboxamidine sulfate (95.6 mg, 0.25 mmol) and KOtBu (56.1 mg, 0.5 mmol). The resulting suspension was heated at reflux overnight under argon. After cooling, the reaction mixture was passed through a pad of diatomaceous earth, the filtrate was concentrated and the residue was purified by preparative TLC (2 M NH$_3$ in MeOH/CH$_2$Cl$_2$) to yield the title compound as a yellowish solid.

LC/MS: mass calcd. for $C_{12}H_{14}BrN_5S$, 339.0; m/z found, 340.0 [M+H]$^+$ $^1$H NMR (CDCl$_3$): 8.52 (s, 1H), 7.92 (d, J=1.5, 1H), 7.40 (d, J=1.5, 1H), 3.96-3.92 (m, 4H), 2.48 (br s, 4H), 2.35 (s, 3H).

Additional representative compounds of the present invention, as listed in Example 10-24, 104, 107-108, 111-115, 117-119, 126-127, 133-136, 139-140, 143 and 147 below, were prepared according to the methods described in Example 9, above substituting a suitably substituted carboxamide for the 4-bromo-thiophene-2-carboxylic acid amide reagent. Additional substitutions and/or changes in reaction conditions, when present, were as described for each Example as noted.

EXAMPLE 10

2-(4-Bromo-phenyl)-4-(4-methyl-piperazin-1-yl)-[1,3,5]triazine

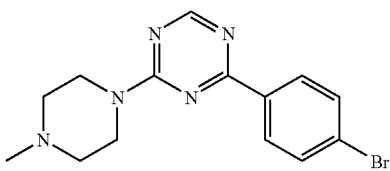

LC/MS: mass calcd. for $C_{14}H_{16}BrN_5$, 333.1; m/z found, 334.2 [M H]$^+$ $^1$H NMR (CDCl$_3$): 8.62 (s, 1H), 8.28 (d, J=8.5, 2H), 7.59 (d, J=8.5, 2H), 4.03 (br s, 2H), 3.95 (br s, 2H), 2.50 (br s, 4H), 2.36 (s, 3H).

EXAMPLE 11

2-(4-Methyl-piperazin-1-yl)-4-(3,4,5-trifluoro-phenyl)-[1,3,5]triazine

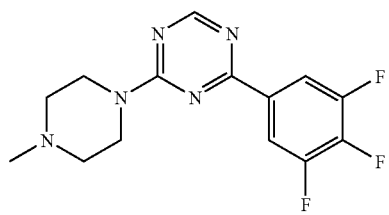

LC/MS: mass calcd. for $C_{14}H_{14}F_3N_5$, 309.1; m/z found, 310.3 [M+H]$^+$ $^1$H NMR (CDCl$_3$): 8.61 (s, 1H), 8.12-8.02 (m, 2H), 4.02 (br s, 2H), 3.95 (br s, 2H), 2.37 (s, 3H).

EXAMPLE 12

2-(4-Fluoro-phenyl)-4-(4-methyl-piperazin-1-yl)-[1,3,5]triazine

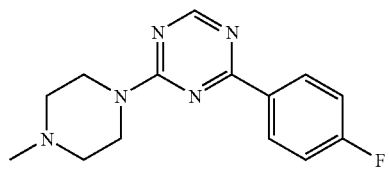

LC/MS: mass calcd. for $C_{14}H_{16}FN_5$, 273.1; m/z found, 274.3 [M+H]$^+$ $^1$H NMR (CDCl$_3$): 8.61 (s, 1H), 8.42 (dd, J=9.0, 5.6, 2H), 7.14 (t, J=17.5, 2H), 4.03 (br s, 2H), 3.95 (br s, 2H), 2.50 (br s, 4H), 2.36 (s, 3H).

EXAMPLE 13

2-(4-Chloro-phenyl)-4-(4-methyl-piperazin-1-yl)-[1,3,5]triazine

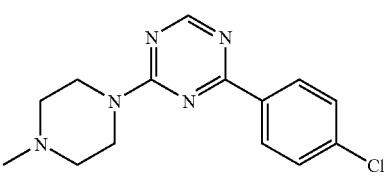

LC/MS: mass calcd. for $C_{14}H_{16}ClN_5$, 289.1; m/z found, 290.2 [M+H]$^+$ $^1$H NMR (CDCl$_3$): 8.62 (s, 1H), 8.37-8.33 (m, 2H), 7.45-7.41 (m, 2H), 4.04 (br s, 2H), 3.95 (br s, 2H), 2.50 (br s, 4H), 2.36 (s, 3H).

EXAMPLE 14

2-(3,4-Dichloro-phenyl)-4-(4-methyl-piperazin-1-yl)-[1,3,5]triazine

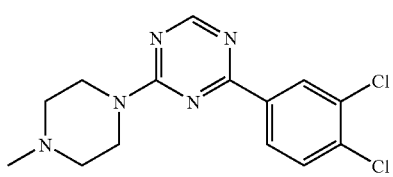

LC/MS: mass calcd. for $C_{14}H_{15}Cl_2N_5$, 323.1; m/z found, 324.2 [M+H]$^+$ $^1$H NMR (CDCl$_3$): 8.62 (s, 1H), 8.49 (d, J=2.0, 1H), 8.26-8.22 (m, 1H), 7.53 (d, J=8.4, 1H), 4.03 (br s, 2H), 3.95 (br s, 2H), 2.50 (br s, 4H), 2.36 (s, 3H).

EXAMPLE 15

2-(3-Bromo-thiophen-2-yl)-4-(4-methyl-piperazin-1-yl)-[1,3,5]triazine

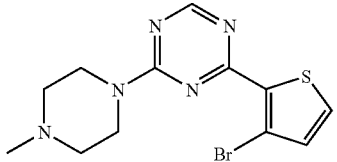

LC/MS: mass calcd. for $C_{12}H_{14}BrN_5S$, 339.0; m/z found, 340.2 [M+H]$^+$ $^1$H NMR (CDCl$_3$): 8.55 (s, 1H), 7.44 (d, J=5.3, 1H), 7.12 (d, J=5.3, 1H), 4.07-4.04 (m, 2H), 3.94-3.91 (m, 2H), 2.52-2.46 (m, 4H), 2.35 (s, 3H).

EXAMPLE 16

2-(6-Chloro-pyridin-3-yl)-4-(4-methyl-piperazin-1-yl)-[1,3,5]triazine

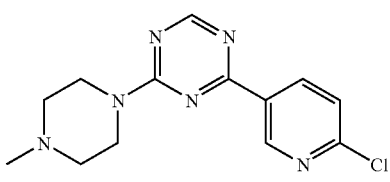

LC/MS: mass calcd. for $C_{13}H_{15}ClN_6$, 290.1; m/z found, 291.2 [M+H]$^+$ $^1$H NMR (CDCl$_3$): 9.34 (d, J=2.4, 1H), 8.65 (s, 1H), 8.60 (dd, J=8.4, 2.4, 1H), 7.43 (d, J=8.3, 1H), 4.08 (br s, 4H), 2.64 (br s, 4H), 2.48 (s, 3H).

EXAMPLE 17

2-(3-Chloro-thiophen-2-yl)-4-(4-methyl-piperazin-1-yl)-[1,3,5]triazine

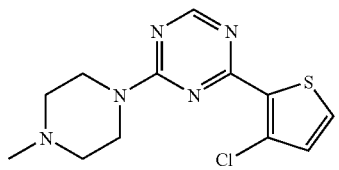

LC/MS: mass calcd. for $C_{12}H_{14}ClN_5S$, 295.1; m/z found, 296.1 [M+H]$^+$ $^1$H NMR (CDCl$_3$): 8.56 (s, 1H), 7.44 (d, J=5.3, 1H), 7.04 (d, J=5.3, 1H), 4.02 (br s, 2H), 3.93 (br s, 2H), 2.50 (br s, 4H), 2.3d (s, 3H).

EXAMPLE 18

2-(5-Bromo-thiophen-2-yl)-4-(4-methyl-piperazin-1-yl)-[1,3,5]triazine

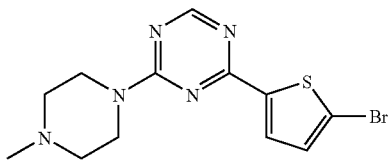

LC/MS: mass calcd. for $C_{12}H_{14}BrN_5S$, 339.0; m/z found, 340.0 [M+H]$^+$ $^1$H NMR (CDCl$_3$): 8.51 (s, 1H), 7.77 (d, J=4.0, 1H), 7.10 (d, J=4.0, 1H), 3.97 (br s, 4H), 2.53 (br s, 4H), 2.39 (s, 3H).

EXAMPLE 19

2-(4-Methyl-piperazin-1-yl)-4-pyridin-3-yl-[1,3,5]triazine

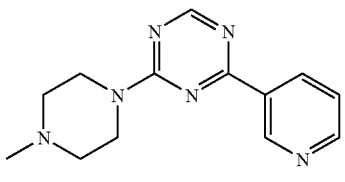

LC/MS: mass calcd. for $C_{13}H_{16}N_6$, 256.1; m/z found, 257.3 [M+H]$^+$ $^1$H NMR (CDCl$_3$): 9.58 (s, 1H), 8.74 (d, J=4.8, 1H), 8.65-8.61 (m, 1H), 8.64 (s, 1H), 7.39 (dd, J=7.9, 4.8, 1H), 4.03 (br s, 2H), 3.95 (br s, 2H), 2.50 (br s, 4H), 2.36 (s, 3H).

EXAMPLE 20

2-(4-Methyl-piperazin-1-yl)-4-pyridin-4-yl-[1,3,5]-triazine

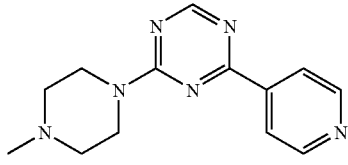

LC/MS: mass calcd. for $C_{13}H_{16}N_6$, 256.1; m/z found, 257.3 [M+H]$^+$ $^1$H NMR (CDCl$_3$): 8.75 (d, J=4.9, 2H), 8.66 (s, 1H), 8.20 (d, J=6.1, 2H), 4.03 (br s, 2H), 3.95 (br s, 2H), 2.49 (br s, 4H), 2.34 (s, 3H).

EXAMPLE 21

2-Benzo[b]thiophen-2-yl-4-(4-methyl-piperazin-1-yl)-[1,3,5]triazine

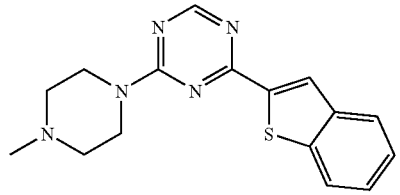

LC/MS: mass calcd. for $C_{16}H_{17}N_5S$, 311.1; m/z found, 312.3 [M+H]$^+$ $^1$H NMR (CDCl$_3$): 8.59 (s, 1H), 8.32 (s, 1H), 7.88-7.84 (m, 2H), 7.44-7.35 (m, 2H), 4.03 (br s, 2H), 3.94 (br s, 2H), 2.51 (br s, 4H), 2.36 (s, 3H).

EXAMPLE 22

2-(4-Methyl-piperazin-1-yl)-4-(5-methyl-2-trifluoromethyl-furan-3-yl)-[1,3,5]-triazine

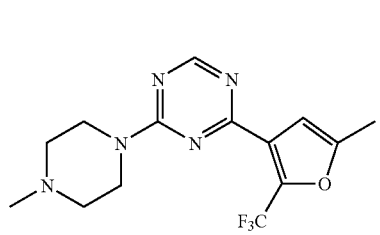

LC/MS: mass calcd. for $C_{14}H_{16}F_3N_5O$, 327.1; m/z found, 328.1 [M+H]$^+$ $^1$H NMR (CDCl$_3$): 8.57 (s, 1H), 6.70 (s, 1H), 3.93 (br s, 4H), 2.48-2.46 (m, 4H), 2.37 (s, 3H), 2.34 (s, 3H).

EXAMPLE 23

2-(3-Bromo-thiophen-2-yl)-4-methyl-6-(4-methyl-piperazin-1-yl)-[1,3,5]triazine

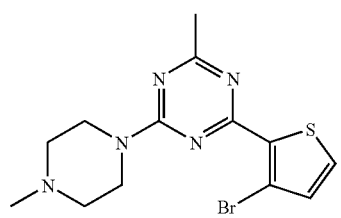

The title compound was prepared according to the methods as described in Example 9 with the following substitution: N,N-dimethylacetamide dimethyl acetal was used in place of N,N-dimethylformamide dimethyl acetal.

LC/MS: mass calcd. for $C_{13}H_{16}BrN_5S$, 353.0; m/z found, 354.0 [M+H]$^+$ $^1$H NMR (CDCl$_3$): 7.41 (d, J=5.3, 1H), 7.11 (d, J=5.3, 1H), 4.08 (br s, 2H), 3.98 (br s, 2H), 2.54 (br s, 4H), 2.45 (s, 3H), 2.38 (s, 3H).

EXAMPLE 24

1-[4-(3-Bromo-thiophen-2-yl)-[1,3,5]triazin-2-yl]-4-methyl-[1,4]diazepane

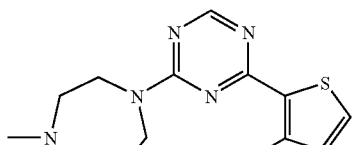

The title compound was prepared according to the methods as described in Example 9 with the following substitution: 1-Methyl-[1,4]diazepane was used in place of 1-methylpiperazine.

LC/MS: mass calcd. for $C_{13}H_{16}BrN_5S$, 353.0; m/z found, 354.0 [M+H]$^+$ $^1$H NMR (CDCl$_3$): 8.57 (d, J=4.7, 1H), 7.44 (dd, J=5.3, 1.3, 1H), 7.13 (dd, J=5.3, 0.6, 1H), 4.11-3.87 (br m, 4H), 2.82-2.64 (br m, 4H), 2.43 (s, 3H), 2.09 (br s, 2H).

EXAMPLE 25

2-(5-Chloro-thiophen-2-yl)-4-(4-methyl-piperazin-1-yl)-[1,3,5]triazine

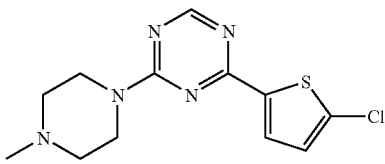

A mixture of 2-(5-bromo-thiophen-2-yl)-4-(4-methyl-piperazin-1-yl)-[1,3,5]triazine (6.8 mg, 0.02 mmol) and copper (I) chloride (4.0 mg, 0.04 mmol) in anhydrous DMF (5 mL) was heated at reflux for 20 h. NH$_4$OH solution (28% in water, 5 mL) was added and the resulting mixture was stirred at room temperature for 1 h. The resulting mixture was concentrated, diluted with EtOAc (30 mL), and washed sequentially with water (2×10 mL) and brine (10 mL). The organic layer was dried and concentrated, and the residue was purified by preparative HPLC to yield the title compound as a yellowish solid.

LC/MS: mass calcd. for $C_{12}H_{14}ClN_5S$, 295.0; m/z found, 296.0 [M+H]$^+$ $^1$H NMR (CDCl$_3$): 8.45 (s, 1H), 7.75 (d, J=4.0, 1H), 6.89 (d, J=4.0, 1H), 3.94 (br s, 4H), 2.53 (br s, 4H), 2.37 (s, 3H).

EXAMPLE 26

1-Methyl-4-(2-thiophen-3-yl-pyridin-4-yl)-piperazine

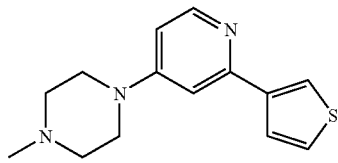

Step A: Preparation of 4-Chloro-2-thiophen-3-yl-Pyridine

To a N$_2$ flushed vial was added 2,4-dichloropyridine (149 mg, 1 mmol), Pd(PPh$_3$)$_4$ (30 mg, 3%), and toluene/EtOH (4:1, 3 mL). After stirring at room temperature for 5 min, 3-thiopheneboronic acid (128 mg, 1 mmol) and 2 M aqueous K$_2$CO$_3$ (1 mL) were added, and the resulting mixture was heated at 90° C. for 16 h. The resulting mixture was poured into water and extracted with EtOAc. The organic layer was dried and concentrated, and the residue was purified by preparative TLC (hexanes/EtOAc) to yield 4-chloro-r-thiophen-3-yl-pyridine as a white solid.

$^1$H NMR (CDCl$_3$): 8.51 (dd, J=5.3, 0.5, 1H), 7.92 (dd, J=3.0, 1.3, 1H), 7.64-7.61 (m, 2H), 7.41 (dd, J=5.1, 3.0, 1H), 7.18 (dd, J=5.3, 1.9, 1H).

Step B: Preparation of the Title Compound

To a microwave tube was added 4-chloro-2-thiophen-3-yl-pyridine (50 mg, 0.26 mmol), 1-methylpiperazine (100 mg, 1 mmol), 2-propanol (0.7 mL) and concentrated HCl (1 drop). The resulting mixture was heated at 180° C. for 40 min using a Personal Chemistry Smith Synthesizer. The resulting mixture was poured into water and extracted with CH$_2$Cl$_2$. The organic layer was dried and concentrated, and the residue was purified by preparative TLC (CH$_2$Cl$_2$/MeOH) to yield the title compound as a solid.

LC/MS: mass calcd. for C$_{14}$H$_{17}$N$_3$S, 259.1; m/z found, 260.1 [M+H]$^+$ $^1$H NMR (CDCl$_3$): 8.30 (d, J=6.0, 1H), 7.83 (dd, J=3.0, 1.2, 1H), 7.59 (dd, J=5.0, 1.2, 1H), 7.36 (dd, J=5.0, 3.0, 1H), 7.00 (d, J=2.5, 1H), 6.58 (dd, J=6.0, 2.5, 1H), 3.40 (t, J=5.2, 4H), 2.55 (t, J=5.2, 4H), 2.36 (s, 3H).

Additional representative compounds of the present invention, as listed in Example 27-46, 77-93, 123-124, 138, 145-146 and 148 below, were prepared according to the methods described in Example 26, above substituting a suitably substituted boronic acid for the 3-thiopheneboronic acid reagent and further substituting a suitably substituted amine for the 1-methylpiperazine reagent. Additional substitutions and/or changes in reaction conditions, when present, were as described for each Example as noted.

EXAMPLE 27

1-(2-Furan-2-yl-pyridin-4-yl)-4-methyl-piperazine

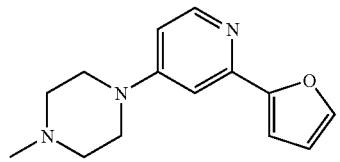

LC/MS: mass calcd. for C$_{14}$H$_{17}$N$_3$O, 243.1; m/z found, 244.1 [M+H]$^+$ $^1$H NMR (CDCl$_3$): 8.25 (d, J=6.0, 1H), 7.47 (dd, J=1.6, 0.8, 1H), 7.11 (d, J=2.6, 1H), 7.00 (dd, J=3.4, 0.8, 1H), 6.57 (dd, J=6.0, 2.6, 1H), 6.49 (dd, J=3.4, 1.6, 1H), 3.39 (t, J=5.2, 4H), 2.52 (t, J=5.2, 4H), 2.33 (s, 3H).

EXAMPLE 28

1-(2-Furan-3-yl-pyridin-4-yl)-4-methyl-piperazine

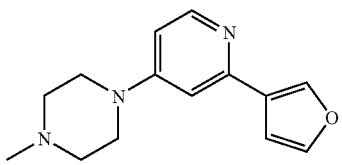

LC/MS: mass calcd. for C$_{14}$H$_{17}$N$_3$O, 243.1; m/z found, 244.2 [M+H]$^+$ $^1$H NMR (CDCl$_3$): 8.26 (d, J=6.0, 1H), 7.98 (dd, J=1.6, 0.8, 1H), 7.47 (t, J=1.6, 1H), 6.84-6.83 (m, 2H), 6.57 (dd, J=6.0, 2.4, 1H), 3.39 (t, J=5.2, 4H), 2.54 (t, J=5.2, 4H), 2.36 (s, 3H).

EXAMPLE 29

1-Methyl-4-[2-(4-methyl-thiophen-3-yl)-pyridin-4-yl]-piperazine

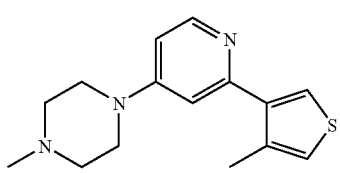

LC/MS: mass calcd. for C$_{15}$H$_{19}$N$_3$S, 273.1; m/z found, 274.2 [M+H]$^+$ $^1$H NMR (CDCl$_3$): 8.34 (br s, 1H), 7.48 (d, J=3.3, 1H), 7.00 (dd, J=3.3, 1.0, 1H), 6.84 (br s, 1H), 6.62 (dd, J=5.9, 2.5, 1H), 3.38 (t, J=5.2, 4H), 2.54 (t, J=5.2, 4H), 2.38 (d, J=1.0, 3H), 2.35 (s, 3H).

EXAMPLE 30

1-[2-(3-Chloro-4-fluoro-phenyl)-pyridin-4-yl]-4-methyl-piperazine

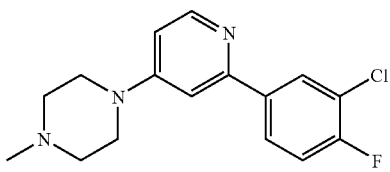

LC/MS: mass calcd. for C₁₆H₁₇ClFN₃, 305.1; m/z found, 306.2 [M+H]⁺

¹H NMR (CDCl₃); 8.34 (d, J=5.9, 1H), 7.99 (dd, J=7.2, 2.3, 1H), 7.79 (ddd, J=8.7, 4.7, 2.3, 1H), 7.20 (t, J=8.7, 1H), 7.00 (d, J=2.5, 1H), 6.65 (dd, J=5.9, 2.5, 1H), 3.41 (t, J=5.2, 4H), 2.56 (t, J=5.2, 4H), 2.36 (s, 3H).

EXAMPLE 31

1-[2-(3-Fluoro-4-methyl-Phenyl)-pyridin-4-yl]-4-methyl-piperazine

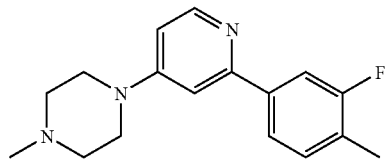

LC/MS: mass calcd. for C₁₇H₂₀FN₃, 285.2; m/z found, 286.2 [M+H]⁺

¹H NMR (CDCl₃): 8.33 (d, J=5.9, 1H), 7.61-7.58 (m, 2H), 7.23 (t, J=7.4, 1H), 7.01 (d, J=2.5, 1H), 6.64 (dd, J=6.0, 2.5, 1H), 3.42 (t, J=5.1, 4H), 2.56 (t, J=5.1, 4H), 2.36 (s, 3H), 2.31 (d, J=1.8, 3H).

EXAMPLE 32

1-Methyl-4-(2-p-tolyl-pyridin-4-yl)-piperazine

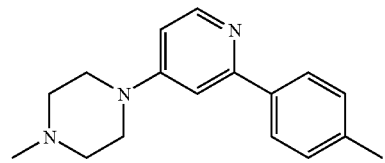

LC/MS: mass calcd. for C₁₇H₂₁N₃, 267.2; m/z found, 268.1 [M+H]⁺

¹H NMR (CDCl₃): 8.35 (d, J=5.9, 1H), 7.81 (d, J=8.2, 2H), 7.25 (d, J=8.2, 2H), 7.06 (d, J=2.5, 1H), 6.62 (dd, J=5.9, 2.5, 1H), 3.40 (t, J=5.2, 4H), 2.55 (t, J=5.2, 4H), 2.39 (s, 3H), 2.35 (s, 3H).

EXAMPLE 33

3-[4-(4-Methyl-piperazin-1-yl)-pyridin-2-yl]-phenol

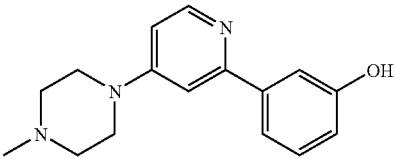

LC/MS: mass calcd. for C₁₆H₁₉N₃O, 269.2; m/z found, 270.1 [M+H]⁺.

¹H NMR (CDCl₃): 8.32 (d, J=6.0, 1H), 7.54 (dd, J=2.4, 1.7, 1H), 7.33-7.24 (m, 2H), 7.01 (d, J=2.4, 1H), 6.87-6.83 (m, 1H), 6.92 (dd, J=6.0, 2.4, 1H), 3.42 (t, J=5.2, 4H), 2.56 (t, J=5.2, 4H), 2.37 (s, 3H).

EXAMPLE 34

1-[2-(3,4-Difluoro-phenyl)-pyridin-4-yl]-4-methyl-piperazine

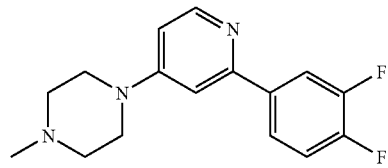

LC/MS: mass calcd. for C₁₆H₁₇F₂N₃, 289.1; m/z found, 290.1 [M+H]⁺.

¹H NMR (CDCl₃): 8.34 (d, J=5.9, 1H), 7.78 (m, 1H), 7.68-7.62 (m, 1H), 7.26-7.17 (m, 1H), 7.00 (d, J=2.5, 1H), 6.65 (dd, J=5.9, 2.5, 1H), 3.42 (t, J=5.2, 4H), 2.56 (t, J=5.2, 4H), 2.36 (s, 3H).

EXAMPLE 35

1-[2-(2,3-Dichloro-phenyl)-pyridin-4-yl]-4-methyl-piperazine

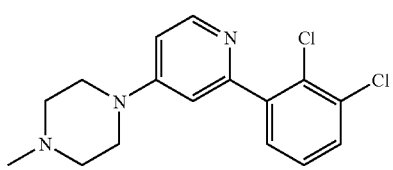

LC/MS: mass calcd. for C₁₆H₁₇Cl₂N₃, 321.1; m/z found, 322.1 [M+H]⁺.

¹H NMR (CDCl₃): 8.36 (d, J=6.0, 1H), 7.48 (dd, J=7.9, 1.7, 1H), 7.42 (dd, J=7.7, 1.7, 1H), 7.25 (t, J=7.8, 1H), 6.91 (d, J=2.6, 1H), 6.68 (dd, J=6.0, 2.6, 1H), 3.39 (t, J=5.2, 4H), 2.54 (t, J=5.2, 4H), 2.35 (s, 3H).

EXAMPLE 36

1-[2-(2,3-Dichloro-Phenyl)-pyridin-4-yl]-4-methyl-piperazine

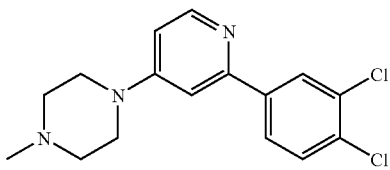

LC/MS: mass calcd. for $C_{16}H_{17}Cl_2N_3$, 321.1; m/z found, 322.1 [M+H]$^+$.

$^1$H NMR (CDCl$_3$): 8.34 (d, J=5.9, 1H), 8.03 (d, J=2.1, 1H), 7.76 (dd, J=8.4, 2.1, 1H), 7.49 (d, J=8.4, 1H), 7.02 (d, J=2.5, 1H), 6.65 (dd, J=5.9, 2.5, 1H), 3.41 (t, J=5.2, 4H), 2.55 (t, J=5.2, 4H), 2.36 (s, 3H).

EXAMPLE 37

1-[2-(3-Chloro-4-methyl-phenyl)-pyridin-4-yl]-4-methyl-piperazine

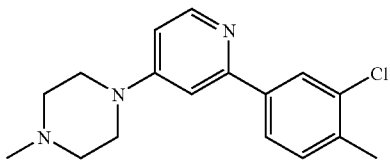

LC/MS: mass calcd. for $C_{17}H_{20}ClN_3$, 301.1; m/z found, 302.2 [M+H]$^+$.

$^1$H NMR (CDCl$_3$): 8.34 (d, J=5.9, 1H), 7.91 (d, J=2.1, 1H), 7.76 (dd, J=7.9, 1.9, 1H), 7.29 (d, J=7.9, 1H), 7.03 (d, J=2.5, 1H), 6.64 (dd, J=5.9, 2.5, 1H), 3.42 (t, J=5.2, 4H), 2.56 (t, J=5.2, 4H), 2.41 (s, 3H), 2.36 (s, 3H).

EXAMPLE 38

1-(2-Biphenyl-3-yl-pyridin-4-yl)-4-methyl-piperazine

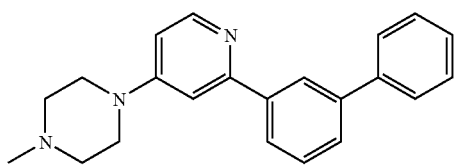

LC/MS: mass calcd. for $C_{22}H_{23}N_3$, 329.2; m/z found, 330.2 [M+H]$^+$.

$^1$H NMR (CDCl$_3$): 8.40 (d, J=5.9, 1H), 8.14 (t, J=1.5, 1H), 7.90 (dt, J=8.2, 1.5, 1H), 7.54-7.33 (m, 7H), 7.13 (d, J=2.5, 1H), 6.66 (dd, J=5.9, 2.5, 1H), 3.42 (t, J=5.2, 4H), 2.56 (t, J=5.2, 4H), 2.36 (s, 3H).

EXAMPLE 39

1-Methyl-4-(2-thiophen-3-yl-pyridin-4-yl)-[1,4]diazepane

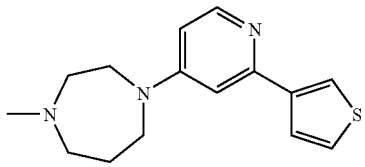

The title compound was prepared according to the methods as described in Example 26 with the following substitution: 1-methylhomopiperazine was used in place of 1-methylpiperazine.

LC/MS: mass calcd. for $C_{15}H_{19}N_3S$, 273.1; m/z found, 274.1 [M+H]$^+$.

$^1$H NMR (CDCl$_3$): 8.24 (d, J=6.0, 1H), 7.85 (dd, J=3.0, 1.2, 1H), 7.60 (dd, J=5.0, 1.2, 1H), 7.36 (dd, J=5.0, 3.0, 1H), 6.82 (d, J=2.6, 1H), 6.44 (dd, J=6.0, 2.6, 1H), 3.62 (t, J=5.1, 2H), 3.55 (t, J=6.3, 2H), 2.72 (t, J=4.8, 2H), 2.57 (t, J=5.5, 2H), 2.39 (s, 3H), 2.06-2.00 (m, 2H).

EXAMPLE 40

Methyl-(1-methyl-pyrrolidin-3-yl)-(2-thiophen-3-yl-pyridin-4-yl)-amine

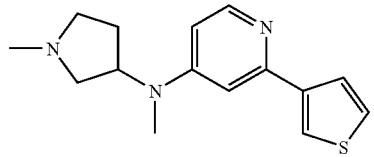

LC/MS: mass calcd. for $C_{15}H_{19}N_3S$, 273.1; m/z found, 274.1 [M+H]$^+$.

$^1$H NMR (CDCl$_3$): 8.24 (d, J=6.1, 1H), 7.87 (br m, 1H), 7.60 (dd, J=5.0, 1.2, 1H), 7.36 (dd, J=5.0, 3.0, 1H), 6.92 (d, J=2.6, 1H), 6.50 (dd, J=6.1, 2.6, 1H), 4.57 (m, 1H), 3.01 (s, 3H), 2.88-2.58 (m, 3H), 2.38 (s, 3H), 2.40-2.23 (m, 2H), 1.84 (m, 1H).

EXAMPLE 41

N,N,N'-Trimethyl-N'-(2-thiophen-3-yl-pyridin-4-yl)-ethane-1,2-diamine

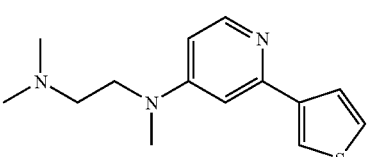

LC/MS: mass calcd. for $C_{14}H_{19}N_3S$, 261.1; m/z found, 262.1 [M+H]$^+$.

$^1$H NMR (CDCl$_3$): 8.24 (d, J=6.0, 1H), 7.82 (dd, J=3.0, 1.3, 1H), 7.58 (dd, J=5.0, 1.3, 1H), 7.34 (dd, J=5.0, 3.0, 1H), 6.82

(d, J=2.5, 1H), 6.42 (dd, J=6.0, 2.5, 1H), 3.49 (t, J=7.4, 2H), 3.02 (s, 3H), 2.48 (t, J=7.4, 2H), 2.29 (s, 3H).

EXAMPLE 42

Dimethyl-[1-(2-thiophen-3-yl-pyridin-4-yl)-pyrrolidin-3-yl]-amine

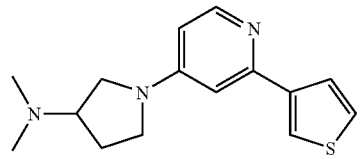

LC/MS: mass calcd. for $C_{15}H_{19}N_3S$, 273.1; m/z found, 274.1 [M+H]$^+$. $^1$H NMR (CDCl$_3$): 8.23 (d, J=5.9, 1H), 7.83 (dd, J=3.0, 1.3, 1H), 7.60 (dd, J=5.0, 1.3, 1H), 7.34 (dd, J=5.0, 3.0, 1H), 6.67 (d, J=2.4, 1H), 6.29 (dd, J=5.9, 2.5, 1H), 3.58-3.50 (m, 2H), 3.39-3.16 (m, 2H), 2.89-2.80 (m, 1H), 2.31 (s, 6H), 2.16-1.88 (m, 2H).

EXAMPLE 43

1-Methyl-4-(4-thiophen-2-yl-pyridin-2-yl)-piperazine

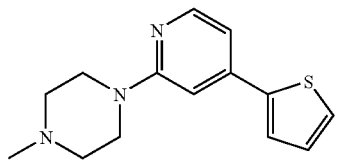

The title compound was prepared according to the methods as described in Example 26 with the following substitution: 4-bromo-2-chloropyridine was used in place of 2,4-dichloropyridine.

LC/MS: mass calcd. for $C_{14}H_{17}N_3S$, 259.1; m/z found, 260.1 [M+H]$^+$.

$^1$H NMR (CDCl$_3$): 8.16 (d, J=6.0, 1H), 7.43 (dd, J=3.0, 1.2, 1H), 7.36 (dd, J=5.0, 1.2, 1H), 7.10 (dd, J=5.0, 3.0, 1H), 6.86 (dd, J=6.0, 2.5, 1H), 6.82 (br s, 1H), 3.60 (t, J=5.2, 4H), 2.55 (t, J=5.2, 4H), 2.36 (s, 3H).

EXAMPLE 44

1-{2-[2-Chloro-5-(4-fluoro-phenyl)-thiophen-3-yl]-pyridin-4-yl}-4-methyl-piperazine

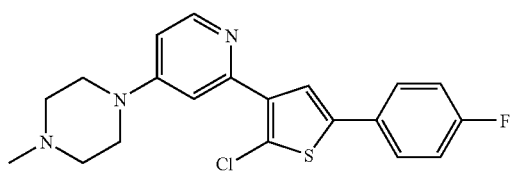

LC/MS: mass calcd. for $C_{20}H_{19}ClFN_3S$, 387.1; m/z found, 388.2 [M+H]$^+$.

$^1$H NMR (CDCl$_3$): 8.35 (d, J=5.9, 1H), 7.56 (s, 1H), 7.54 (dd, J=8.7, 5.2, 2H), 7.29 (d, J=2.6, 1H), 7.07 (t, J=8.6, 2H), 6.65 (dd, J=5.9, 2.6, 1H), 3.42 (t, J=5.2, 4H), 2.56 (t, J=5.2, 4H), 2.36 (s, 3H).

EXAMPLE 45

1-(2-Dibenzofuran-4-yl-pyridin-4-yl)-4-methyl-piperazine

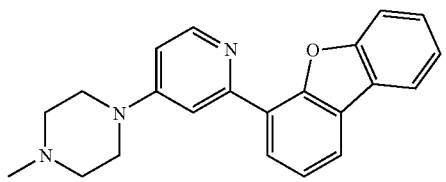

LC/MS: mass calcd. for $C_{22}H_{21}N_3O$, 343.2; m/z found, 344.2 [M+H]$^+$.

$^1$H NMR (CDCl$_3$): 8.47 (d, J=5.9, 1H), 8.20-7.97 (m, 3H), 7.77 (d, J=2.6, 1H), 7.63-7.34 (m, 4H), 6.71 (dd, J=5.9, 2.6, 1H), 3.50 (t, J=5.2, 4H), 2.61 (t, J=5.2, 4H), 2.39 (s, 3H).

EXAMPLE 46

1-Methyl-5-[4-(4-methyl-piperazin-1-yl)-pyridin-2-yl]-1H-indole

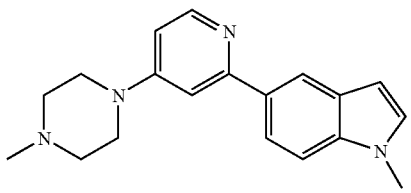

LC/MS: mass calcd. for $C_{19}H_{22}N_4$, 306.2; m/z found, 307.3 [M+H]$^+$.

$^1$H NMR (CDCl$_3$): 8.38 (d, J=6.0, 1H), 8.18 (t, J=1.7, 1H), 7.85 (dd, J=8.6, 1.7, 1H), 7.37 (d, J=8.6, 1H), 7.16 (d, J=2.6, 1H), 7.07 (d, J=3.1, 1H), 6.61 (dd, J=6.0, 2.6, 1H), 6.54 (dd, J=3.9, 1.1, 1H), 3.82 (s, 3H), 3.43 (t, J=5.2, 4H), 2.56 (t, J=5.2, 4H), 2.36 (s, 3H).

EXAMPLE 47

1-[2-(2-Chloro-thiophen-3-yl)-pyridin-4-yl]-4-methyl-piperazine

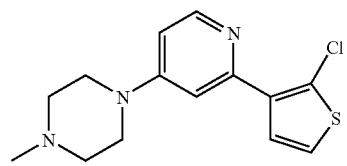

Step A: Preparation of 4-Chloro-2-(2-chloro-thiophen-3-yl)-pyridine

To a solution of 4-chloro-2-thiophen-3-yl-pyridine (410 mg, 2.1 mmol), prepared as described in Example 26, Step A, using 2-thiopheneboronic acid, in CH$_2$Cl$_2$ (10 mL), was added SO$_2$Cl$_2$ (1 M in CH$_2$Cl$_2$, 3 mL). The resulting mixture was stirred at room temperature for 8 h, then was poured into water and extracted with CH$_2$Cl$_2$. The organic layer was dried and concentrated to yield a residue. The residue was purified by preparative TLC (hexanes/EtOAc) to yield 2-(2-chloro-thiophen-3-yl)-4-chloro-pyridine.

$^1$H NMR (CDCl$_3$): 8.57 (dd, J=5.3, 0.6, 1H), 7.89 (dd, J=2.0, 0.6, 1H), 7.44 (d, J=5.8, 1H), 7.26 (dd, J=5.3, 2.0, 1H), 7.16 (d, J=5.7, 1H).

Step B: Preparation of the Title Compound.

The title compound was prepared from 4-chloro-2-(chloromethyl-thiophen-3-yl)-pyridine according to the methods described in Example 26, Step B.

LC/MS: mass calcd. for C$_{14}$H$_{16}$ClN$_3$S, 293.1; m/z found, 294.1 [M+H]$^+$.

$^1$H NMR (CDCl$_3$): 8.32 (d, J=6.0, 1H), 7.39 (d, J=5.8, 1H), 7.22 (d, J=2.6, 1H), 7.11 (d, J=5.8, 1H), 6.62 (dd, J=6.0, 2.6, 1H), 3.42 (dd, J=5.3, 5.0, 4H), 2.54 (dd, J=5.3, 5.0, 4H), 2.34 (s, 3H).

EXAMPLE 48

1-Methyl-4-[2-(2-methyl-thiophen-3-yl)-pyridin-4-yl]-piperazine

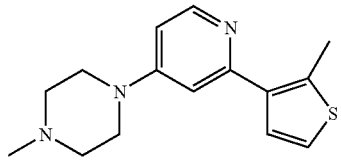

Step A: Preparation of 2-(2-bromo-thiophen-3-yl)-4-chloro-pyridine

A solution of 4-chloro-2-thiophen-3-yl-pyridine (755 mg, 3.9 mmol), prepared from 2-thiopheneboronic acid via the method outlined in Example 26, Step A, and N-bromosuccinimide (712 mg, 4 mmol) in DMF (6 mL) was stirred at room temperature for 8 h. The reaction mixture was poured into water and extracted with EtOAc. The organic layer was dried and concentrated to yield a residue. The residue was recrystallized from EtOH to yield 2-(2-bromo-thiophen-3-yl)-4-chloro-pyridine as a solid.

$^1$H NMR (CDCl$_3$): 8.58 (dd, J=5.3, 0.6, 1H), 7.88 (dd, J=2.0, 0.6, 1H), 7.38 (d, J=5.7, 1H), 7.33 (d, J=5.7, 1H), 7.26 (dd, J=5.3, 2.0, 1H).

Step B: Preparation of 4-Chloro-2-(2-methyl-thiophen-3-yl)-pyridine

To a solution of 2-(2-bromo-thiophen-3-yl)-4-chloro-pyridine (80 mg, 0.3 mmol) in Et$_2$O (3 mL) at −78° C. was added n-BuLi (1.6 M in hexanes, 0.2 mL). After 10 min, MeI (70 mg, 0.5 mmol) was added. The resulting mixture was maintained at −78° C. for 2 h, then was warmed to room temperature and stirred for 3 h. The reaction mixture was treated with 2 M aqueous NH$_4$Cl and extracted with EtOAc. The organic layer was dried and concentrated to yield a residue. The residue was purified by preparative TLC (hexanes/EtOAc) to yield 4-chloro-2-(2-methyl-thiophen-3-yl)-pyridine as a solid.

$^1$H NMR (CDCl$_3$): 8.55 (d, J=5.3, 1H), 7.47 (d, J=2.0, 1H), 7.29 (d, J=5.3, 1H), 7.20 (d, J=5.3, 1H), 7.15 (dd, J=5.3, 2.0, 1H), 2.69 (s, 3H).

Step C: Preparation of the Title Compound

The title compound was prepared from 4-chloro-2-(2-methyl-thiophen-3-yl)-pyridine according to the methods described in Example 26, Step B.

LC/MS: mass calcd. for C$_{15}$H$_{19}$N$_3$S, 273.1; m/z found, 274.2 [M+H]$^+$.

$^1$H NMR (CDCl$_3$): 8.34 (d, J=5.9, 1H), 7.25 (d, J=5.5, 1H), 7.07 (d, J=5.5, 1H), 6.84 (d, J=2.5, 1H), 6.60 (dd, J=5.9, 2.5, 1H), 3.38 (t, J=5.2, 4H), 2.63 (s, 3H), 2.54 (t, J=5.2, 4H), 2.35 (s, 3H).

EXAMPLE 49

1-[2-(4-Chloro-thiophen-2-yl)-pyridin-4-yl]-4-methyl-piperazine

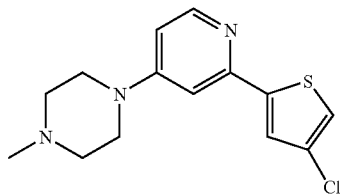

Step A: Preparation of 1-[2-(4-Chloro-5-trimethylsilanyl-thiophen-2-yl)-pyridin-4-yl]-4-methyl-piperazine 1-[2-(4-Chloro-5-trimethylsilanyl-thiophen-2-yl)-pyridin-4-yl]-4-methyl-piperazine was prepared according to the methods described in Example 26 using 4-chloro-5-trimethylsilyl-thiophene-2-boronic acid.

LC/MS: mass calcd. for C$_{17}$H$_{24}$ClN$_3$SSi, 365.1; m/z found, 366.2 [M+H]$^+$.

$^1$H NMR (CDCl$_3$): 8.24 (d, J=6.0, 1H), 7.42 (s, 1H), 6.98 (d, J=2.5, 1H), 6.69 (dd, J=6.0, 2.5, 1H), 3.41 (d, J=5.1, 4H), 2.57 (d, J=5.1, 4H), 2.37 (s, 3H), 0.40 (s, 9H).

Step B: Preparation of the Title Compound

A solution of 1-[2-(4-chloro-5-trimethylsilanyl-thiophen-2-yl)-pyridin-4-yl]-4-methyl-piperazine (20 mg, 0.05 mmol) in THF (1 mL) was treated with TBAF (1 M in THF, 0.2 mL). After 10 h, the resulting mixture was concentrated, diluted with water, and extracted with CH$_2$Cl$_2$. The organic layer was dried and concentrated, and the resulting residue was purified by preparative TLC (CH$_2$Cl$_2$/MeOH) to yield the title compound as a solid.

LC/MS: mass calcd. for $C_{14}H_{16}ClN_3S$, 293.1; m/z found, 294.0 [M+H]$^+$ $^1$H NMR (CDCl$_3$): 8.24 (d, J=6.0, 1H), 7.37 (d, J=1.5, 1H), 7.13 (d, J=1.5, 1H), 6.99 (d, J=2.5, 1H), 6.60 (dd, J=6.0, 2.5, 1H), 3.41 (d, J=5.1, 4H), 2.57 (d, J=5.1, 4H), 2.37 (s, 3H).

EXAMPLE 50

1-Methyl-4-(2-thiophen-2-yl-pyridin-4-yl)-piperazine

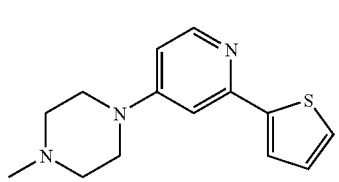

Step A: Preparation of
4-Chloro-2-thiophen-2-yl-pyridine

To a −78° C. suspension of 4-chloropyridine hydrochloride (1.8 g, 12 mmol) in anhydrous THF (15 mL) was slowly added thiophen-2-yl-magnesium bromide (25 mL, 25 mmol). After min, phenyl chloroformate (194 μL, 12 mmol) was slowly added via syringe. After another 15 min at −78° C., the resulting mixture was allowed to warm to room temperature. The reaction was quenched with 20% aqueous NH$_4$Cl (30 mL) and diluted with Et$_2$O (100 mL). The organic layer was separated and washed sequentially with water, 1 N HCl (30 mL), water (2×30 mL), and brine (30 mL). The organic layer was dried and concentrated to yield a dark brown oil (3.88 g), which was used in the next step, immediately.

To a solution of the dark brown oil in anhydrous toluene (30 mL) was added a solution of o-chloranil (3.25 g, 13.2 mmol) in glacial acetic acid (30 mL). After 24 h at room temperature, the mixture was cooled to 0° C., basified to pH>11 with 1 N NaOH, and stirred for 15 min. The resulting mixture was filtered through diatomaceous earth, washing with EtOAc. The organic layer of the filtrate was separated, washed with water (2×20 mL), dried, and concentrated to yield a residue. The residue was purified on SiO$_2$ (EtOAc/hexanes) to yield 4-chloro-2-thiophen-2-yl-pyridine as a pink crystalline solid.

$^1$H NMR (CDCl$_3$): 8.46 (d, J=5.4, 1H), 7.65 (d, J=1.9, 1H), 7.60 (dd, J=3.7, 1.1, 1H), 7.44 (dd, J=5.1, 1.1, 1H), 7.17-7.11 (m, 2H).

Step B: Preparation of the Title Compound

To a microwave tube was added 4-chloro-2-thiophen-2-yl-pyridine (98 mg, 0.5 mmol), 1-methylpiperazine (200 mg, 1 mmol), 2-propanol (1.0 mL) and concentrated HCl (1 drop). The resulting mixture was heated at 180° C. for 40 min using a Personal Chemistry Smith Synthesizer. The resulting mixture was poured into water and extracted with CH$_2$Cl$_2$. The organic layer was dried and concentrated to yield a reside. The residue was purified by preparative TLC (CH$_2$Cl$_2$/MeOH) to yield the title compound as a solid.

LC/MS: mass calcd. for $C_{14}H_{17}N_3S$, 259.1; m/z found, 260.1 [M+H]$^+$ $^1$H NMR (CDCl$_3$): 8.26 (d, J=6.0, 1H), 7.53 (dd, J=3.7, 1.1, 1H), 7.35 (dd, J=5.1, 1.1, 1H), 7.08 (dd, J=5.1, 3.7, 1H), 7.05 (d, J=2.5, 1H), 6.58 (dd, J=6.0, 2.5, 1H), 3.40 (t, J=5.2, 4H), 2.54 (t, J=5.2, 4H), 2.36 (s, 3H).

EXAMPLE 51

1-[2-(5-Chloro-thiophen-2-yl)-pyridin-4-yl]-4-methyl-piperazine

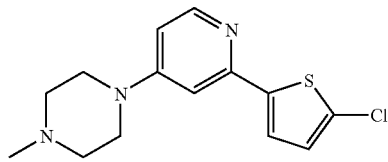

The title compound was prepared according to the methods described in Example 51, using 5-chlorothiophen-2-yl-magnesium bromide.

LC/MS: mass calcd. for $C_{14}H_{16}ClN_3S$, 293.1; found 294.2 [M+H]$^+$.

$^1$H NMR (CDCl$_3$); 8.20 (d, J=6.0, 1H), 7.27 (d, J=3.9, 1H), 6.94 (d, J=2.5, 1H), 6.89 (d, J=3.9, 1H), 6.56 (dd, J=6.0, 2.5, 1H), 3.38 (t, J=5.2, 4H), 2.54 (t, J=5.2, 4H), 2.35 (s, 3H).

EXAMPLE 52

1-[2-(5-Bromo-thiophen-2-yl)-pyridin-4-yl]-4-methyl-piperazine

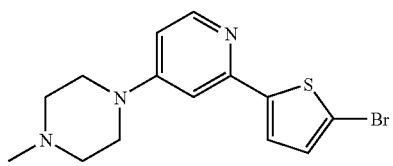

Step A: Preparation of
2-(5-Bromo-thiophen-2-yl)-4-chloro-pyridine

To a solution of 4-chloro-2-thiophen-2-yl-pyridine (195 mg, 0.55 mmol) in CH$_2$Cl$_2$ (2 mL) was added Br$_2$ (1 M in CH$_2$Cl$_2$, 0.6 mL). After 6 h, the resulting mixture was treated with Na$_2$S$_2$O$_3$ (1 M in water, 1 mL), stirred for 10 min, and extracted with CH$_2$Cl$_2$. The organic layer was dried and concentrated, and the resulting crude product was recrystallized from EtOH to yield 2-(5-bromo-thiophen-2-yl)-4-chloro-pyridine as a solid.

$^1$H NMR (CDCl$_3$): 8.41 (dd, J=5.4, 0.6, 1H), 7.56 (dd, J=1.9, 0.6, 1H), 7.30 (d, J=4.0, 1H), 7.15 (dd, J=5.4, 1.9, 1H), 7.07 (d, J=4.0, 1H).

Step B: Preparation of the Title Compound

The title compound was prepared from 2-(5-bromo-thiophen-2-yl)-4-chloro-pyridine according to the methods described in Example 26, Step B.

LC/MS: mass calcd. for $C_{14}H_{16}BrN_3S$, 337.0; m/z found, 338.1 $[M+H]^+$ $^1$H NMR (CDCl$_3$): 8.20 (d, J=6.0, 1H), 7.24 (d, J=3.9, 1H), 7.20 (d, J=3.9, 1H), 6.93 (d, J=2.5, 1H), 6.56 (dd, J=6.0, 2.5, 1H), 3.37 (t, J=5.2, 4H), 2.53 (t, J=5.2, 4H), 2.34 (s, 3H).

EXAMPLE 53

1-[2-(4'-Fluoro-biphenyl-3-yl)-pyridin-4-yl]-4-methyl-piperazine

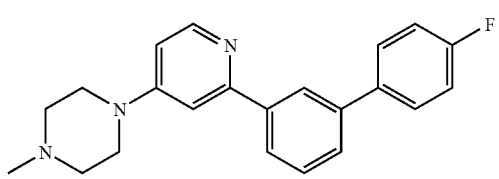

Step A: Preparation of Trifluoromethanesulfonic acid 3-[4-(4-methyl-piperazin-1-yl)-pyridin-2-yl]-phenyl ester A solution of 3-[4-(4-methyl-piperazin-1-yl)-pyridin-2-yl]-phenol (150 mg, 0.55 mmol) in CH$_2$Cl$_2$ (5 mL) was treated with pyridine (0.5 mL) and trifluoromethanesulfonic anhydride (170 mg, 0.6 mmol). After 5 h at room temperature, the resulting mixture was poured into water and extracted with CH$_2$Cl$_2$. The organic layer was dried and concentrated, and the resulting residue was purified by preparative TLC (MeOH/CH$_2$Cl$_2$) to yield trifluoro-methanesulfonic acid 3-[4-(4-methyl-piperazin-1-yl)-pyridin-2-yl]-phenyl ester as an oil.

LC/MS: mass calcd for $C_{17}H_{38}F_3N_3O_3S$, 401.1; found, 402.2 $[M+H]^+$ $^1$H NMR (CDCl$_3$): 8.37 (d, J=6.0, 1H), 7.95-7.92 (m, 1H), 7.86 (t, J=1.8, 1H), 7.54 (t, J=8.0, 1H), 7.31-7.27 (m, 1H), 7.05 (d, J=2.4, 1H), 6.69 (dd, J=6.0, 2.4, 1H), 3.42 (dd, J=5.3, 5.0, 4H), 2.56 (dd, J=5.3, 5.0, 4H), 2.37 (s, 3H).

Step B: Preparation of the Title Compound

To a N$_2$ flushed vial was sequentially added trifluoromethanesulfonic acid 3-[4-(4-methyl-piperazin-1-yl)-pyridin-2-yl]-phenyl ester (20 mg, 0.05 mmol), Pd(PPh$_3$)$_4$ (10 mg), and toluene/EtOH (4:1, 1 mL). After 5 min, 4-fluorophenylboronic acid (10 mg, 0.07 mmol) and 2 M aqueous K$_2$CO$_3$ (0.2 mL) were added. The resulting mixture was heated at 90° C. for 16 h, then was poured into water and extracted with CH$_2$Cl$_2$. The organic layer was dried and concentrated, and the resulting residue was purified by preparative TLC (MeOH/CH$_2$Cl$_2$) to yield the title compound as a solid.

LC/MS: mass calcd. for $C_{22}H_{22}FN_4$, 347.2; m/z found, 348.2 $[M+H]^+$ $^1$H NMR (CDCl$_3$): 8.39 (d, J=6.0, 1H), 8.10 (t, J=1.6, 1H), 7.87 (dt, J=7.8, 1.6, 1H), 7.63 (dd, J=8.9, 5.4, 2H), 7.56-7.48 (m, 2H), 7.16-7.10 (m, 3H), 6.69 (dd, J=6.0, 2.6, 1H), 3.43 (dd, J=5.3, 5.0, 4H), 2.56 (dd, J=5.3, 5.0, 4H), 2.37 (s, 3H).

Additional representative compounds of the present invention, as listed in Example 54-59, 101-103, 110 and 121 below, were prepared according to the methods described in Example 53, above substituting a suitably substituted boronic acid for the 4-fluorophenylboronic acid reagent. Additional substitutions and/or changes in reaction conditions, when present, were as described for each Example as noted.

EXAMPLE 54

1-[2-(4'-Methoxy-biphenyl-3-yl)-pyridin-4-yl]-4-methyl-piperazine

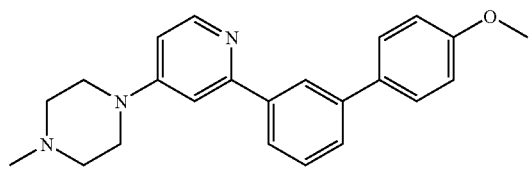

LC/MS: mass calcd. for $C_{23}H_{25}N_3O$, 359.2; m/z found, 360.3 $[M+H]^+$ $^1$H NMR (CDCl$_3$): 8.39 (d, J=6.0, 1H), 8.09 (t, J=1.6, 1H), 7.87 (dt, J=7.6, 1.6, 1H), 7.62-7.46 (m, 4H), 7.12 (d, J=2.5, 1H), 7.00 (d, J=8.9, 2H), 6.66 (dd, J=6.0, 2.5, 1H), 3.86 (s, 3H), 3.43 (t, J=5.2, 4H), 2.56 (t, J=5.2, 4H), 2.36 (s, 3H).

EXAMPLE 55

1-[2-(4'-Chloro-biphenyl-3-yl)-pyridin-4-yl]-4-methyl-piperazine

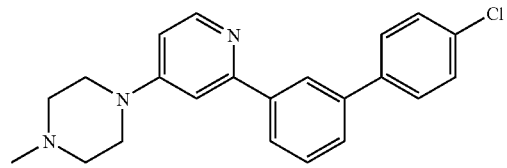

LC/MS: mass calcd. for $C_{22}H_{22}ClN_3$, 363.2; m/z found, 364.2 $[M+H]^+$.

$^1$H NMR (CDCl$_3$): 8.36 (d, J=6.0, 1H), 8.07 (br s, 1H), 7.87 (d, J=7.6, 1H), 7.60-7.39 (m, 6H), 7.08 (d, J=2.5, 1H), 6.67 (dd, J=6.0, 2.5, 1H), 3.45 (t, J=5.2, 4H), 2.57 (t, J=5.2, 4H), 2.37 (s, 3H).

EXAMPLE 56

3'-[4-(4-Methyl-piperazin-1-yl)-pyridin-2-yl]-biphenyl-4-carbonitrile

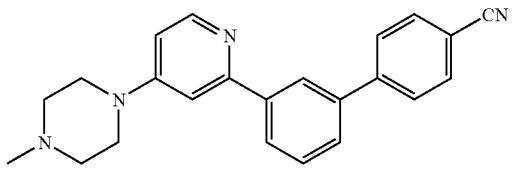

LC/MS: mass calcd. for $C_{23}H_{22}N_4$, 354.2; m/z found, 355.3 $[M+H]^+$.

$^1$H NMR (CDCl$_3$): 8.39 (d, J=5.9, 1H), 8.18 (t, J=1.5, 1H), 7.93 (dt, J=7.5, 1.5, 1H), 7.78-7.52 (m, 6H), 7.12 (d, J=2.5, 1H), 6.69 (dd, J=5.9, 2.5, 1H), 3.45 (t, J=5.2, 4H), 2.57 (t, J=5.2, 4H), 2.37 (s, 3H).

EXAMPLE 57

3'-[4-(4-Methyl-piperazin-1-yl)-pyridin-2-yl]-biphenyl-4-carboxylic acid amide

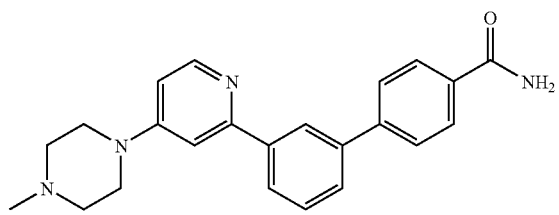

LC/MS: mass calcd. for $C_{23}H_{24}N_4O$, 372.2; m/z found, 373.3 $[M+H]^+$.

$^1$H NMR (CDCl$_3$): 8.39 (d, J=5.9, 1H), 8.17 (t, J=1.6, 1H), 7.93 (dt, J=7.5, 1.6, 1H), 7.79-7.52 (m, 6H), 7.11 (d, J=2.5, 1H), 6.69 (dd, J=5.9, 2.5, 1H), 3.44 (t, J=5.2, 4H), 2.57 (t, J=5.2, 4H), 2.37 (s, 3H).

EXAMPLE 58

3'-[4-(4-Methyl-piperazin-1-yl)-pyridin-2-yl]-biphenyl-4-carboxylic acid ethyl ester

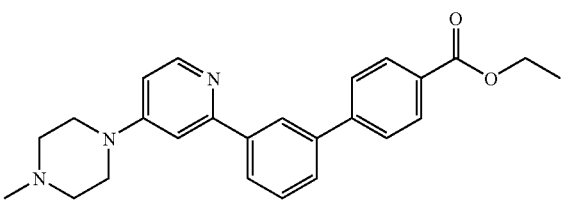

LC/MS: mass calcd. for $C_{25}H_{27}N_3O_2$, 401.2; m/z found, 402.4 $[M+H]^+$.

$^1$H NMR (CDCl$_3$): 8.39 (d, J=6.0, 1H), 8.17 (t, J=1.7, 1H), 8.12 (d, J=8.7, 2H), 7.93-7.51 (m, 5H), 7.12 (d, J=2.5, 1H), 6.68 (dd, J=6.0, 2.5, 1H), 4.40 (q, J=7.1, 2H), 3.43 (t, J=5.2, 4H), 2.56 (t, J=5.2, 4H), 2.36 (s, 3H), 1.41 (t, J=7.1, 3H).

EXAMPLE 59

Dimethyl-{3'-[4-(4-methyl-piperazin-1-yl)-pyridin-2-yl]-biphenyl-4-yl}-amine

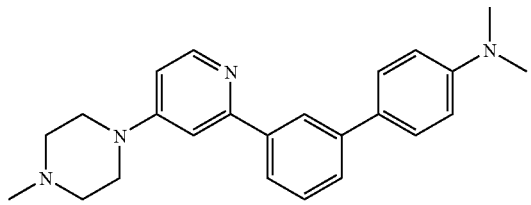

LC/MS: mass calcd. for $C_{24}H_{28}N_4$, 372.2; m/z found, 373.3 $[M+H]^+$.

$^1$H NMR (CDCl$_3$): 8.39 (d, J=6.0, 1H), 8.07 (t, J=1.8, 1H), 8.12 (d, J=8.7, 2H), 7.93-7.51 (m, 5H), 7.12 (d, J=2.5, 1H), 6.66 (dd, J=6.0, 2.5, 1H), 3.43 (t, J=5.2, 4H), 3.00 (s, 6H), 2.56 (t, J=5.2, 4H), 2.36 (s, 3H).

EXAMPLE 60

4-(4-Methyl-piperazin-1-yl)-2-thiophen-2-yl-pyrimidine

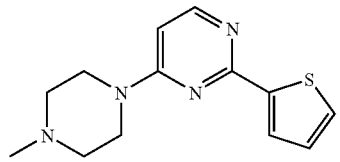

Step A: Preparation of 2-Chloro-4-(4-methyl-piperazin-1-yl)-pyrimidine

To a solution of 2,4-dichloropyrimidine (740 mg, 5 mmol) in EtOH (15 mL) was slowly added 1-methylpiperazine (550 mg, 5.5 mmol). The resulting mixture was stirred at room temperature overnight, then was concentrated, diluted with water, and extracted with CH$_2$Cl$_2$. The organic layer was dried and concentrated to yield 2-chloro-4-(4-methyl-piperazin-1-yl)-pyrimidine.

LC/MS: mass calcd. for $C_9H_{13}ClN_4$, 212.1; m/z found, 213.2 $[M+H]^+$ $^1$H NMR (CDCl$_3$): 8.03 (d, J=6.2, 1H), 6.38 (d, J=6.2, 1H), 3.67 (br s, 4H), 2.48 (t, J=5.2, 4H), 2.34 (s, 3H).

Step B: Preparation of the Title Compound

To a N$_2$ flushed vial was sequentially added 2-chloro-4-(4-methyl-piperazin-1-yl)-pyrimidine (63 mg, 0.3 mmol), Pd[P(t-Bu)$_3$]$_2$ (10 mg, 0.01 mmol), and dioxane (1 mL). After 5 min, 2-thiophenetributylstannane (125 mg, 0.33 mmol) and CsF (90 mg, 0.6 mmol) were added. The resulting mixture was heated at 95° C. for 20 h, then was poured into water and extracted with CH$_2$Cl$_2$. The organic layer was dried and concentrated, and the resulting residue was purified by preparative TLC (CH$_2$Cl$_2$/MeOH) to yield the title compound as a solid.

LC/MS: mass calcd. for $C_{13}H_{16}N_4S$, 260.1; m/z found, 261.1 [M+H]$^+$ $^1$H NMR (CDCl$_3$): 8.21 (d, J=6.2, 1H), 7.90 (dd, J=3.7, 1.2, 1H), 7.40 (dd, J=5.0, 1.2, 1H), 7.10 (dd, J=5.0, 3.7, 1H), 6.33 (d, J=6.2, 1H), 3.73 (t, J=5.0, 4H), 2.50 (t, J=5.0, 4H), 2.35 (s, 3H).

EXAMPLE 61

{3-[4-(4-Methyl-piperazin-1-yl)-pyridin-2-yl]-thiophen-2-yl}-methanol

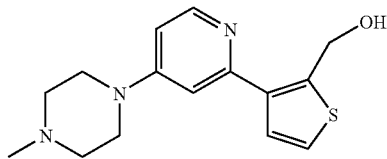

Step A: Preparation of 3-(4-Chloro-pyridin-2-yl)-thiophene-2-carbaldehyde 3-(4-Chloro-pyridin-2-yl)-thiophene-2-carbaldehyde was prepared according to the method as described in Example 26, Step A.

LC/MS: mass calcd. for $C_{10}H_6ClNOS$, 223.0; m/z found, 224.0 [M+H]$^+$ $^1$H NMR (CDCl$_3$): 10.5 (d, J=1.2, 1H), 8.61 (dd, J=5.3, 0.6, 1H), 7.74 (dd, J=5.1, 1.2, 1H), 7.64 (dd, J=1.9, 0.6, 1H), 7.43 (d, J=5.1, 1H), 7.34 (dd, J=5.3, 1.9, 1H).

Step B: Preparation of [3-(4-Chloro-pyridin-2-yl)-thiophen-2-yl]-methanol

To a solution of 3-(4-chloro-pyridin-2-yl)-thiophene-2-carbaldehyde (30 mg, 0.13 mmol) in EtOH (1 mL) was added NaBH$_4$ (50 mg, 1.3 mmol) at 0° C. The resulting mixture was stirred at room temperature overnight, then was poured into water and extracted with CH$_2$Cl$_2$. The organic layer was dried and concentrated to yield [3-(4-chloro-pyridin-2-yl)-thiophen-2-yl]-methanol as an oil.

$^1$H NMR (CDCl$_3$): 8.51 (d, J=6.0, 1H), 7.63 (d, J=2.0, 1H), 7.36 (d, J=5.3, 1H), 7.26-7.23 (m, 2H), 6.41 (br m, 1H), 4.71 (br m, 2H).

Step C: Preparation of the Title Compound

The title compound was prepared according to the methods described in Example 26, Step B.

LC/MS: mass calcd. for $C_{15}H_{19}N_3OS$, 289.1; m/z found, 290.2 [M+H]$^+$ $^1$H NMR (CDCl$_3$): 8.26 (d, J=6.0, 1H), 7.33 (d, J=5.2, 1H), 7.18 (d, J=5.2, 1H), 6.95 (d, J=2.6, 1H), 6.62 (dd, J=6.0, 2.6, 1H), 4.67 (s, 2H), 3.43 (t, J=5.2, 4H), 2.56 (t, J=5.2, 4H), 2.37 (s, 3H).

EXAMPLE 62

3'-[4-(4-Methyl-piperazin-1-yl)-pyridin-2-yl]-biphenyl-4-carboxylic acid

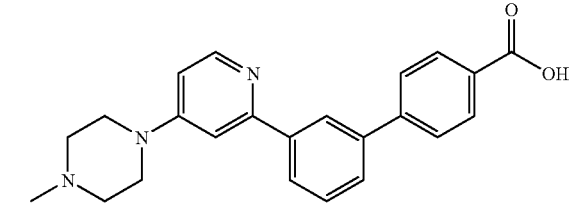

To a solution of 3'-[4-(4-methyl-piperazin-1-yl)-pyridin-2-yl]-biphenyl-4-carboxylic acid ethyl ester (182 mg, 0.4 mmol) in MeOH/water (3:1, 4 mL) was added LiOH (48 mg, 2 mmol). The resulting mixture was stirred at room temperature overnight. The resulting mixture was concentrated and the resulting aqueous solution was adjusted to pH 7 by the addition of 1 N HCl. The resulting mixture was concentrated and the resulting residue was dissolved in MeOH, dried, and concentrated to yield the title compound as a white solid.

LC/MS: mass calcd. for $C_{23}H_{23}N_3O_2$, 372.2; m/z found, 373.3 [M+H]$^+$ $^1$H NMR (CD$_3$OD): 8.24 (d, J=6.0, 1H), 8.11-7.53 (m, 8H), 7.26 (d, J=2.6, 1H), 6.86 (dd, J=6.0, 2.6, 1H), 3.52 (t, J=5.2, 4H), 2.60 (t, J=5.2, 4H), 2.36 (s, 3H).

EXAMPLE 63

{3'-[4-(4-Methyl-piperazin-1-yl)-pyridin-2-yl]-biphenyl-4-yl}-morpholin-4-yl-methanone

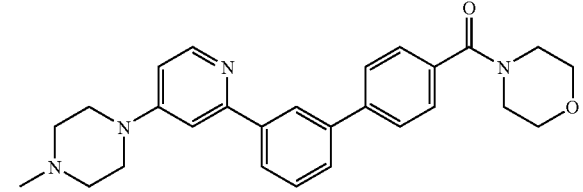

To a solution of 3'-[4-(4-methyl-piperazin-1-yl)-pyridin-2-yl]-biphenyl-4-carboxylic acid (30 mg, 0.08 mmol) in DMF (2 mL) was added morpholine (16 mg, 0.16 mmol), EDC (20 mg, 0.1 mmol), and Et$_3$N (10 mg, 0.1 mmol). The resulting mixture was stirred at room temperature overnight, and then was poured into water and extracted with CH$_2$Cl$_2$. The organic layer was washed with 1 N HCl, 2 M aqueous Na$_2$CO$_3$, dried, and concentrated, and the resulting residue was purified by preparative TLC (MeOH/CH$_2$Cl$_2$) to yield the title compound as a white solid.

LC/MS: mass calcd. for $C_{27}H_{30}N_4O_2$, 442.2; m/z found, 443.5 [M+H]$^+$ $^1$H NMR (CDCl$_3$): 8.41 (d, J=6.0, 1H), 8.14 (m, 1H), 7.89 (m, 1H), 7.74-7.48 (m, 6H), 7.12 (d, J=2.5, 1H), 6.68 (dd, J=6.0, 2.5, 1H), 3.86-3.60 (br m, 8H), 3.45 (t, J=5.2, 4H), 2.57 (t, J=5.2, 4H), 2.36 (s, 3H).

EXAMPLE 64

{3'-[4-(4-Methyl-piperazin-1-yl)-pyridin-2-yl]-biphenyl-4-yl}-pyrrolidin-1-yl-methanone

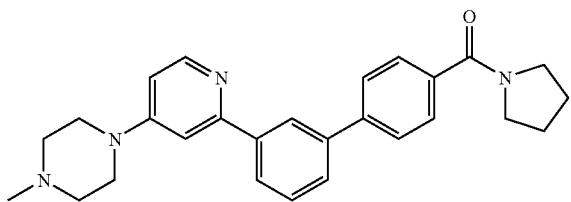

The title compound was prepared according to the methods described in Example 64.

LC/MS: mass calcd. for $C_{27}H_{30}N_4O$, 426.2; m/z found, 427.3 [M+H]$^+$.

$^1$H NMR (CDCl$_3$): 8.34 (d, J=6.0, 1H), 8.09 (br m, 1H), 7.87 (m, 1H), 7.66-7.45 (m, 6H), 7.04 (d, J=2.5, 1H), 6.64 (dd, J=6.0, 2.5, 1H), 3.62-3.49 (m, 8H), 2.52 (t, J=5.1, 4H), 2.31 (s, 3H), 193-1.82 (m, 4H).

EXAMPLE 65

Methyl-[1-(2-thiophen-3-yl-pyridin-4-yl)-pyrrolidin-3-yl]-amine

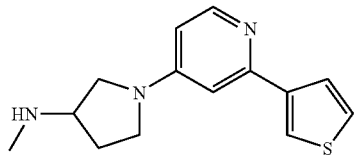

To a solution of 4-chloro-2-thiophen-3-yl-pyridine (50 mg, 0.4 mmol) in toluene (1 mL) was added Pd(OAc)$_2$ (2.3 mg, 0.01 mmol), 2-(di-t-butyl-phosphino)biphenyl (6.0 mg, 0.02 mmol), methyl-pyrrolidin-3-yl-carbamic acid tert-butyl ester (60 mg, 0.45 mmol), and NaOtBu (75 mg, 0.8 mmol). The resulting mixture was stirred at 90° C. for 16 h, then was cooled, poured into water, and extracted with EtOAc. The organic layer was dried and concentrated, and the resulting residue was purified by preparative TLC (hexanes/EtOAc) to yield methyl-[1-(2-thiophen-3-yl-pyridin-4-yl)-pyrrolidin-3-yl]-carbamic acid tert-butyl ester as a white solid (60 mg, 42%).

The white solid was dissolved in 50% TFA in CH$_2$Cl$_2$ (1 mL) and stirred at room temperature for 8 h. The resulting mixture was poured into water, neutralized with 2 M aqueous Na$_2$CO$_3$, and extracted with CH$_2$Cl$_2$. The organic layer was dried and concentrated to yield the title compound as an oil.

LC/MS: mass calcd. for $C_{14}H_{17}N_3S$, 259.1; m/z found, 260.0 [M+H]$^+$ $^1$H NMR (CDCl$_3$): 8.24 (d, J=5.9, 1H), 7.86 (dd, J=3.0, 1.2, 1H), 7.60 (dd, J=5.0, 1.2, 1H), 7.36 (dd, J=5.0, 3.0, 1H), 6.69 (d, J=2.4, 1H), 6.31 (dd, J=5.9, 2.4, 1H), 3.60-3.16 (m, 5H), 2.50 (s, 3H), 2.20 (m, 1H), 1.87 (m, 2H).

EXAMPLE 66

4-(4-Methyl-piperazin-1-yl)-6-thiophen-2-yl-pyrimidine

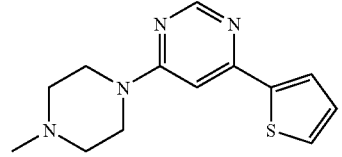

Step A: Preparation of 4-Chloro-6-thiophen-2-yl-pyrimidine

To a flask fitted with a condenser was added 4,6-dichloropyrimidine (500 mg, 3.36 mmol), thiophene-2-boronic acid (429 mg, 3.36 mmol), Pd(OAc)$_2$ (38 mg, 0.17 mmol), Ph$_3$P (88 mg, 0.34 mmol), 1 M Na$_2$CO$_3$ (10.4 mL, 10.4 mmol), and DME (20 mL). The resulting mixture was heated at 100° C. for 18 h. After cooling, the resulting mixture was partitioned between CHCl$_3$ (30 mL) and water (30 mL). The organic layer was dried and concentrated to yield a crude residue which was purified on SiO$_2$ (0-30% EtOAc/hexanes) to yield 4-chloro-6-thiophen-2-yl-pyrimidine.

$^1$H NMR (CDCl$_3$): 8.89 (d, J=1.0, 1H), 7.79 (dd, J=3.8, 1.0, 1H), 7.60-7.58 (m, 2H), 7.19 (d, J=5.1, 3.8, 1H).

Step B: Preparation of 4-(4-Methyl-piperazin-1-yl)-6-thiophen-2-yl-pyrimidine

To a solution of 4-chloro-6-thiophen-2-yl-pyrimidine (48 mg, 0.24 mmol) in ethanol (3 mL), was added 1-methylpiperazine (0.54 mL, 0.49 mmol). The resulting mixture was heated at 100° C. in a sealed tube for 2 h. The resulting mixture was concentrated and the resulting crude residue was purified by SiO$_2$ chromatography (0-5% 2 M NH$_3$ in MeOH/CH$_2$Cl$_2$) to yield the title compound.

MS: mass calcd. for $C_{13}H_{16}N_4S$, 260.11; m/z found, 261.3 [M+H]$^+$ $^1$H NMR (CD$_3$OD): 8.58 (d, J=1.0, 1H), 7.66 (dd, J=3.8, 1.0, 1H), 7.44 (dd, J=5.1, 1.0, 1H), 7.11 (dd, J=5.1, 3.8, 1H), 6.78 (d, J=1.0, 1H), 3.72-3.68 (m, 4H), 2.50-2.47 (m, 4H), 2.35 (s, 3H).

EXAMPLE 67

4-Piperazin-1-yl-6-thiophen-2-yl-pyrimidine

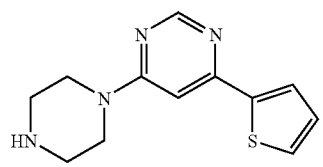

Step A: 4-(6-Thiophen-2-yl-pyrimidin-4-yl)-piperazine-1-carboxylic acid tert-butyl ester 4-(6-Thiophen-2-yl-pyrimidin-4-yl)-piperazine-1-carboxylic acid tert-butyl ester was prepared according to the methods described in Example 67, substituting piperazine-1-carboxylic acid tert-butyl ester for 1-methylpiperazine.

$^1$H NMR (CD$_3$OD): 8.60 (d, J=1.0, 1H), 7.68 (dd, J=3.8, 1.0, 1H), 7.45 (dd, J=5.1, 1.0, 1H), 7.13 (dd, J=5.1, 3.8, 1H), 6.78 (d, J=1.0, 1H), 3.72-3.69 (m, 4H), 3.57-3.55 (m, 4H), 1.50 (s, 9H).

Step B: Preparation of 4-Piperazin-1-yl-6-thiophen-2-yl-pyrimidine

A solution of 4-(6-thiophen-2-yl-pyrimidin-4-yl)-piperazine-1-carboxylic acid tert-butyl ester (30 mg, 0.08 mmol) in 1:1 TFA/CH$_2$Cl$_2$ (3 mL) was stirred for 2 h, and then was concentrated to yield the title compound, as its corresponding TFA salt.

MS: mass calcd. for C$_{13}$H$_{16}$N$_4$S, 246.33; m/z found, 247.5 [M+H]$^+$ $^1$H NMR (free base, CD$_3$OD): 8.58 (d, J=1.0, 1H), 7.66 (dd, J=3.8, 1.0, 1H), 7.44 (dd, J=5.1, 1.0, 1H), 7.11 (dd, J=5.1, 3.8, 1H), 6.78 (d, J=1.0, 1H), 3.71-3.68 (m, 4H), 2.48-2.46 (m, 4H).

EXAMPLE 68

1-Methyl-4-(6-thiophen-2-yl-pyrimidin-4-yl)-[1,4]diazepane

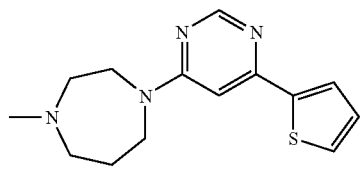

The title compound was prepared according to the methods described in Example 67.

MS: mass calcd. for C$_{14}$H$_{18}$N$_4$S, 274.13; m/z found, 275.3 [M+H]$^+$ $^1$H NMR (CD$_3$OD): 8.57 (d, J=1.0, 1H), 7.67 (dd, J=3.8, 1.0, 1H), 7.44 (dd, J=5.1, 1.0, 1H), 7.12 (dd, J=5.1, 3.8, 1H), 6.67 (d, J=1.0, 1H), 3.99-3.71 (m, 4H), 2.72-2.70 (m, 2H), 2.60-2.57 (m, 2H), 2.39 (s, 3H), 2.05-2.02 (m, 2H).

Additional representative compounds of the present invention, as listed in Example 69-151 below, were similarly prepared according to the methods described in the Examples detailed above, by selecting and substituting suitably substituted reagents.

EXAMPLE 69

2-piperazin-1-yl-4-thiophen-2-yl-pyrimidine

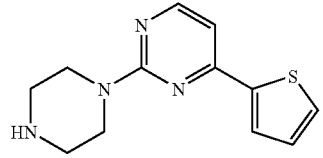

Step A: 2-Chloro-4-thiophen-2-yl-pyrimidine

To a vial was added 2,4-dichloropyridine (150 mg, 1 mmol), Pd(PPh$_3$)$_4$ (30 mg, 3%), and toluene/EtOH (4:1, 3 mL). After stirring at room temperature for 5 min, 2-thiopheneboronic acid (128 mg, 1 mmol) and 2 M aqueous K$_2$CO$_3$ (1 mL) were added, and the resulting mixture was heated at 90° C. for 16 h. The resulting mixture was poured into water and extracted with EtOAc. The organic layer was dried and concentrated, and the residue was purified by preparative TLC (hexanes/EtOAc) to yield 2-chloro-4-thiophen-2-yl-pyrimidine as a white solid.

$^1$H NMR (CDCl$_3$): 8.54 (d, 1H), 7.83 (dd, 1H), 7.60 (dd, 1H), 7.48 (d, 1H), 7.18 (dd, 1H),

Step B: Preparation of the Title Compound

To a microwave tube was added 2-chloro-4-thiophen-2-yl-pyrimidine (20 mg, 0.1 mmol), piperazine (26 mg, 0.3 mmol) and 2-propanol (0.6 mL). The resulting mixture was heated at 160° C. for 60 minutes using the microwave instrument. The resulting mixture was extracted with EtOAc. The organic layer was dried and concentrated, and the residue was purified by preparative TLC (hexanes/EtOAc) to yield the title compound as a solid.

LC/MS: mass calcd. for C$_{12}$H$_{14}$N$_4$S, 246.1; m/z found, 247.1 [M+H]$^+$.

$^1$H NMR (CDCl$_3$): 8.30 (d, 1H), 7.67 (dd, 1H), 7.45 (dd, 1H), 7.12 (dd, 1H), 6.81 (d, 1H), 3.90 (m, 4H), 2.95 (m, 4H).

EXAMPLE 70

4-(4-Methyl-piperazin-1-yl)-2-phenyl-pyrimidine

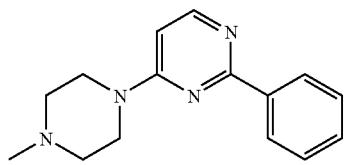

Step A: 2-Chloro-4-(4-methyl-piperazin-1-yl)-pyrimidine

To a solution of 2,4-dichloropyrimidine (447 mg, 3 mmol) in ethanol (10 mL) was added 1-methylpyperazine (360 mg, 3.6 mmol). The resulting mixture was stirred at room temperature overnight. The resulting white solid was collected by filtration and washed with ethanol, $Na_2CO_3$ solution and water and ethanol.

$^1$H NMR ($CDCl_3$): 8.06 (d, 1H), 6.40 (d, 1H), 3.70 (br, 4H), 2.50 (t, 4H), 2.37 (s, 3H).

Step B: Preparation of the Title Compound

To a microwave tube was added 2-chloro-4-(4-methyl-piperazin-1-yl)-pyrimidine (30 mg, 0.14 mmol), $Pd(PPh_3)_4$ (10 mg), phenylboronic acid (24 mg, 0.2 mmol), toluene/EtOH (4:1, 1 mL) and 2 M aqueous $K_2CO_3$ (0.2 mL). The resulting mixture was heated at 140° C. for 30 minutes using the microwave instrument. The resulting mixture was extracted with EtOAc. The organic layer was dried and concentrated, and the residue was purified by preparative TLC (hexanes/EtOAc) to yield the title compound as a solid.

LC/MS: mass calcd. for $C_{13}H_{18}N_4$, 254.2; m/z found, 255.1 $[M+H]^+$.

$^1$H NMR ($CDCl_3$): 8.42-8.30 (m, 3H), 7.50-7.38 (m, 3H), 6.42 (d, 1H), 3.80 (t, 4H), 2.50 (t, 4H), 2.35 (s, 3H).

EXAMPLE 71

2-(3-Chloro-4-fluoro-phenyl)-4-(4-methyl-piperazin-1-yl)-pyrimidine

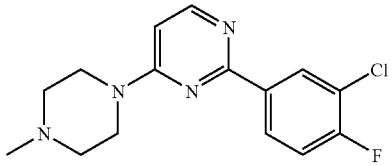

The title compound was prepared according to the methods described in Example 70.

LC/MS: mass calcd. for $C_{15}H_{16}ClFN_4$, 306.1; m/z found, 307.1 $[M+H]^+$.

$^1$H NMR ($CDCl_3$): 8.42 (d, 1H), 8.36-8.20 (m, 2H), 7.20 (t, 1H), 6.43 (d, 1H), 3.79 (t, 4H), 2.55 (t, 4H), 2.37 (s, 3H).

EXAMPLE 72

2-(3-Fluoro-phenyl)-4-(4-methyl-piperazin-1-yl)-pyrimidine

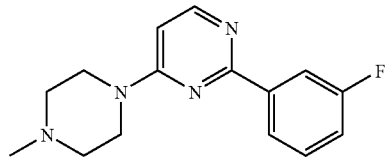

The title compound was prepared according to the methods described in Example 70.

LC/MS: mass calcd. for $C_{15}H_{17}FN_4$, 272.1; m/z found, 273.1 $[M+H]^+$.

$^1$H NMR ($CDCl_3$): 8.32 (d, 1H), 8.20 (d, 1H), 8.08 (d, 1H), 7.40 (m, 1H), 7.15 (t, 1H), 6.42 (d, 1H), 3.79 (t, 4H), 2.54 (t, 4H), 2.37 (s, 3H).

EXAMPLE 73

1-(4-Thiophen-2-yl-pyrimidin-2-yl)-[114]diazepane

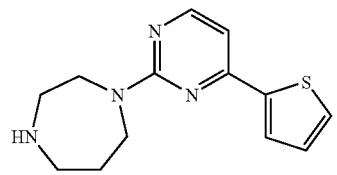

The title compound was prepared according to the methods described in Example 69.

LC/MS: mass calcd. for $C_{13}H_{16}N_4S$, 260.1; m/z found, 261.1 $[M+H]^+$.

$^1$H NMR ($CDCl_3$): 8.30 (d, 1H), 7.67 (dd, 1H), 7.45 (dd, 1H), 7.12 (dd, 1H), 6.81 (d, 1H), 4.00-3.80 (m, 4H), 3.20-2.80 (m, 5H), 2.00-1.80 (m, 2H).

EXAMPLE 74

1-Methyl-4-(6-thiophen-2-yl-pyridin-2-yl)-piperazine

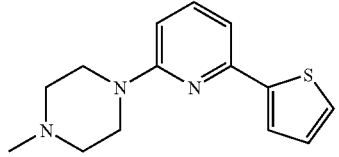

Step A:
1-(6-Chloro-pyridin-2-yl)-4-methyl-piperazine

To a vial was added 2,6-dichloropyridine (147 mg, 1 mmol), $Pd(OAc)_2$ (4.6 mg), 2-(di-t-butylphosphino)biphenyl (12 mg), sodium t-butoxide (192 mg, 2 mmol) 1-methylpiperazine (100 mg, 1 mmol) and toluene (3 mL). The resulting mixture was heated at 100° C. overnight and followed by extraction with EtOAc. The organic layer was dried and concentrated, and the residue was purified by preparative TLC (methanol/EtOAc) to yield a solid.

LC/MS: mass calcd. for $C_{10}H_{14}ClN_3$, 211.1; m/z found, 212.0 $[M+H]^+$ $^1$H NMR ($CDCl_3$): 7.39 (dd, 1H), 6.60 (d, 1H), 6.47 (d, 1H), 3.57 (t, 4H), 2.52 (t, 4H), 2.36 (s, 3H).

Step B: Preparation of the Title Compound

To a vial was added 1-(6-chloro-pyridin-2-yl)-4-methyl-piperazine (27 mg, 0.13 mmol), $Pd_2(dba)_3$ (14 mg), 2-(di-t-butylphosphino)biphenyl (18 mg), 2-thienyltributylstannane (51 mg, 0.15 mmol), dioxane (1 mL) and CsF (39 mg, 0.26 mmol). The resulting mixture was heated at 100° C. for 24 hrs. The resulting mixture was extracted with EtOAc. The organic layer was dried and concentrated, and the residue was purified by preparative TLC (hexanes/EtOAc) to yield the title compound as a solid.

LC/MS: mass calcd. for $C_{14}H_{17}N_3S$, 259.1; m/z found, 260.1 [M+H]$^+$ $^1$H NMR (CDCl$_3$): 7.53 (dd, 1H), 7.48 (dd, 1H), 7.32 (dd, 1H), 7.07 (dd, 1H), 7.00 (d, 1H), 6.52 (d, 1H), 3.64 (t, 4H), 2.55 (t, 4H), 2.36 (s, 3H).

EXAMPLE 75

1-Methyl-4-(5-thiophen-2-yl-pyridin-3-yl)-piperazine

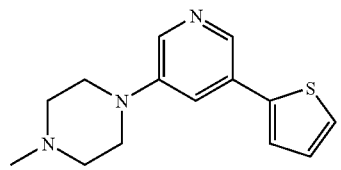

Step A:
1-(5-Bromo-pyridin-3-yl)-4-methyl-piperazine

To a vial was added 3,5-dibromopyridine (236 mg, 1 mmol), Pd(OAc)$_2$ (6.6 mg), 2-(di-t-butylphosphino)biphenyl (18 mg), sodium t-butoxide (192 mg, 2 mmol) 1-methylpiperazine (100 mg, 1 mmol) and toluene (3 mL). The resulting mixture was heated at 100° C. overnight and then extracted with EtOAc. The organic layer was dried and concentrated, and the residue was purified by preparative TLC (methanol/EtOAc) to yield a white solid.

LC/MS: mass calcd. for $C_{10}H_{14}BrN_3$, 255.0; m/z found, 256.0 [M+H]$^+$ $^1$H NMR (CDCl$_3$): 8.20 (d, 1H), 8.08 (d, 1H), 7.26 (d, 1H), 3.22 (t, 4H), 2.56 (t, 4H), 2.36 (s, 3H).

Step B: Preparation of the Title Compound

To a vial was added 1-(5-bromo-pyridin-3-yl)-4-methyl-piperazine (47 mg, 0.13 mmol), Pd(PPh$_3$)$_4$ (34 mg), 2-thienyltributylstannane (67 mg, 0.15 mmol) and dioxane (1 mL). The resulting mixture was heated at 100° C. for 24 hrs. The resulting mixture was extracted with EtOAc. The organic layer was dried and concentrated, and the residue was purified by preparative TLC (hexanes/EtOAc) to yield the title compound as a solid.

LC/MS: mass calcd. for $C_{14}H_{17}N_3S$, 259.1; m/z found, 260.1 [M+H]$^+$ $^1$H NMR (CDCl$_3$): 8.36 (d, 1H), 7.23 (d, 1H), 7.30-7.40 (m, 3H), 7.11 (dd, 1H), 3.32 (t, 4H), 2.61 (t, 4H), 2.39 (s, 3H).

EXAMPLE 76

4-Methyl-2-(4-methyl-piperazin-1-yl)-6-thiophen-2-yl-pyrimidine

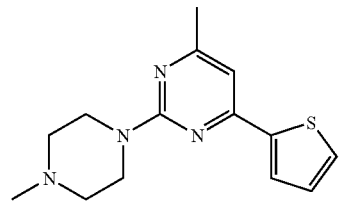

The title compound was prepared according to the methods described in Example 69.

LC/MS: mass calcd. for $C_{14}H_{18}N_4S$, 274.1; m/z found, 275.1 [M+H]$^+$ $^1$H NMR (CDCl$_3$): 7.65 (dd, 1H), 7.42 (dd, 1H), 7.10 (dd, 1H), 6.71 (s, 1H), 3.92 (t, 4H), 2.51 (t, 4H), 2.40 (s, 3H), 2.36 (s, 3H)

EXAMPLE 77

1-Methyl-4-[2-(3-trifluoromethyl-phenyl)-pyridin-4-yl]-piperazine

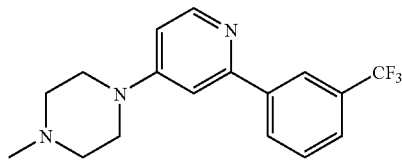

LC/MS: mass calcd. for $C_{17}H_{18}F_3N$, 321.2; m/z found, 322.1 [M+H]$^+$ $^1$H NMR (CDCl$_3$): 8.37 (d, 1H), 8.16 (s, 1H), 8.11 (d, 1H), 7.64 (d, 1H), 7.55 (t, 1H), 7.07 (d, 1H), 6.64 (dd, 1H), 3.42 (t, 4H), 2.57 (t, 4H), 2.36 (s, 3H).

EXAMPLE 78

-Methyl-4-(2-o-tolyl-pyridin-4-yl)-piperazine

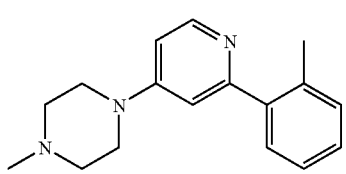

LC/MS: mass calcd. for $C_{17}H_{21}N_3$, 267.2; m/z found, 268.1 [M+H]$^+$ $^1$H NMR (CDCl$_3$): 8.37 (d, 1H), 7.35-7.20 (m, 4H), 6.74 (d, 1H), 6.64 (dd, 1H), 3.42 (t, 4H), 2.57 (t, 4H), 2.43 (s, 3H), 2.36 (s, 3H).

EXAMPLE 79

4-(4-Methyl-piperazin-1-yl)-[2,3']bipyridinyl

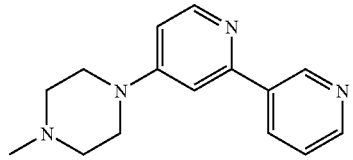

LC/MS: mass calcd. for $C_{15}H_{18}N_4$, 254.2; m/z found, 255.1 [M+H]$^+$ $^1$H NMR (CDCl$_3$): 9.08 (d, 1H), 8.60 (dd, 1H), 8.36 (d, 1H), 8.23 (m, 1H), 7.35 (m, 1H), 7.06 (d, 1H), 6.66 (dd, 1H), 3.42 (t, 4H), 2.57 (t, 4H), 2.35 (s, 3H).

EXAMPLE 80

1-[2-(3,5-Dimethyl-phenyl)-pyridin-4-yl]-4-methyl-piperazine

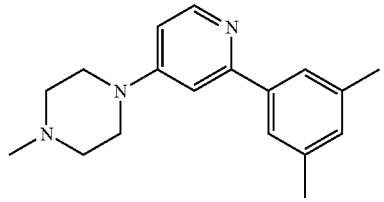

LC/MS: mass calcd. for $C_{18}H_{23}N_3$, 281.2; m/z found, 282.2 [M+H]$^+$ $^1$H NMR (CDCl$_3$): 8.36 (d, 1H), 7.52 (s, 2H), 7.06 (d, 1H), 7.03 (s, 1H), 6.64 (dd, 1H), 3.42 (t, 4H), 2.57 (t, 4H), 2.39 (s, 6H), 2.35 (s, 3H).

EXAMPLE 81

Dimethyl-{3-[4-(4-methyl-piperazin-1-yl)-pyridin-2-yl]-phenyl}-amine

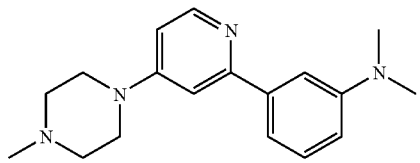

LC/MS: mass calcd. for $C_{18}H_{24}N_4$, 296.2; m/z found, 297.2 [M+H]$^+$ $^1$H NMR (CDCl$_3$): 8.37 (d, 1H), 7.36-7.14 (m, 3H), 7.07 (d, 1H), 6.79 (m, 1H), 6.64 (dd, 1H), 3.42 (t, 4H), 3.01 (s, 6H), 2.57 (t, 4H), 2.36 (s, 3H).

EXAMPLE 82

1-[2-(3-Methoxymethyl-phenyl)-pyridin-4-yl]-4-methyl-piperazine

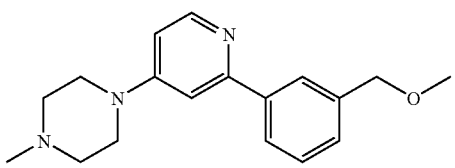

LC/MS: mass calcd. for $C_{18}H_{23}N_3O$, 297.2; m/z found, 298.1 [M+H]$^+$ $^1$H NMR (CDCl$_3$): 8.37 (d, 1H), 7.88 (s, 1H), 7.84 (d, 1H), 7.46-7.34 (m, 2H), 7.09 (d, 1H), 6.64 (dd, 1H), 4.54 (s, 2H), 3.42 (t, 4H), 3.39 (s, 3H), 2.57 (t, 4H), 2.36 (s, 3H).

EXAMPLE 83

2-[4-(4-Methyl-piperazin-1-yl)-pyridin-2-yl]-phenol

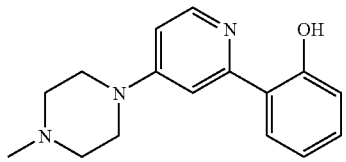

LC/MS: mass calcd. for $C_{16}H_{19}N_3O$, 269.2; m/z found, 270.2 [M+H]$^+$ $^1$H NMR (CDCl$_3$): 8.17 (d, 1H), 7.73 (dd, 1H), 7.27 (td, 1H), 7.21 (d, 1H), 7.00 (dd, 1H), 6.86 (td, 1H), 6.64 (dd, 1H), 3.45 (t, 4H), 2.57 (t, 4H), 2.36 (s, 3H).

EXAMPLE 84

1-Methyl-4-[2-(4-methyl-thiophen-2-yl)-pyridin-4-yl]-piperazine

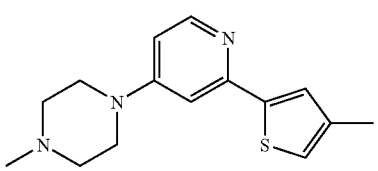

LC/MS: mass calcd. for $C_{15}H_{19}N_3S$, 273.1; m/z found, 274.1 $[M+H]^+$ $^1$H NMR (CDCl$_3$): 8.24 (d, 1H), 7.35 (d, 1H), 7.00 (d, 1H), 6.92 (d, 1H), 6.62 (dd, 1H), 3.42 (t, 4H), 2.57 (t, 4H), 2.50 (s, 3H), 2.36 (s, 3H).

EXAMPLE 85

1-(2-Benzofuran-2-yl-pyridin-4-yl)-4-methyl-piperazine

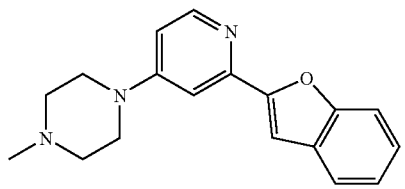

LC/MS: mass calcd. for $C_{18}H_{19}N_3O$, 293.2; m/z found, 294.2 $[M+H]^+$ $^1$H NMR (CDCl$_3$): 8.34 (d, 1H), 7.64 (dd, 1H), 7.54 (dd, 1H), 7.40-7.20 (m, 4H), 6.62 (dd, 1H), 3.42 (t, 4H), 2.57 (t, 4H), 2.36 (s, 3H).

EXAMPLE 86

1-(2-Benzo[b]thiophen-3-yl-pyridin-4-yl)-4-methyl-piperazine

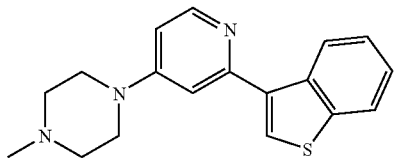

LC/MS: mass calcd. for $C_{18}H_{19}N_3S$, 309.1; m/z found, 310.0 $[M+H]^+$ $^1$H NMR (CDCl$_3$): 8.42 (d, 1H), 8.32 (dd, 1H), 7.90 (dd, 1H), 7.40 (m, 2H), 7.05 (d, 1H), 6.69 (dd, 1H), 3.43 (t, 4H), 2.58 (t, 4H), 2.37 (s, 3H).

EXAMPLE 87

1-[2-(3-Chloro-phenyl)-pyridin-4-yl]-4-methyl-piperazine

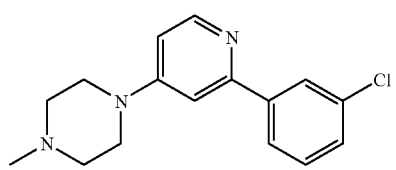

LC/MS: mass calcd. for $C_{16}H_{18}ClN_3$, 287.1; m/z found, 288.1 $[M+H]^+$ $^1$H NMR (CDCl$_3$): 8.36 (d, 1H), 7.91 (m, 1H), 7.82-7.80 (m, 1H), 7.38-7.34 (m, 2H), 7.04 (d, 1H), 6.65 (dd, 1H), 3.42 (t, 4H), 2.57 (t, 4H), 2.36 (s, 3H).

EXAMPLE 88

1-Methyl-4-(2-naphthalen-1-yl-Pyridin-4-yl)-piperazine

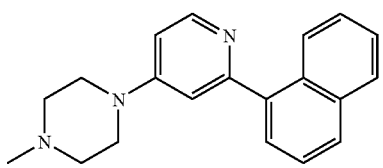

LC/MS: mass calcd. for $C_{20}H_{21}N_3$, 303.2; m/z found, 304.2 $[M+H]^+$ $^1$H NMR (CDCl$_3$): 8.41 (d, 1H), 8.13 (m, 1H), 7.88 (m, 2H), 7.68-7.42 (m, 4H), 6.92 (d, 1H) 6.72 (dd, 1H), 3.42 (t, 4H), 2.57 (t, 4H), 2.36 (s, 3H).

EXAMPLE 89

1-Methyl-4-(2-naphthalen-2-yl-pyridin-4-yl)-piperazine

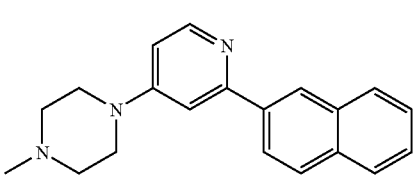

LC/MS: mass calcd. for $C_{20}H_{21}N_3$, 303.2; m/z found, 304.2 $[M+H]^+$ $^1$H NMR (CDCl$_3$): 8.42 (m, 2H), 8.30 (dd, 1H), 7.94-7.82 (m, 3H), 7.52-7.44 (m, 2H), 7.21 (d, 1H) 6.51 (dd, 1H), 3.42 (t, 4H), 2.57 (t, 4H), 2.36 (s, 3H).

EXAMPLE 90

1-Methyl-4-(2-m-tolyl-pyridin-4-yl)-piperazine

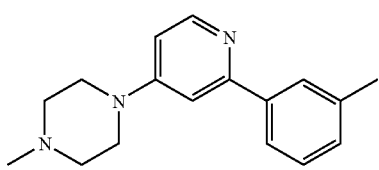

LC/MS: mass calcd. for $C_{17}H_{21}N_3$, 267.2; m/z found, 268.2 $[M+H]^+$ $^1$H NMR (CDCl$_3$): 8.37 (d, 1H), 7.76 (s, 1H), 7.68 (d, 1H), 7.33 (t, 1H), 7.20 (d, 1H), 7.08 (d, 1H), 6.64 (dd, 1H), 3.42 (t, 4H), 2.57 (t, 4H), 2.43 (s, 3H), 2.36 (s, 3H).

EXAMPLE 91

1-(2-Biphenyl-4-yl-pyridin-4-yl)-4-methyl-piperazine

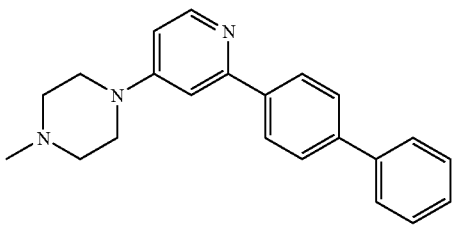

LC/MS: mass calcd. for $C_{22}H_{23}N_3$, 329.2; m/z found, 330.2 $[M+H]^+$ $^1$H NMR (CDCl$_3$): 8.40 (d, 1H), 8.01 (d, 2H), 7.72-7.64 (m, 4H), 7.46 (t, 2H), 7.36 (t, 1H), 7.14 (d, 1H), 6.66 (dd, 1H), 3.43 (t, 4H), 2.57 (t, 4H), 2.37 (s, 3H).

EXAMPLE 92

-[4-(4-Methyl-piperazin-1-yl)-pyridin-2-yl]-phenylamine

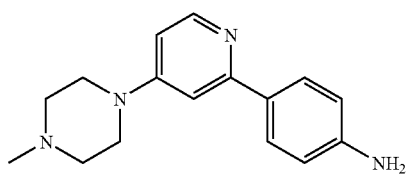

LC/MS: mass calcd. for $C_{16}H_{20}N_4$, 268.2; m/z found, 269.2 $[M+H]^+$.

$^1$H NMR (CDCl$_3$): 8.33 (d, 1H), 7.77 (d, 2H), 7.00 (d, 1H), 6.75 (d, 1H), 6.58 (dd, 1H), 3.80 (s, 2H), 3.41 (t, 4H), 2.55 (t, 4H), 2.35 (s, 3H).

EXAMPLE 93

1-Methyl-4-(2-methyl-6-thiophen-2-yl-pyridin-4-yl)-piperazine

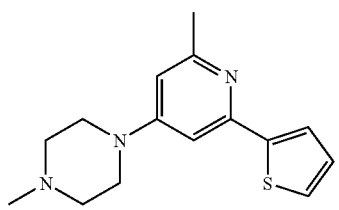

LC/MS: mass calcd. for $C_{15}H_{19}N_3S$, 273.1; m/z found, 274.2 $[M+H]^+$.

$^1$H NMR (CDCl$_3$): 7.57 (d, 1H), 7.33 (d, 1H), 7.07 (dd, 1H), 6.89 (d, 1H), 6.46 (d, 1H), 3.41-3.38 (m, 4H), 2.57-2.54 (m, 4H), 2.49 (s, 3H), 2.36 (s, 3H).

EXAMPLE 94

1-[4-(3-Fluoro-4-methyl-phenyl)-pyridin-2-yl]-4-methyl-piperazine

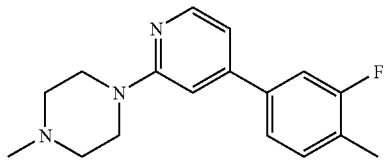

Step A:
2-Chloro-4-(3-fluoro-4-methyl-phenyl)-pyridine

To a vial was added 2-chloro-4-bromopyridine (96 mg, 0.5 mmol), Pd(PPh$_3$)$_4$ (30 mg), and toluene/EtOH (4:1, 3 mL). After stirring at room temperature for 5 min, 3-fluoro-4-methylphenylboronic acid (115 mg, 0.75 mmol) and 2 M aqueous K$_2$CO$_3$ (1 mL) were added, and the resulting mixture was heated at 90° C. for 16 h. The resulting mixture was poured into water and extracted with EtOAc. The organic layer was dried and concentrated, and the residue was purified by preparative TLC (hexanes/EtOAc) to yield 2-chloro-4-(3-fluoro-4-methyl-phenyl)-pyridine as a solid.

$^1$H NMR (CDCl$_3$): 7.58-7.26 (m, 5H), 2.36 (s, 3H).

Step B: Preparation of the Title Compound

To a microwave tube was added 2-chloro-4-(3-fluoro-4methyl-phenyl)-pyridine (30 mg, 0.14 mmol), 1-methylpiperazine (50 mg, 0.5 mmol), 2-propanol (0.6 mL) and 1 drop concentrated HCl. The resulting mixture was heated at 180° C. for 60 minutes using the microwave instrument. The resulting mixture was extracted with EtOAc. The organic layer was dried and concentrated, and the residue was purified by preparative TLC (hexanes/EtOAc) to yield the title compound as a solid.

LC/MS: mass calcd. for $C_{17}H_{20}FN_3$, 285.2; m/z found, 286.2 $[M+H]^+$ $^1$H NMR (CDCl$_3$): 8.34 (d, 1H), 7.62 (s, 1H), 7.58 (m, 1H), 7.22 (d, 1H), 7.04 (d, 1H), 6.64 (dd, 1H), 3.42 (t, 4H), 2.57 (t, 4H), 2.36 (s, 3H), 2.30 (s, 3H).

EXAMPLE 95

1-(4-Biphenyl-3-yl-pyridin-2-yl)-4-methyl-piperazine

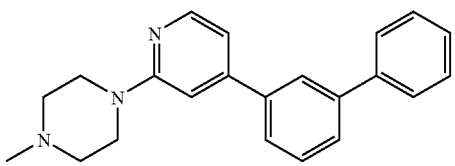

The title compound was prepared according to the methods described in Example 94.

LC/MS: mass calcd. for $C_{22}H_{23}N_3$, 329.2; m/z found, 330.2 [M+H]$^+$ $^1$H NMR (CDCl$_3$): 8.40 (d, 1H), 7.90 (t, 1H), 7.70-7.32 (m, 7H), 7.12 (d, 1H) 6.67 (dd, 1H), 3.44 (t, 4H), 2.57 (t, 4H), 2.36 (s, 3H).

EXAMPLE 96

2-(3-Fluoro-4-methyl-phenyl)-4-(4-methyl-piperazin-1-yl)-pyrimidine

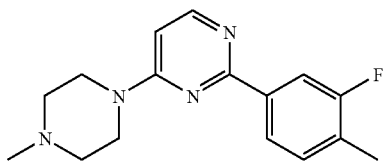

The title compound was prepared according to the methods described in Example 70.

LC/MS: mass calcd. for $C_{16}H_{19}FN_4$, 286.2; m/z found, 287.2[M+H]$^+$.

$^1$H NMR (CDCl$_3$): 8.30 (d, 1H), 8.12-8.00 (m, 2H), 7.24 (t, 1H), 6.42 (d, 1H), 3.76 (t, 4H), 2.54 (t, 4H), 2.38 (s, 3H), 2.34 (s, 3H).

EXAMPLE 97

2-Biphenyl-3-yl-4-(4-methyl-piperazin-1-yl)-pyrimidine

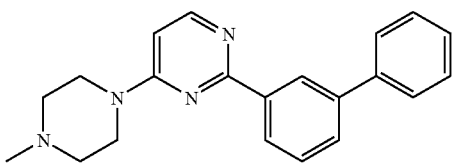

The title compound was prepared according to the methods described in Example 70.

LC/MS: mass calcd. for $C_{21}H_{22}N_4$, 330.2; m/z found, 331.2[M+H]$^+$.

$^1$H NMR (CDCl$_3$): 8.63 (t, 1H), 8.40-8.26 (m, 2H), 7.80-7.30 (m, 7H), 6.44 (d, 1H), 3.79 (t, 4H), 2.54 (t, 4H), 2.38 (s, 3H).

EXAMPLE 98

4-(4-Methyl-piperazin-1-yl)-2-thiophen-3-yl-pyrimidine

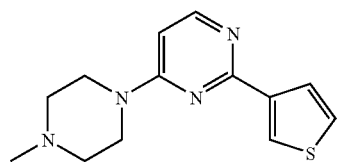

The title compound was prepared according to the methods described in Example 70.

LC/MS: mass calcd. for $C_{13}H_{16}N_4S$, 260.1; m/z found, 261.1 [M+H]$^+$.

$^1$H NMR (CDCl$_3$): 8.26 (d, 1H), 8.18 (dd, 1H), 7.82 (dd, 1H), 7.33 (dd, 1H), 6.37 (d, 1H), 3.74 (t, 4H), 2.53 (t, 4H), 2.36 (s, 3H).

EXAMPLE 99

1-Methyl-4-(4-thiophen-3-yl-pyridin-2-yl)-piperazine

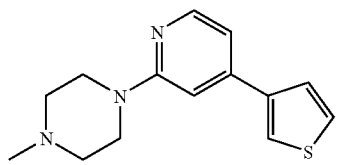

The title compound was prepared according to the methods described in Example 94.

LC/MS: no exact mass was detected.

$^1$H NMR (CDCl$_3$): 8.30 (d, 1H), 7.83 (dd, 1H), 7.60 (dd, 1H), 7.36 (dd, 1H), 7.00 (d, 1H), 6.60 (dd, 1H), 3.41 (t, 4H), 2.57 (t, 4H), 2.37 (s, 3H).

EXAMPLE 100

1-Methyl-4-[2-(5-phenyl-thiophen-2-yl)-pyridin-4-yl]-piperazine

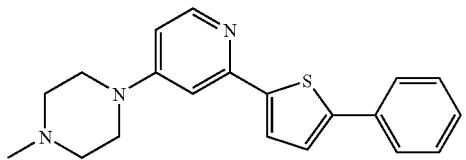

The title compound was prepared by treating 1-[2-(5-bromo-thiophen-2-yl)-pyridin-4-yl]-4-methyl-piperazine with phenylboronic acid under conditions as described in Example 26.

LC/MS: mass calcd. for $C_{20}H_{21}N_3S$, 335.2; m/z found, 336.2 [M+H]$^+$ $^1$H NMR (CDCl$_3$): 8.27 (d, 1H), 7.68-7.27 (m, 7H), 7.06 (d, 1H), 6.58 (dd, 1H), 3.42 (t, 4H), 2.57 (t, 4H), 2.38 (s, 3H).

EXAMPLE 101

1-Methyl-4-[2-(4'-methyl-biphenyl-3-yl)-pyridin-4-yl]-piperazine hydrochloride salt

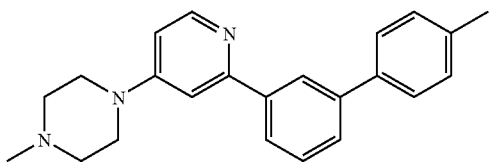

LC/MS: mass calcd. for $C_{23}H_{25}N_3$, 343.2; m/z found, 344.3 [M+H]$^+$ $^1$H NMR (DMSO): 14.3 (m, 0.4H), 11.5 (m, 0.6H), 8.41 (d, 1H), 8.10 (t, 1H), 7.94 (d, 2H), 7.78-7.60 (m, 4H), 7.38-7.26 (m, 3H), 44.60 (m, 2H), 3.80-3.40 (m, 4H), 3.21 (m, 2H), 2.81 (s, 3H), 2.39 (s, 3H).

EXAMPLE 102

1-[2-(3'-Chloro-4'-fluoro-biphenyl-3-yl)-pyridin-4-yl]-4-methyl-piperazine

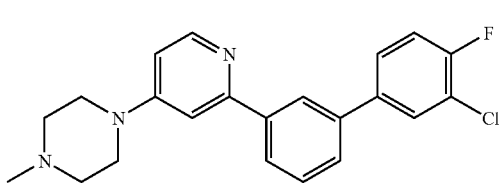

LC/MS: mass calcd. for $C_{22}H_{21}ClFN_3$, 381.2; m/z found, 382.2 [M+H]$^+$ $^1$H NMR (CDCl$_3$): 8.40 (d, 1H), 8.07 (t, 1H), 7.88 (dt, 1H), 7.70 (dd, 1H), 7.54-7.47 (m, 3H), 7.21 (t, 1H), 7.11 (d, 1H), 6.68 (dd, 1H), 3.43 (t, 4H), 2.57 (t, 4H), 2.37 (s, 3H).

EXAMPLE 103

1-[2-(2',3'-Dichloro-biphenyl-3-yl)-pyridin-4-yl]-4-methyl-piperazine, hydrochloride salt

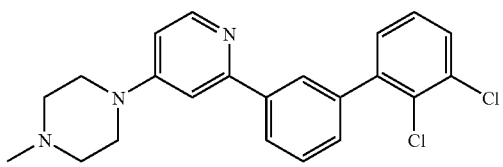

LC/MS: mass calcd. for $C_{22}H_{21}Cl_2N_3$, 397.1; m/z found, 398.2 [M+H]$^+$ $^1$H NMR (DMSO): 14.4 (m, 0.4H), 11.6 (m, 0.6H), 8.40 (d, 1H), 8.10 (m, 2H), 7.80-7.30 (m, 7H), 4.60 (m, 2H), 3.80-3.40 (m, 4H), 3.21 (m, 2H), 2.81 (s, 3H).

EXAMPLE 104

2-Biphenyl-3-yl-4-(4-methyl-piperazin-1-yl)-[1,3,5]triazine

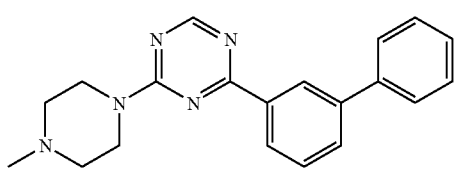

LC/MS: mass calcd. for $C_{20}H_{21}N_5$, 331.2; m/z found, 332.2 [M+H]$^+$ $^1$H NMR (CDCl$_3$): 8.67 (s, 1H), 8.64 (t, 1H), 8.39 (d, 1H), 7.76 (d, 2H), 7.68 (d, 2H), 7.55 (t, 1H), 7.47 (t, 2H), 7.38 (t, 1H), 4.08 (br s, 2H), 3.98 (br s, 2H), 2.53 (br s, 4H), 2.38 (s, 3H).

EXAMPLE 105

1-[2-(2,5-Dichloro-thiophen-3-yl)-pyridin-4-yl]-4-methyl-piperazine

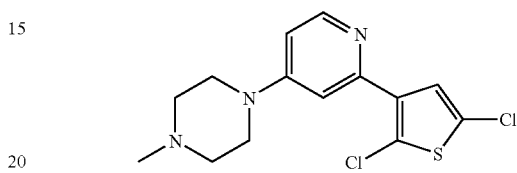

The title compound was prepared according to the methods described in Example 47.

LC/MS: mass calcd. for $C_{14}H_{15}Cl_2N_3S$, 327.0; m/z found, 328.1 [M+H]$^+$.

$^1$H NMR (CDCl$_3$): 8.30 (d, 1H), 7.26 (s, 1H), 7.18 (d, 1H), 6.62 (dd, 1H), 3.41-3.37 (m, 4H), 2.56-2.53 (m, 4H), 2.35 (s, 3H).

EXAMPLE 106

1-[2-(5-Bromo-2-chloro-thiophen-3-yl)-pyridin-4-yl]-4-methyl-piperazine

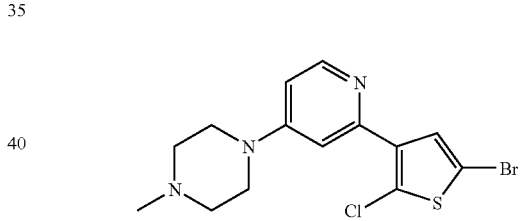

The title compound was prepared according to the methods described in Example 52, substituting 4-chloro-2-(2-chloro-thiophen-3-yl)-pyridine as appropriate.

LC/MS: mass calcd. for $C_{14}H_{15}BrClN_3S$, 371.0; m/z found, 372.1 [M+H]$^+$ $^1$H NMR (CDCl$_3$): 8.31 (d, 1H), 7.41 (s, 1H), 7.18 (d, 1H), 6.62 (dd, 1H), 3.40 (t, 4H), 2.57 (t, 4H), 2.36 (s, 3H).

EXAMPLE 107

3-[4-(4-Methyl-piperazin-1-yl)-[1,3,5]triazin-2-yl]-benzonitrile

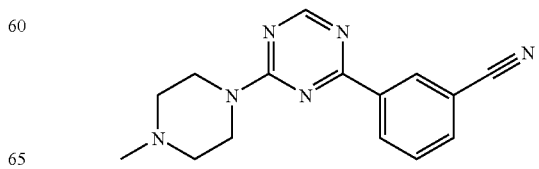

LC/MS: mass calcd. for $C_{15}H_{16}N_6$, 280.1; m/z found, 281.2 $[M+H]^+$ $^1$H NMR (CDCl$_3$): 8.72 (s, 1H), 8.65 (s, 1H), 8.64 (d, 1H), 7.80 (d, 1H), 7.59 (t, 1H), 4.05 (br s, 2H), 3.97 (br s, 2H), 2.53 br (s, 4H), 2.38 (s, 3H).

EXAMPLE 108

2-(4-Methyl-piperazin-1-yl)-4-naphthalen-1-yl-[1,3,5]triazine

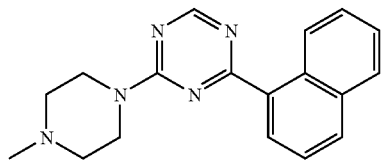

LC/MS: mass calcd. for $C_{18}H_{19}N_5$, 305.2; m/z found, 306.2 $[M+H]^+$ $^1$H NMR (CDCl$_3$): 8.82 (d, 1H), 8.74 (s, 1H), 8.15 (d, 1H), 7.98 (d, 1H), 7.90 (d, 1H), 7.58-7.48 (m, 3H), 4.00 (br s, 4H), 2.51 (br s, 4H), 2.36 (s, 3H).

EXAMPLE 109

Dimethyl-{4-[4-(4-methyl-piperazin-1-yl)-pyridin-2-yl]-thiophen-2-ylmethyl}-amine

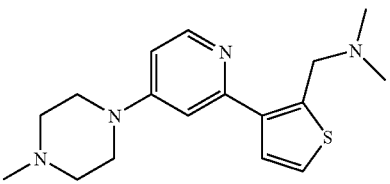

Step A: [3-(4-Chloro-pyridin-2-yl)-thiophen-2-ylmethyl]-dimethyl-amine

To a solution of 3-(4-chloro-pyridin-2-yl)-thiophene-2-carbaldehyde (20 mg, 0.1 mmol) in dichloromethane (3 mL) was added dimethylamine water solution (40%, 0.6 mL) and sodium triacetoxyborohydride (42 mg, 0.2 mmol). The resulting mixture was stirred at room temperature for 16 hours, then washed with NaHCO$_3$ solution and water and concentrated. The resulting residue was purified by preparative TLC to yield [3-(4-Chloro-pyridin-2-yl)-thiophen-2-ylmethyl]-dimethyl-amine.

LC/MS: mass calcd. for $C_{12}H_{13}ClN_2S$, 252.1; m/z found, 253.1 $[M+H]^+$ $^1$H NMR (CDCl$_3$): 8.58 (d, 1H), 7.67 (d, 1H), 7.34 (d, 1H), 7.28 (d, 1H), 7.21 (dd, 1H), 3.95 (s, 2H), 2.38 (s, 6H).

Step B: Preparation of Dimethyl-[4-[4-(4-methyl-piperazin-1-yl)-pyridin-2-yl]-thiophen-2-ylmethyl]-amine The title compound, [3-(4-Chloro-pyridin-2-yl)-thiophen-2-ylmethyl]-dimethyl-amine was prepared according to the procedure as described in Example 26, Step B substituting [3-(4-chloro-pyridin-2-yl)-thiophen-2-ylmethyl]-dimethyl-amine as appropriate.

LC/MS: mass calcd. for $C_{17}H_{24}N_4S$, 316.2; m/z found, 317.2 $[M+H]^+$ $^1$H NMR (CDCl$_3$): 8.35 (d, 1H), 7.31 (d, 1H), 7.24 (d, 1H), 7.11 (d, 1H), 6.62 (dd, 1H), 3.84 (s, 2H), 3.41 (t, 4H), 2.56 (t, 4H), 2.36 (s, 3H), 2.30 (s, 6H).

EXAMPLE 110

1-[2-(3-Furan-3-yl-phenyl)-pyridin-4-yl]-4-methyl-piperazine, Hydrochloride Salt

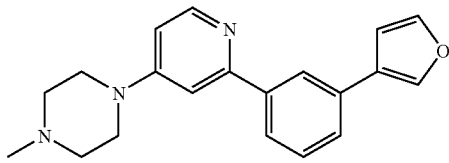

LC/MS: mass calcd. for $C_{20}H_{21}N_3O$, 319.2; m/z found, 320.3 [M+H]

$^1$H NMR (DMSO): 14.5 (m, 0.4H), 11.6 (m, 0.6H), 8.40-7.20 (m, 10H), 4.60 (m, 2H), 3.80-3.40 (m, 4H), 3.20 (t, 2H), 2.80 (s, 3H).

EXAMPLE 111

2-(4-Fluoro-3-methyl-phenyl)-4-(4-methyl-piperazin-1-yl)-[1,3,5]triazine

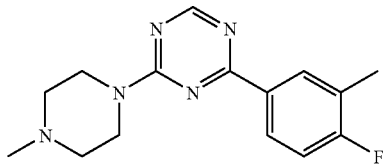

LC/MS: mass calcd. for $C_{15}H_{18}FN_5$, 287.2; m/z found, 288.2 $[M+H]^+$ $^1$H NMR (CDCl$_3$): 8.64 (s, 1H), 8.19-8.26 (m, 2H), 7.08 (t, 1H), 4.30 (br s, 4H), 2.97 (br s, 4H), 2.67 (s, 3H), 2.35 (s, 3H).

EXAMPLE 112

2-Biphenyl-4-yl-4-(4-methyl-piperazin-1-yl)-[1,3,5]triazine

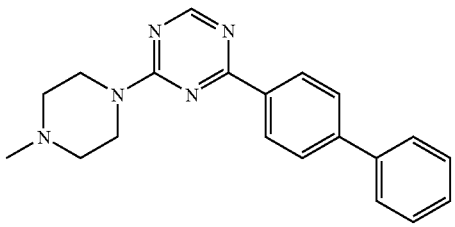

LC/MS: mass calcd. for $C_{20}H_{21}N_5$, 331.2; m/z found, 332.3 [M+H]$^+$.

$^1$H NMR (CDCl$_3$): 8.66 (s, 1H), 7.72-7.65 (m, 4H), 7.47 (t, 1H), 7.38 (t, 1H), 4.10 (br s, 2H), 3.99 (br s, 2H), 2.56 (br s, 4H), 2.40 (s, 3H).

EXAMPLE 113

2-(4-Methyl-piperazin-1-yl)-4-naphthalen-2-yl-[1,3,5]triazine

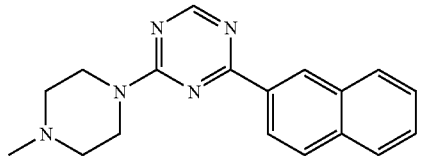

LC/MS: mass calcd. for $C_{18}H_{19}N_5$, 305.2; m/z found, 306.3 [M+H]$^+$.

$^1$H NMR (CDCl$_3$): 8.97 (s, 1H), 8.70 (s, 1H), 8.46 (dd, 1H), 7.99 (d, 1H), 7.90 (t, 2H), 7.58-7.50 (m, 1H), 4.15 (br s, 2H), 4.01 (br s, 2H), 2.60 (br s, 4H), 2.42 (s, 3H).

EXAMPLE 114

2-(4-Methyl-piperazin-1-yl)-4-phenyl-[1,3,5]triazine

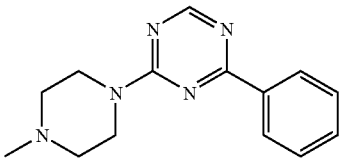

LC/MS: mass calcd. for $C_{14}H_{17}N_5$, 255.2; m/z found, 256.3 [M+H]$^+$ $^1$H NMR (CDCl$_3$): 8.64 (s, 1H), 8.41 (d, 2H), 7.56-7.44 (m, 3H), 4.06 (br s, 2H), 3.96 (br s, 2H), 2.51 (br s, 4H), 2.36 (s, 3H).

EXAMPLE 115

2-(2-Chloro-pyridin-3-yl)-4-(4-methyl-piperazin-1-yl)-[1,3,5]triazine

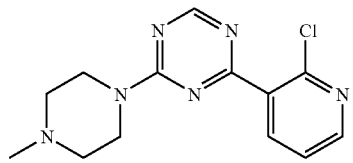

LC/MS: mass calcd. for $C_{13}H_{15}N_6$, 290.1; m/z found, 291.2 [M+H]$^+$ $^1$H NMR (CDCl$_3$): 8.66 (s, 1H), 8.48 (dd, 1H), 8.20 (dd, 1H), 7.35 (dd, 1H), 4.00-3.94 (m, 4H), 2.51-2.47 (m, 4H), 2.35 (s, 3H).

EXAMPLE 116

2-Bromo-4-[4-(4-methyl-piperazin-1-yl)-pyridin-2-yl]-phenylamine

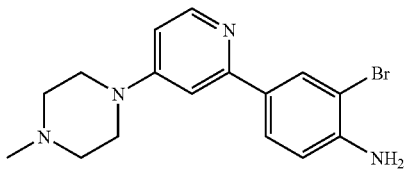

The title compound was prepared according to the methods described in Example 52.

LC/MS: mass calcd. for $C_{16}H_{19}BrN_4$, 346.1; m/z found, 347.3 [M+H]$^+$ $^1$H NMR (CDCl$_3$): 8.34 (d, 1H), 8.02 (d, 1H), 7.72 (dd, 1H), 6.97 (d, 1H), 6.83 (d, 1H), 6.64 (dd, 1H), 4.20 (s, 2H), 3.41 (t, 4H), 2.57 (t, 4H), 2.36 (s, 3H).

EXAMPLE 117

2-(4-Methyl-piperazin-1-yl)-4-(4-nitro-phenyl)-[1,3,5]triazine

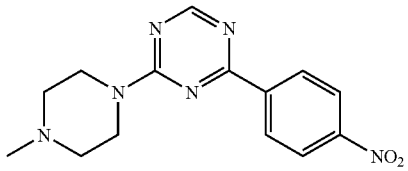

LC/MS: mass calcd. for $C_{14}H_{16}N_6O_2$, 300.1; m/z found, 301.2 [M+H]$^+$ $^1$H NMR (CDCl$_3$): 8.66 (s, 1H), 8.57 (d, 2H), 8.29 (d, 2H), 4.04 (br s, 2H), 3.96 (br s, 2H), 2.53-2.48 (m, 4H), 2.36 (s, 3H).

EXAMPLE 118

2-(2,4-Difluoro-phenyl)-4-(4-methyl-piperazin-1-yl)-[1,3,5]triazine

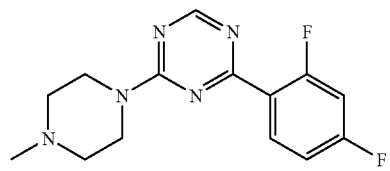

LC/MS: mass calcd. for $C_{14}H_{15}F_2N_5$, 291.1; m/z found, 292.3 [M+H]$^+$ $^1$H NMR (CDCl$_3$): 8.64 (s, 1H), 8.22-8.14 (m, 1H), 7.00-6.87 (m, 2H), 4.01-3.93 (m, 4H), 2.49 (t, 4H), 2.35 (s, 3H).

EXAMPLE 119

2-(5-Fluoro-2-methyl-phenyl)-4-(4-methyl-piperazin-1-yl)-[1,3,5]triazine

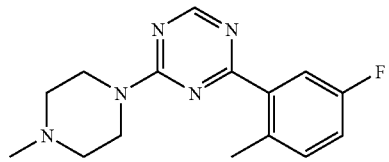

LC/MS: mass calcd. for $C_{15}H_{18}FN_5$, 287.2; m/z found, 288.3 [M+H]$^+$ $^1$H NMR (CDCl$_3$): 8.65 (s, 1H), 7.67 (dd, 1H), 7.22 (dd, 1H), 7.09-7.02 (m, 1H), 3.98-3.95 (m, 4H), 2.58 (s, 3H), 2.3d (s, 3H), 2.51-2.48 (m, 4H), 2.36 (s, 3H).

EXAMPLE 120

5-[4-(4-Methyl-piperazin-1-yl)-pyridin-2-yl]-biphenyl-2-ylamine

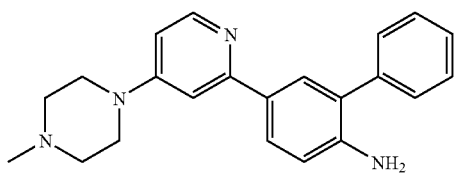

The title compound was prepared from 2-bromo-4-[4-(4-methyl-piperazin-1-yl)-pyridin-2-yl]-phenylamine according to the methods described in Example 26.

LC/MS: mass calcd. for $C_{22}H_{24}N_4$, 344.2; m/z found, 345.4 [M+H]$^+$ $^1$H NMR (CDCl$_3$): 8.34 (d, 1H), 8.02 (s, 1H), 7.81-730 (m, 7H), 7.02 (d, 1H), 6.83 (d, 1H), 6.58 (dd, 1H), 3.90 (s, 2H), 3.40 (t, 4H), 2.57 (t, 4H), 2.36 (s, 3H).

EXAMPLE 121

N-{3'-[4-(4-Methyl-piperazin-1-yl)-pyridin-2-yl]-biphenyl-4-yl}-acetamide

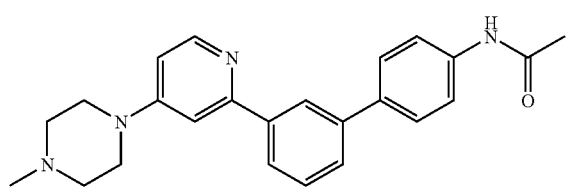

LC/MS: mass calcd. for $C_{24}H_{26}N_4O$, 386.2; m/z found, 387.4 [M+H]$^+$ $^1$H NMR (CDCl$_3$): 8.37 (d, 1H), 8.07 (s, 1H), 7.86-7.76 (m, 2H), 7.60-7.44 (m, 6H), 7.10 (d, 1H), 6.67 (dd, 1H), 3.44 (t, 4H), 2.60 (t, 4H), 2.39 (s, 3H), 2.15 (s, 3H).

EXAMPLE 122

5-[4-(4-Methyl-piperazin-1-yl)-pyridin-2-yl]-thiophene-2-carbonitrile

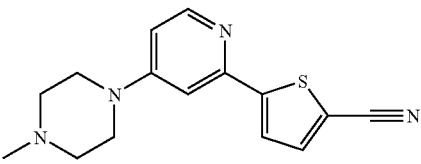

A mixture of 1-[2-(5-bromo-thiophen-2-yl)-pyridin-4-yl]-4-methyl-piperazine (41 mg, 0.13 mmol) and copper(I) cyanide (55 mg, 0.62 mmol) was heated in DMF at 180° C. by microwave for 30 minutes. After cooling, EtOAc was added and the resulting mixture was passed through Celite®. The filtrate was washed with water and the organic layer was concentrated. The resulting residue was purified by preparative TLC to yield the title compound.

LC/MS: mass calcd. for $C_{15}H_{16}N_4S$, 284.1; m/z found, 285.2 [M+H]$^+$ $^1$H NMR (CDCl$_3$): 8.24 (d, 1H), 7.58 (d, 1H), 7.43 (d, 1H), 7.04 (d, 1H), 6.62 (dd, 1H), 3.42 (t, 4H), 2.57 (t, 4H), 2.36 (s, 3H).

EXAMPLE 123

1-Methyl-4-[2-(6-methyl-biphenyl-3-yl)-pyridin-4-yl]-piperazine

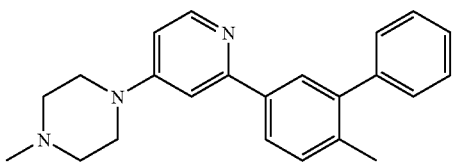

LC/MS: mass calcd. for $C_{23}H_{25}N_3$, 343.2; m/z found, 344.4 [M+H]$^+$ $^1$H NMR (CDCl$_3$): 8.43 (m, 1H), 7.82-7.30 (m, 8H), 7.02 (m, 1H), 6.63 (m, 1H), 3.48 (t, 4H), 2.62 (t, 4H), 2.39 (s, 3H), 2.30 (s, 3H).

EXAMPLE 124

1-Methyl-4-(2-phenyl-pyridin-4-yl)-piperazine

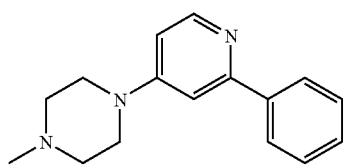

LC/MS: mass calcd. for $C_{16}H_{19}N_3$, 253.2; m/z found, 254.3 [M+H]$^+$
$^1$H NMR (CDCl$_3$): 8.36 (d, 1H), 7.90 (d, 2H), 7.46-7.36 (m, 3H), 7.08 (d, 1H), 6.63 (dd, 1H), 3.40 (t, 4H), 2.57 (t, 4H), 2.37 (s, 3H).

EXAMPLE 125

3-[4-(4-Methyl-piperazin-1-yl)-pyridin-2-yl]-thiophene-2-carbonitrile

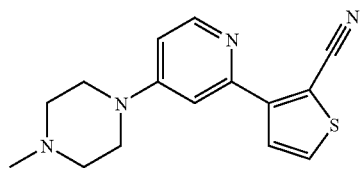

Step A:
3-(4-Chloro-pyridin-2-yl)-thiophene-2-carbonitrile

A mixture of 3-(4-chloro-pyridin-2-yl)-thiophene-2-carbaldehyde (103 mg, 0.46 mmol) and hydroxylamine hydrochloride (70 mg, 1 mmol) in pyridine (1 mL) was heated at 80° C. for 30 minutes. Acetic anhydride (0.8 mL) was added and the resulting mixture was heated at the temperature for another 3 hours. Ice water was added, the water solution was extracted with EtOAc and organic layer was concentrated. The resulting residue was purified by silica gel column to yield 3-(4-chloro-pyridin-2-yl)-thiophene-2-carbonitrile.
LC/MS: mass calcd. for $C_{10}H_5ClN_2S$, 220.1; m/z found, 221.1 [M+H]$^+$
$^1$H NMR (CDCl$_3$): 8.63 (d, 1H), 7.90 (d, 1H), 7.63 (s, 2H), 7.34 (dd, 1H).

Step B: 3-[4-(4-Methyl-piperazin-1-yl)-pyridin-2-yl]-thiophene-2-carbonitrile

The title compound was prepared from 3-(4-chloro-pyridin-2-yl)-thiophene-2-carbonitrile as described in Example 26, step B.
LC/MS: mass calcd. for $C_{15}H_{16}N_4S$, 284.1; m/z found, 285.3 [M+H]$^+$
$^1$H NMR (CDCl$_3$): 8.37 (d, 1H), 7.70 (d, 1H), 7.58 (d, 1H), 7.40 (d, 1H), 6.68 (dd, 1H), 3.44 (t, 4H), 2.58 (t, 4H), 2.38 (s, 3H).

EXAMPLE 126

2-(4-Methoxy-thiophen-3-yl)-4-(4-methyl-piperazin-1-yl)-[1,3,5]triazine

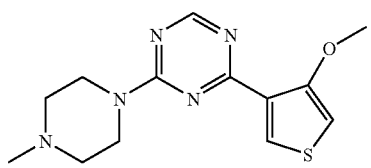

LC/MS: mass calcd. for $C_{13}H_{17}N_5OS$, 291.1; m/z found, 292.1 [M+H]$^+$
$^1$H NMR (CDCl$_3$): 8.63 (s, 1H), 8.24 (d, 1H), 6.36 (d, 1H), 4.01 (br s, 2H), 3.96 (br s, 2H), 3.94 (s, 3H), 2.55-2.52 (m, 4H), 2.38 (s, 3H).

EXAMPLE 127

2-(4-Methyl-piperazin-1-yl)-4-(5-pyridin-2-yl-thiophen-2-yl)-[1,3,5]triazine

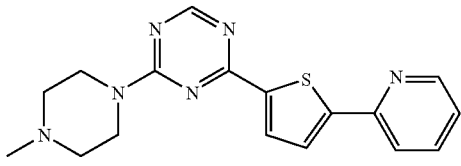

LC/MS: mass calcd. for $C_{17}H_{18}N_6S$, 338.1; m/z found, 339.2 [M+H]$^+$
$^1$H NMR (CDCl$_3$): 8.61-8.59 (dt, 1H), 8.54 (s, 1H), 8.01 (d, 1H), 7.71-7.69 (m, 2H), 7.59 (d, 1H), 7.23-7.15 (m, 1H), 4.01-3.98 (m, 2H), 3.92-3.89 (s, 2H), 2.47 (br s, 4H), 2.34 (s, 3H).

EXAMPLE 128

{4-[4-(4-Methyl-piperazin-1-yl)-pyridin-2-yl]-thiophen-2-yl}-methanol

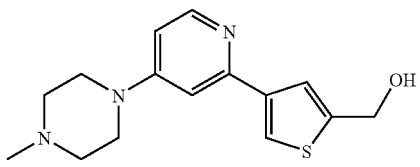

The title compound was prepared according to the methods described in Example 61.
LC/MS: mass calcd. for $C_{15}H_{19}N_3OS$, 289.1; m/z found, 290.2 [M+H]$^+$
$^1$H NMR (CDCl$_3$): 8.27 (d, 1H), 7.65 (s, 1H), 7.47 (s, 1H), 6.96 (d, 1H), 6.59 (dd, 1H), 4.82 (d, 1H), 3.40 (t, 4H), 2.57 (t, 4H), 2.38 (s, 3H), 2.00 (s, 1H).

EXAMPLE 129

4-[4-(4-Methyl-piperazin-1-yl)-pyridin-2-yl]-thiophene-2-carbonitrile

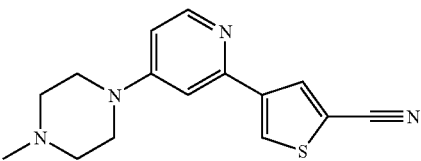

The title compound was prepared according to the methods described in Example 125.
LC/MS: mass calcd. for $C_{15}H_{16}N_4S$, 284.1; m/z found, 285.2 [M+H]$^+$ ¹H NMR (CDCl₃): 8.30 (d, 1H), 8.18-8.05 (m, 2H), 6.96 (d, 1H), 6.63 (dd, 1H), 3.44 (t, 4H), 2.60 (t, 4H), 2.39 (s, 3H).

EXAMPLE 130

1-Methyl-4-[2-(5-vinyl-thiophen-3-yl)-pyridin-4-yl]-piperazine

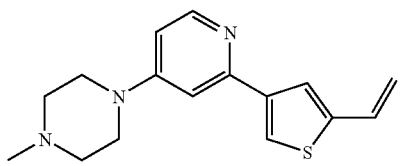

Step A: 4-Chloro-2-(5-vinyl-thiophen-3-yl)-pyridine

To a solution of methyltriphenylphosphonium bromide (180 mg, 0.5 mmol) in THF (3 mL) was added n-BuLi (1.6 M, 0.34 mL) at 0° C. After the mixture was stirred for 30 minutes, a solution of 4-(4-chloro-pyridin-2-yl)-thiophene-2-carbaldehyde (100 mg, 0.45 mmol) in THF (2 mL) was added. The resulting mixture was stirred at room temperature for 5 hours. Water was added and THF was removed. The water solution was extracted with EtOAc and organic layer was concentrated. The resulting residue was purified by silica gel column to yield 4-chloro-2-(5-vinyl-thiophen-3-yl)-pyridine.

¹H NMR (CDCl₃): 8.47 (d, 1H), 7.76 (d, 1H), 7.58 (d, 1H), 7.48 (d, 1H), 7.18 (dd, 1H), 6.82 (dd, 1H), 5.62 (d, 1H), 5.21 (d, 1H),

Step B: 1-Methyl-4-[2-(5-vinyl-thiophen-3-yl)-pyridin-4-yl]-piperazine

The title compound was prepared from 4-chloro-2-(5-vinyl-thiophen-3-yl)-pyridine as described in Example 26, step B.

LC/MS: mass calcd. for $C_{16}H_{19}N_3S$, 285.1; m/z found, 286.1 [M+H]⁺

¹H NMR (CDCl₃): 8.30 (d, 1H), 7.65 (d, 1H), 7.47 (d, 1H), 6.97 (d, 1H), 6.82 (dd, 1H), 6.60 (dd, 1H), 5.60 (d, 1H), 5.19 (d, 1H), 3.40 (t, 4H), 2.57 (t, 4H), 2.38 (s, 3H).

EXAMPLE 131

1-[2-(5-Ethyl-thiophen-3-yl)-pyridin-4-yl]-4-methyl-piperazine

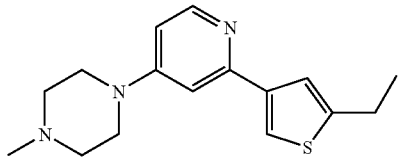

A solution of 1-Methyl-4-[2-(5-vinyl-thiophen-3-yl)-pyridin-4-yl]-piperazine in ethanol was treated with a catalytic amount of 10% palladium on carbon and placed under an H₂ atmosphere at room temperature. The resulting mixture was filtered and concentrated to yield the title compound.

LC/MS: mass calcd. for $C_{16}H_{21}N_3S$, 287.2; m/z found, 288.2 [M+H]⁺

¹H NMR (CDCl₃): 8.32 (d, 1H), 7.58 (d, 1H), 7.30 (d, 1H), 6.98 (d, 1H), 6.58 (dd, 1H), 3.40 (t, 4H), 2.86 (q, 2H), 2.57 (t, 4H), 2.38 (s, 3H), 1.35 (t, 3H).

EXAMPLE 132

1-[2-(5-Isopropenyl-thiophen-3-yl)-pyridin-4-yl]-4-methyl-piperazine

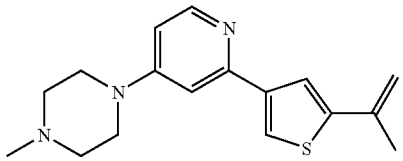

Step A: 1-[4-(4-Chloro-pyridin-2-yl)-thiophen-2-yl]-ethanol

To a solution of 4-(4-chloro-pyridin-2-yl)-thiophene-2-carbaldehyde (160 mg, 0.72 mmol) in THF (3 mL) was added methylmagnesium bromide (3 M, 1 mL) at −78° C. and the resulting mixture was stirred at the temperature for 3 hours. Water was added and THF was removed. The water solution was extracted with EtOAc and organic layer was concentrated. The resulting residue was purified by silica gel column to yield 1-[4-(4-chloro-pyridin-2-yl)-thiophen-2-yl]-ethanol ¹H NMR (CDCl₃): 8.47 (d, 1H), 7.78 (d, 1H), 7.54 (d, 1H), 7.46 (d, 1H), 7.17 (dd, 1H), 5.15 (m, 1H), 1.62 (d, 6H).

Step B: 1-[4-(4-Chloro-pyridin-2-yl)-thiophen-2-yl]-ethanone

To a solution of 1-[4-(4-chloro-pyridin-2-yl)-thiophen-2-yl]-ethanol (100 mg, 0.42 mmol) in dichloromethane (3 mL) was added PCC (111 mg, 0.5 mmol). The resulting mixture was stirred for 3 hours and then passed through Celite®. The filtrated was washed with water and the organic layer was concentrated. The resulting residue was purified by silica gel column to yield 1-[4-(4-chloro-pyridin-2-yl)-thiophen-2-yl]-ethanone Step C: 2-[4-(4-Chloro-pyridin-2-yl)-thiophen-2-yl]-propan-2-ol 2-[4-(4-Chloro-pyridin-2-yl)-thiophen-2-yl]-propan-2-ol was prepared from 1-[4-(4-chloro-pyridin-2-yl)-thiophen-2-yl]-ethanone as described in Example 132, step A.

Step D: 1-[2-(5-Isopropenyl-thiophen-3-yl)-pyridin-4-yl]-4-methyl-piperazine

The title compound was from 2-[4-(4-chloro-pyridin-2-yl)-thiophen-2-yl]-propan-2-ol as described in Example 26, step B.

LC/MS: mass calcd. for $C_{16}H_{21}N_3S$, 299.2; m/z found, 300.2 [M+H]⁺

EXAMPLE 133

2-(3,5-Difluoro-phenyl)-4-(4-mthyl-piperazin-1-yl)-[1,3,5]triazine

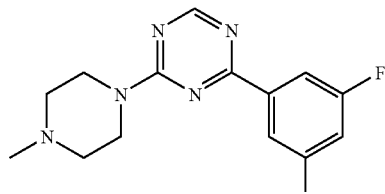

LC/MS: mass calcd. for $C_{14}H_{15}F_2N_5$, 291.1; m/z found, 292.2 [M+H]$^+$ $^1$H NMR (CDCl$_3$): 8.65 (s, 1H), 7.97-7.90 (m, 2H), 7.01-6.93 (m, 1H), 4.10 (br s, 2H), 4.05 (br s, 2H), 2.62 (br s, 4H), 2.45 (s, 3H).

EXAMPLE 134

2-(2-Chloro-4-fluoro-phenyl)-4-(4-methyl-piperazin-1-yl)-[1,3,5]triazine

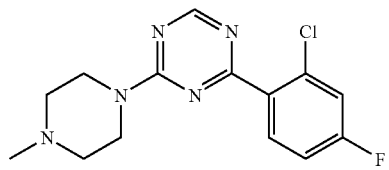

LC/MS: mass calcd. for $C_{14}H_{15}ClFN_5$, 307.1; m/z found, 308.1 [M+H]$^+$ $^1$H NMR (CDCl$_3$): 8.66 (s, 1H), 7.90 (dd, 1H), 7.23 (dd, 1H), 7.08 (dt, 1H), 3.99 (br s, 4H), 2.52 (br s, 4H), 2.38 (s, 3H).

EXAMPLE 135

2-(4-Methyl-piperazin-1-yl)-4-pyridin-2-yl-[1,3,5]triazine

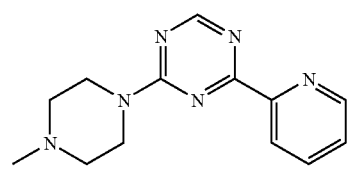

LC/MS: mass calcd. for $C_{13}H_{16}N_6$, 256.1; m/z found, 257.0 [M+H]$^+$ $^1$H NMR (CDCl$_3$): 8.84-8.81 (m, 1H), 8.74 (s, 1H), 8.46-8.43 (m, 1H), 7.85 (dt, 1H), 7.46-7.42 (m, 1H), 4.09-4.05 (m, 2H), 3.99-3.96 (m, 2H), 2.53-2.49 (m, 4H), 2.36 (s, 3H).

EXAMPLE 136

2-(4-Methyl-piperazin-1-yl)-4-(3-methyl-thiophen-2-yl)-[1,3,5]triazine

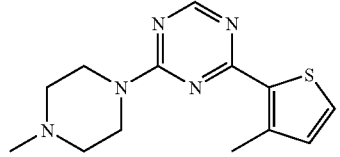

LC/MS: mass calcd. for $C_{13}H_{17}N_5$, 275.1; m/z found, 276.1 [M+H]$^+$ $^1$H NMR (CDCl$_3$): 8.53 (s, 1H), 7.38 (d, 1H), 6.94 (d, 1H), 3.94 (br s, 4H), 2.69 (s, 3H), 2.51-2.48 (m, 4H), 2.35 (s, 3H).

EXAMPLE 137

1-[2-(5-Chloro-2-methyl-thiophen-3-yl)-pyridin-4-yl]-4-methyl-piperazine

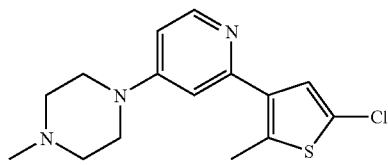

The title compound was prepared according to the methods as described in Example 47.

LC/MS: mass calcd. for $C_{15}H_{18}ClN_3S$, 307.1; m/z found, 308.1 [M+H]$^+$ $^1$H NMR (CDCl$_3$): 8.32 (d, 1H), 7.05 (s, 1H), 6.76 (d, 1H), 6.60 (dd, 1H), 3.38 (t, 4H), 2.56 (s, 3H), 2.54 (t, 4H), 2.36 (s, 3H).

EXAMPLE 138

1-Methyl-4-[2-(5-methyl-furan-2-yl)-pyridin-4-yl]-piperazine

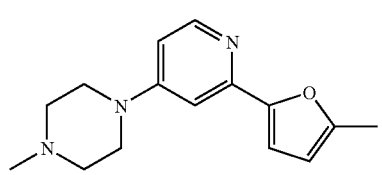

LC/MS: mass calcd. for $C_{15}H_{19}N_3O$, 257.2; m/z found, 258.1 [M+H]$^+$ $^1$H NMR (CDCl$_3$): 8.25 (d, 1H), 7.05 (d, 1H), 6.88 (d, 1H), 6.52 (dd, 1H), 6.09 (dd, 1H), 3.40 (t, 4H), 2.57 (t, 4H), 2.40 (s, 3H), 2.37 (s, 3H).

EXAMPLE 139

2-(2,5-Dichloro-thiophen-3-yl)-4-(4-methyl-piperazin-1-yl)-[1,3,5]triazine

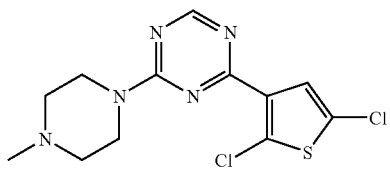

LC/MS: mass calcd. for $C_{12}H_{13}Cl_2N_5S$, 329.0; m/z found, 330.0 [M+H]$^+$ $^1$H NMR (CDCl$_3$): 8.60 (s, 1H), 7.50 (s, 1H), 4.00-3.92 (m, 4H), 2.51-2.48 (m, 4H), 2.36 (s, 3H).

EXAMPLE 140

2-Benzo[b]thiophen-3-yl-4-(4-methyl-piperazin-1-yl)-[1,3,5]triazine

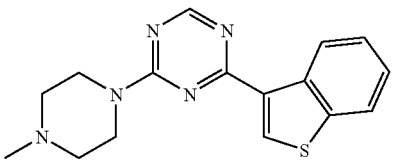

LC/MS: mass calcd. for $C_{16}H_{17}N_5S$, 311.1; m/z found, 312.1 [M+H]$^+$ $^1$H NMR (CDCl$_3$): 8.98 (d, 1H), 8.68 (s, 1H), 8.65 (s, 1H), 7.89 (d, 1H), 7.49 (t, 1H), 7.40 (t, 1H), 4.05 (br s, 2H), 3.98 (br s, 2H), 2.52 (br s, 4H), 2.37 (s, 3H).

EXAMPLE 141

1-Methyl-4-[2-(2-vinyl-thiophen-3-yl)-pyridin-4-yl]-piperazine

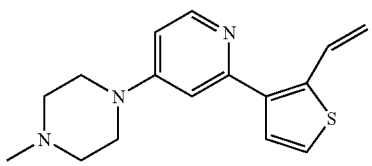

The title compound was prepared according to the methods as described in Example 130.

LC/MS: mass calcd. for $C_{16}H_{19}N_3S$, 285.1; m/z found, 286.1 [M+H]$^+$ $^1$H NMR (CDCl$_3$): 8.37 (d, 1H), 7.27-7.12 (m, 3H), 6.80 (d, 1H), 6.63 (dd, 1H), 5.65 (d, 1H), 5.21 (d, 1H), 3.42 (t, 4H), 2.58 (t, 4H), 2.38 (s, 3H).

EXAMPLE 142

1-Methyl-4-(3-methyl-2-thiophen-3-yl-pyridin-4-yl)-piperazine

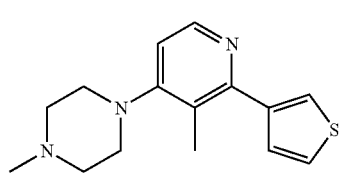

The title compound was prepared according to the methods as described in Example 26 substituting 2,4-dichloro-3-methylpyridine as appropriate. (The 2,4-dichloro-3-methyl-pyridine was prepared by treating a solution of 2,4-dichloropyridine in THF with LDA at −78° C. followed by quenching with iodomethane.)

LC/MS: mass calcd. for $C_{15}H_{19}N_3S$, 273.1; m/z found, 274.1 [M+H]$^+$ $^1$H NMR (CDCl$_3$): 8.37 (d, 1H), 7.51 (dd, 1H), 7.39 (dd, 1H), 7.36 (dd, 1H), 6.80 (d, 1H), 3.10 (t, 4H), 2.60 (t, 4H), 2.38 (s, 3H), 2.35 (s, 3H).

EXAMPLE 143

2-Methyl-4-(4-methyl-piperazin-1-yl)-6-(3,4,5-trifluoro-phenyl)-[1,3,5]triazine

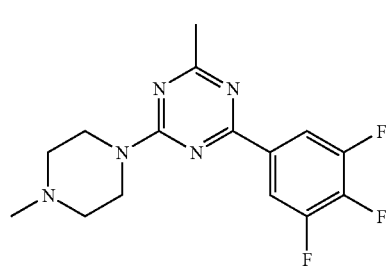

LC/MS: mass calcd. for $C_{15}H_{16}F_3N_5$, 323.1; m/z found, 324.1 [M+H]$^+$ $^1$H NMR (CDCl$_3$): 8.11-8.04 (m, 2H), 4.01 (br s, 4H), 2.53 (br s, 4H), 2.48 (s, 3H), 2.38 (s, 3H).

EXAMPLE 144

1-[2-(5-Chloro-3-methyl-thiophen-2-yl)-pyridin-4-yl]-4-methyl-piperazine

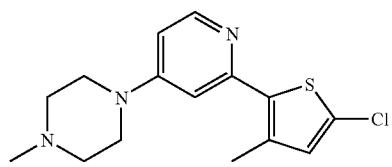

LC/MS: mass calcd. for $C_{15}H_{18}ClN_3S$, 307.1; m/z found, 308.1 [M+H]$^+$ $^1$H NMR (CDCl$_3$): 8.25 (d, 1H), 6.86 (d, 1H), 6.72 (s, 1H), 6.57 (dd, 1H), 3.39 (t, 4H), 2.57 (t, 4H), 2.41 (s, 3H), 2.36 (s, 3H).

EXAMPLE 145

1-(2-[2,2']Bithiophenyl-5-yl-Pyridin-4-yl)-4-methyl-piperazine

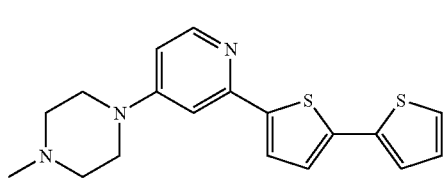

LC/MS: no exact mass was detected.

$^1$H NMR (CDCl$_3$): 8.25 (d, 1H), 7.46 (d, 1H), 7.25-7.20 (m, 2H), 7.19 (d, 1H), 7.40-7.20 (m, 2H), 6.58 (dd, 1H), 3.40 (t, 4H), 2.57 (t, J=5.0, 4H), 2.37 (s, 3H).

EXAMPLE 146

1-[2-(4,5-Dichloro-thiophen-2-yl)-pyridin-4-yl]-4-methyl-piperazine

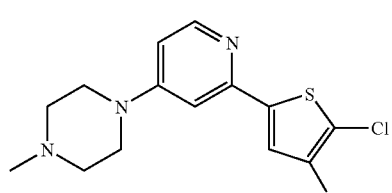

LC/MS: mass calcd. for $C_{13}H_{14}Cl_2N_4S$, 328.0; m/z found, 329.1 [M+H]$^+$.

$^1$H NMR (CDCl$_3$): 8.20 (d, 1H), 7.27 (s, 1H), 6.92 (d, 1H), 6.59 (dd, 1H), 3.40 (t, 4H), 2.57 (t, J=5.0, 4H), 2.37 (s, 3H).

EXAMPLE 147

2-(4-Chloro-thiophen-2-yl)-4-(4-methyl-piperazin-1-yl)-[1,3,5]triazine

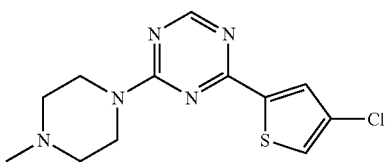

LC/MS: mass calcd. for $C_{12}H_{14}ClN_5S$, 295.1; m/z found, 296.0 [M+H]$^+$ $^1$H NMR (CDCl$_3$): 8.54 (s, 1H), 7.88 (s, 1H), 7.29 (s, 1H), 3.99 (br s, 4H), 2.55 (br s, 4H), 2.41 (s, 3H).

EXAMPLE 148

1-[2-(3-Chloro-thiophen-2-yl)-pyridin-4-yl]-4-methyl-piperazine

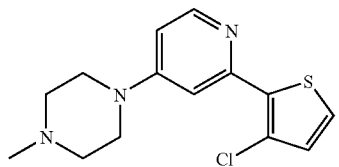

LC/MS: mass calcd. for $C_{14}H_{16}ClN_3S$, 293.1; m/z found, 294.0 [M+H]$^+$.

$^1$H NMR (CDCl$_3$): 8.24 (d, 1H), 7.37 (d, 1H), 7.15 (d, 1H), 6.99 (d, 1H), 6.60 (dd, 1H), 3.40 (t, J=5.0, 4H), 2.57 (t, J=5.0, 4H), 2.36 (s, 3H).

EXAMPLE 149

4-(4-Chloro-thiophen-2-yl)-2-(4-methyl-piperazin-1-yl)-pyrimidine

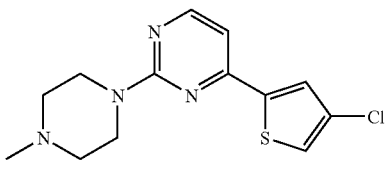

The title compound was prepared according to the methods described in Example 69.

LC/MS: mass calcd. for $C_{13}H_{15}ClN_4S$, 294.1; m/z found, 295.0 [M+H]$^+$.

$^1$H NMR (CDCl$_3$): 8.32 (d, 1H), 7.50 (d, 1H), 7.21 (d, 1H), 6.76 (d, 1H), 3.90 (t, 4H), 2.50 (t, 4H), 2.35 (s, 3H).

EXAMPLE 150

2-Chloro-4-(3-chloro-thiophen-2-yl)-6-(4-methyl-piperazin-1-yl)-pyrimidine

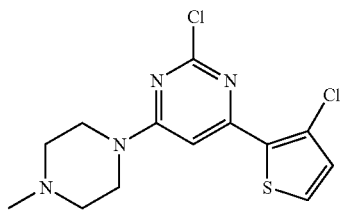

Step A:
2,4-Dichloro-6-(3-chloro-thiophen-2-yl)-pyrimidine

To a solution of 3-chlorothiophene (384 mg, 3.0 mmol) in THF (6 mL) at −78° C. was added n-BuLi (1.6 M, 2 mL) and the resulting mixture stirred for 45 minutes. The resulting product was added to a solution of 2,4-dichloropyrimidine (430 mg, 2.9 mmol) in ether (10 mL) at −30° C. and the resulting mixture stirred for 30 minutes, then warmed up to 0° C. and stirred for another 30 minutes. DDQ (700 mg, 3 mmol) was added and the resulting mixture was stirred overnight, then filtered through Celite®. The filtrate was concentrated and the residue was purified by silica gel column (EtOAc/hexanes, 1:5) to yield a white solid.

Step B: Preparation of the Title Compound

To a vial was added 2,4-dichloro-6-(3-chloro-thiophen-2-yl)-pyrimidine (50 mg, 0.19 mmol), 1-methylpiperazine (50 mg, 0.5 mmol), and ethanol (2 mL). The resulting mixture was stirred at room temperature for 3 hrs. Ethanol was removed and the resulting residue was dissolved with EtOAc. The organic layer was washed with 1N hydrochloric acid and concentrated to yield the title compound as a solid.

LC/MS: mass calcd. for $C_{13}H_{14}Cl_2N_4S$, 328.0; m/z found, 329.1 $[M+H]^+$.

$^1$H NMR (CDCl$_3$): 7.43 (d, 1H), 7.36 (s, 1H), 7.01 (d, 1H), 3.76 (t, 4H), 2.50 (t, 4H), 2.35 (s, 3H).

EXAMPLE 151

2-Chloro-4-(4-methyl-piperazin-1-yl)-6-thiophen-2-yl-pyrimidine

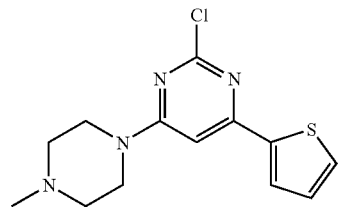

To a solution of 2-chloro-4-(3-chloro-thiophen-2-yl)-6-(4-methyl-piperazin-1-yl)-pyrimidine (30 mg, 0.1 mmol) in methanol (2 mL) was added 10% Pd/C (15 mg). The resulting mixture was stirred under hydrogen balloon overnight. Palladium on carbon was removed through Celite® filtration. The filtrate was dried and purified by TLC plate to yield the title compound as a solid.

LC/MS: mass calcd. for $C_{13}H_{15}ClN_4S$, 294.1; m/z found, 295.0 $[M+H]^+$.

$^1$H NMR (CDCl$_3$): 7.70 (dd, 1H), 7.46 (dd, 1H), 7.11 (dd, 1H), 6.63 (s, 1H), 3.72 (t, 4H), 2.50 (t, 4H), 2.35 (s, 3H).

EXAMPLE 152

Biological Testing

Binding Assay on Recombinant Human Histamine H$_4$ Receptor

SK-N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 sec at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine H$_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, K$_i$ values were calculated, based on an experimentally determined K$_D$ value of 5 nM and a ligand concentration of 5 nM, according to Y. C. Cheng and W. H. Prusoff (*Biochem. Pharmacol.* 1973, 22(23):3099-3108): $K_i=(IC_{50})/(1+([L]/(K_D))$. Results for the compounds tested in this assay are presented in Table 5 as an average of results obtained.

TABLE 5

| H$_4$ Binding | |
|---|---|
| ID No. | Ki (nM) |
| 1 | 44 |
| 2 | 76 |
| 3 | 22 |
| 4 | 75 |
| 5 | 33 |
| 6 | 115 |
| 7 | 87 |
| 8 | 73 |
| 9 | 22 |
| 10 | 36 |
| 11 | 7 |
| 12 | 35 |
| 13 | 10 |
| 14 | 30 |
| 15 | 2 |
| 16 | 50 |
| 17 | 8 |
| 18 | 37 |

TABLE 5-continued

| H₄ Binding | |
|---|---|
| ID No. | Ki (nM) |
| 19 | 172 |
| 20 | 950 |
| 21 | 2333 |
| 22 | 757 |
| 23 | 31 |
| 24 | 267 |
| 25 | 66 |
| 26 | 37 |
| 27 | 87 |
| 28 | 25 |
| 29 | 64 |
| 30 | 138 |
| 31 | 75 |
| 32 | 129 |
| 33 | 577 |
| 34 | 90 |
| 35 | 130 |
| 36 | 97 |
| 37 | 65 |
| 38 | 52 |
| 39 | 433 |
| 40 | 867 |
| 41 | 2600 |
| 42 | 767 |
| 44 | 284 |
| 45 | 179 |
| 46 | 1667 |
| 47 | 800 |
| 48 | 23 |
| 49 | 79 |
| 50 | 103 |
| 51 | 90 |
| 52 | 47 |
| 53 | 68 |
| 54 | 15 |
| 55 | 58 |
| 56 | 60 |
| 57 | 10 |
| 58 | 33 |
| 59 | 187 |
| 60 | 139 |
| 61 | 211 |
| 62 | 208 |
| 63 | 10000 |
| 64 | 513 |
| 65 | 343 |
| 66 | 216 |
| 67 | 133 |
| 68 | 397 |
| 69 | 537 |
| 71 | >10000 |
| 72 | 397 |
| 73 | 120 |
| 74 | 275 |
| 75 | >10000 |
| 77 | 1477 |
| 78 | 950 |
| 79 | 567 |
| 80 | 567 |
| 81 | 241 |
| 82 | 1690 |
| 83 | 810 |
| 84 | 427 |
| 85 | 3017 |
| 86 | 251 |
| 87 | 172 |
| 88 | 453 |
| 89 | 170 |
| 90 | 153 |
| 91 | 533 |
| 92 | 2000 |
| 93 | 580 |
| 94 | 1667 |
| 95 | 223 |
| 96 | 500 |
| 98 | 271 |
| 99 | >10000 |
| 100 | 363 |
| 101 | >10000 |
| 102 | 820 |
| 103 | 483 |
| 104 | >10000 |
| 105 | — |
| 106 | 159 |
| 107 | 1517 |
| 108 | 1927 |
| 109 | 253 |
| 110 | 228 |
| 111 | 2013 |
| 112 | 1513 |
| 113 | >10000 |
| 114 | 105 |
| 115 | 111 |
| 116 | >10000 |
| 117 | >10000 |
| 118 | 128 |
| 119 | — |
| 120 | 627 |
| 121 | 107 |
| 122 | 94 |
| 123 | 60 |
| 124 | 2253 |
| 125 | 677 |
| 126 | 3833 |
| 127 | >10000 |
| 128 | 170 |
| 129 | 443 |
| 130 | 643 |
| 131 | >10000 |
| 132 | 633 |
| 133 | 3333 |
| 134 | 269 |
| 135 | 109 |
| 136 | 79 |
| 137 | 78 |
| 138 | 99 |
| 139 | 857 |
| 140 | 52 |
| 141 | 294 |
| 142 | 353 |
| 143 | 193 |
| 144 | 347 |
| 145 | 268 |
| 146 | 1110 |
| 147 | 193 |
| 148 | 107 |
| 149 | 3333 |
| 150 | 833 |
| 151 | 137 |
| 152 | 153 |
| 153 | 273 |
| 154 | 93 |
| 155 | 174 |

EXAMPLE 153

As a specific embodiment of an oral composition, 100 mg of a compound of the present invention is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents

What is claimed is:

1. A process for the preparation compounds of formula (I-P), pharmaceutically acceptable salts of compounds of Formula (I-P), pharmaceutically acceptable prodrugs of compounds of Formula (I-P), and pharmaceutically active metabolites of compounds of Formula (I-P),

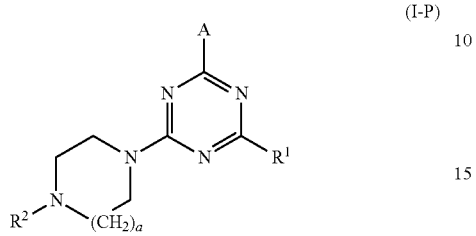

(I-P)

wherein
A is selected from the group consisting of H and $C_{1-4}$alkyl;
$R^1$ is selected from the group consisting of aryl and heteroaryl;
wherein said aryl or heteroaryl is optionally substituted with one or more substituents independently selected from the group consisting of halo, hydroxy, $C_{1-4}$alkyl, halogenated $C_{1-4}$alkyl, hydroxy substituted $C_{1-4}$alkyl, $C_{2-4}$alkenyl, $C_{1-4}$alkoxy, cyano, nitro, $NR^AR^B$, —$C_{1-4}$alkyl-O—$C_{1-4}$alkyl, —$C_{1-4}$alkyl-$NR^AR^B$, phenyl, Sph, and 5 to 6 membered heteroaryl;
$R^A$ and $R^B$ are each independently selected from the group consisting of H and $C_{1-4}$alkyl;
Sph is phenyl substituted with one or more substituents independently selected from the group consisting of halo, cyano, $C_{1-4}$alkyl, $C_{1-4}$alkoxy, —$NR^CR^D$, —C(O)—$NR^CR^D$, —C(O)OH, —C(O)O—$C_{1-4}$alkyl, (—C(O)-4-morpholinyl), (—C(O)-1-pyrrolidinyl) and (—$NR^E$—C(O)—$C_{1-4}$alkyl);
$R^C$ and $R^D$ are each independently selected from the group consisting of H and $C_{1-4}$alkyl; alternatively, $R^C$ and $R^D$ are taken together with the nitrogen atom to which they are bound to from a 5 to 6 membered, saturated, nitrogen-containing ring;
$R^E$ is selected from the group consisting of H and $C_{1-4}$alkyl;
a is 1;
$R^2$ is selected from the group consisting of H and $C_{1-4}$alkyl;
comprising:

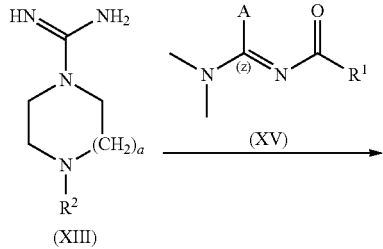

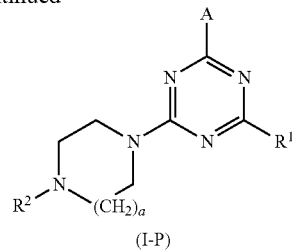

(I-P)

reacting a compound of formula (XIII) with a compound of formula (XV) in an anhydrous organic solvent.

2. A process as in claim 1, further comprising:

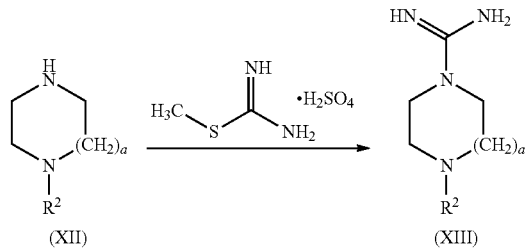

reacting a compound of formula (XII), with S-methylisothiourea sulfate.

3. A process as in claim 1, further comprising:

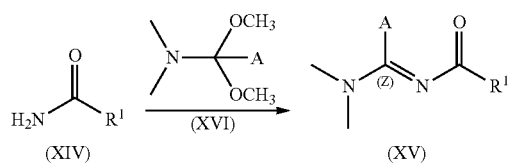

reacting a compound of formula (XIV), with a compound of formula (XVI), at a temperature in the range of from about 50° C. to about 100° C.

4. A process as in claim 1, wherein said reacting a compound of formula (XIII) with a compound of formula (XV) is performed in the presence of an inorganic base, and said anhydrous organic solvent is an anhydrous polar aprotic solvent.

5. A process as in claim 4, wherein said inorganic base is selected from the group consisting of potassium t-butoxide, sodium t-butoxide, and mixtures thereof, said anhydrous organic solvent is selected from the group consisting of 1,4-dioxane, THF, and mixtures thereof, and said reacting is performed at the reflux temperature of said anhydrous organic solvent.

* * * * *